US010226212B2

(12) United States Patent
Duesterhoft et al.

(10) Patent No.: US 10,226,212 B2
(45) Date of Patent: Mar. 12, 2019

(54) APPURTENANCES TO CAVITY WOUND DRESSINGS

(71) Applicant: Elwha LLC, Bellevue, WA (US)

(72) Inventors: Paul Duesterhoft, Issaquah, WA (US); Nicholas Dykstra, Seattle, WA (US); Daniel Hawkins, Bellevue, WA (US); Roderick A. Hyde, Redmond, WA (US); Jordin T. Kare, Seattle, WA (US); Eric C. Leuthardt, St. Louis, MO (US); Elizabeth L. Schubert, Bellevue, WA (US); Clarence T. Tegreene, Mercer Island, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 1155 days.

(21) Appl. No.: 13/795,667

(22) Filed: Mar. 12, 2013

(65) Prior Publication Data

US 2013/0274563 A1    Oct. 17, 2013

Related U.S. Application Data

(63) Continuation-in-part of application No. 13/445,174, filed on Apr. 12, 2012, which is a continuation-in-part of application No. 13/445,220, filed on Apr. 12, 2012, now Pat. No. 9,084,530.

(51) Int. Cl.
A61B 5/00        (2006.01)
A61B 5/01        (2006.01)

(52) U.S. Cl.
CPC .............. *A61B 5/4848* (2013.01); *A61B 5/01* (2013.01); *A61B 5/6885* (2013.01); *A61B 5/445* (2013.01)

(58) Field of Classification Search
USPC ..................... 600/573, 583; 604/319; 602/42
See application file for complete search history.

(56) References Cited

U.S. PATENT DOCUMENTS 3,927,669 A * 12/1975 Glatt ................. A61F 13/00021
                                                    602/47
4,384,288 A    5/1983 Walton
(Continued)

FOREIGN PATENT DOCUMENTS

EP         0 430 608 A1     6/1991
WO      WO 00/08203         2/2000
(Continued)

OTHER PUBLICATIONS

U.S. Appl. No. 14/252,136, Duesterhoft et al.
(Continued)

*Primary Examiner* — May Abouelela
(74) *Attorney, Agent, or Firm* — Dorsey & Whitney LLP

(57) ABSTRACT

Appurtenances to cavity wound medical dressings are described. In some embodiments, an appurtenance to a cavity wound dressing includes: a substrate including at least one wound-facing surface, the wound-facing surface configured to be oriented facing a wound surface of a cavity wound; and a plurality of sensor units attached to the substrate, the plurality of sensor units oriented and positioned on the substrate relative to the wound surface of the cavity wound.

15 Claims, 20 Drawing Sheets

FIG. 1B

(56) References Cited

U.S. PATENT DOCUMENTS

| | | | |
|---|---|---|---|
| 4,430,998 A * | 2/1984 | Harvey | A61B 17/085 606/216 |
| 4,753,232 A * | 6/1988 | Ward | A61F 13/023 602/52 |
| 4,924,866 A | 5/1990 | Yoon | |
| 5,047,047 A * | 9/1991 | Yoon | A61B 17/083 606/213 |
| 5,507,775 A * | 4/1996 | Ger | A61B 17/08 606/215 |
| 5,704,352 A | 1/1998 | Tremblay et al. | |
| 5,876,365 A | 3/1999 | Hart | |
| 5,904,671 A * | 5/1999 | Navot | A61F 13/20 340/573.5 |
| 5,912,114 A | 6/1999 | Hutchinson et al. | |
| 5,939,205 A | 8/1999 | Yokoyama et al. | |
| 5,964,723 A * | 10/1999 | Augustine | A61F 7/007 602/2 |
| 5,986,163 A * | 11/1999 | Augustine | A61F 7/007 602/2 |
| 6,037,879 A | 3/2000 | Tuttle | |
| 6,248,084 B1 * | 6/2001 | Augustine | A61F 7/007 602/14 |
| 6,270,455 B1 | 8/2001 | Brown | |
| 6,283,938 B1 | 9/2001 | McConnell | |
| 6,348,640 B1 | 2/2002 | Navot et al. | |
| 6,420,622 B1 | 7/2002 | Johnston et al. | |
| 6,569,189 B1 * | 5/2003 | Augustine | A61F 7/007 602/14 |
| 6,693,513 B2 * | 2/2004 | Tuttle | G06K 19/0716 340/10.1 |
| 6,863,220 B2 | 3/2005 | Selker | |
| 6,889,165 B2 | 5/2005 | Lind et al. | |
| 6,963,772 B2 | 11/2005 | Bloom et al. | |
| 7,030,764 B2 | 4/2006 | Smith et al. | |
| 7,055,754 B2 | 6/2006 | Forster | |
| 7,215,976 B2 | 5/2007 | Brideglall | |
| 7,297,112 B2 | 11/2007 | Zhou et al. | |
| 7,361,184 B2 | 4/2008 | Joshi | |
| 7,372,780 B1 | 5/2008 | Braunberger | |
| 7,411,505 B2 | 8/2008 | Smith et al. | |
| 7,446,660 B2 | 11/2008 | Posamentier | |
| 7,479,886 B2 | 1/2009 | Burr | |
| 7,507,675 B2 | 3/2009 | Zuilhof et al. | |
| 7,520,872 B2 * | 4/2009 | Biggie | A61M 1/0088 601/6 |
| 7,612,424 B1 | 11/2009 | Espinosa et al. | |
| 7,666,151 B2 | 2/2010 | Sullivan et al. | |
| 7,667,606 B2 | 2/2010 | Packert et al. | |
| 7,703,334 B2 | 4/2010 | Cochran | |
| 7,724,136 B2 | 5/2010 | Posamentier | |
| 7,794,925 B2 | 9/2010 | Cullen | |
| 7,813,226 B2 | 10/2010 | Braunberger | |
| 7,825,776 B2 | 11/2010 | Smith et al. | |
| 7,838,717 B2 * | 11/2010 | Haggstrom | A61F 13/0203 128/888 |
| 7,883,494 B2 | 2/2011 | Martin | |
| 7,896,856 B2 * | 3/2011 | Petrosenko | A61F 13/00 602/41 |
| 7,914,867 B2 | 3/2011 | Mori et al. | |
| 7,945,302 B2 | 5/2011 | McAdams | |
| 7,951,605 B2 | 5/2011 | Pitner et al. | |
| 7,964,390 B2 | 6/2011 | Rozakis et al. | |
| 7,986,235 B2 | 7/2011 | Posamentier | |
| 8,014,234 B2 | 9/2011 | Braunberger | |
| 8,048,046 B2 * | 11/2011 | Hudspeth | A61M 1/0088 604/119 |
| 8,057,446 B2 * | 11/2011 | Kane | A61F 13/0203 604/304 |
| 8,257,328 B2 * | 9/2012 | Augustine | A61M 1/0049 604/313 |
| 8,350,116 B2 * | 1/2013 | Lockwood | A61F 13/02 602/42 |
| 8,376,972 B2 * | 2/2013 | Fleischmann | A61F 13/00068 601/6 |
| 8,690,845 B2 | 4/2014 | Long et al. | |
| 8,760,295 B2 | 6/2014 | Forster | |
| 8,785,713 B2 * | 7/2014 | Hong | A61L 15/425 602/41 |
| 8,795,257 B2 | 8/2014 | Coulthard et al. | |
| 8,808,274 B2 | 8/2014 | Hartwell | |
| 8,945,030 B2 * | 2/2015 | Weston | A61M 1/0088 602/2 |
| 8,946,499 B2 * | 2/2015 | Iyer | A61L 15/42 602/41 |
| 9,011,393 B2 | 4/2015 | Kazala, Jr. et al. | |
| 9,050,398 B2 | 6/2015 | Armstrong et al. | |
| 9,168,180 B2 * | 10/2015 | Ha | A61F 13/02 |
| 9,422,934 B2 | 8/2016 | Locke et al. | |
| 2003/0199783 A1 | 10/2003 | Bloom et al. | |
| 2003/0216663 A1 | 11/2003 | Jersey-Willuhn et al. | |
| 2004/0073151 A1 | 4/2004 | Weston | |
| 2004/0210280 A1 | 10/2004 | Liedtke | |
| 2006/0036145 A1 | 2/2006 | Brister et al. | |
| 2006/0047218 A1 | 3/2006 | Bloom et al. | |
| 2007/0171076 A1 | 7/2007 | Stevens et al. | |
| 2007/0203442 A1 | 8/2007 | Bechert et al. | |
| 2007/0204691 A1 | 9/2007 | Bogner et al. | |
| 2007/0231380 A1 | 10/2007 | Shah et al. | |
| 2007/0247316 A1 | 10/2007 | Wildman et al. | |
| 2007/0252712 A1 | 11/2007 | Allen et al. | |
| 2007/0269851 A1 | 11/2007 | Sanders et al. | |
| 2008/0132821 A1 | 6/2008 | Propp et al. | |
| 2008/0166397 A1 | 7/2008 | Trotter et al. | |
| 2008/0171957 A1 | 7/2008 | Connolly et al. | |
| 2008/0234616 A1 * | 9/2008 | Shives | A61F 13/00068 602/13 |
| 2009/0167495 A1 | 7/2009 | Smith et al. | |
| 2009/0192369 A1 | 7/2009 | Say et al. | |
| 2009/0209883 A1 | 8/2009 | Higgins et al. | |
| 2009/0227969 A1 * | 9/2009 | Jaeb | A61M 1/0088 604/313 |
| 2009/0243813 A1 | 10/2009 | Smith et al. | |
| 2009/0299161 A1 | 12/2009 | Cullen et al. | |
| 2010/0010477 A1 * | 1/2010 | Augustine | A61M 1/0049 604/543 |
| 2010/0022990 A1 | 1/2010 | Karpowicz et al. | |
| 2010/0030167 A1 | 2/2010 | Thirstrup et al. | |
| 2010/0100061 A1 | 4/2010 | Odland | |
| 2010/0125258 A1 * | 5/2010 | Coulthard | A61F 13/0203 604/319 |
| 2010/0166694 A1 | 7/2010 | Stephens et al. | |
| 2010/0204606 A1 | 8/2010 | Kim et al. | |
| 2010/0228206 A1 | 9/2010 | Larsson | |
| 2010/0249733 A9 * | 9/2010 | Blott | A61B 17/7092 604/315 |
| 2010/0318052 A1 * | 12/2010 | Ha | A61F 13/02 604/385.01 |
| 2010/0331634 A1 | 12/2010 | Müller et al. | |
| 2011/0015591 A1 | 1/2011 | Hanson et al. | |
| 2011/0034906 A1 * | 2/2011 | Malhi | A61M 1/0088 604/543 |
| 2011/0054340 A1 | 3/2011 | Russ et al. | |
| 2011/0082356 A1 | 4/2011 | Yang et al. | |
| 2011/0092927 A1 * | 4/2011 | Wilkes | A61F 13/00059 604/304 |
| 2011/0105854 A1 | 5/2011 | Kiani et al. | |
| 2011/0140703 A1 | 6/2011 | Chiao et al. | |
| 2011/0160548 A1 | 6/2011 | Forster | |
| 2011/0172582 A1 * | 7/2011 | Darian | A61F 15/004 602/79 |
| 2011/0178375 A1 | 7/2011 | Forster | |
| 2011/0213559 A1 | 9/2011 | Pollack et al. | |
| 2012/0010099 A1 | 1/2012 | Stephens et al. | |
| 2012/0016322 A1 * | 1/2012 | Coulthard | A61F 13/0216 604/319 |
| 2012/0035560 A1 | 2/2012 | Eddy et al. | |
| 2012/0078157 A1 * | 3/2012 | Ravikumar | A61F 5/34 602/79 |
| 2012/0109034 A1 * | 5/2012 | Locke | A61F 13/02 602/42 |

(56) References Cited

U.S. PATENT DOCUMENTS

| | | | |
|---|---|---|---|
| 2012/0130325 A1* | 5/2012 | Blott | A61M 1/0001 604/319 |
| 2012/0238931 A1 | 9/2012 | Rastegar et al. | |
| 2012/0245540 A1* | 9/2012 | Zimnitsky | A61K 31/385 604/319 |
| 2013/0053799 A1* | 2/2013 | Locke | A61F 13/00055 604/319 |
| 2013/0261409 A1 | 10/2013 | Pathak et al. | |
| 2013/0304006 A1 | 11/2013 | Toth | |
| 2013/0304007 A1* | 11/2013 | Toth | A61M 1/0031 604/321 |
| 2013/0317405 A1* | 11/2013 | Ha | A61F 13/0226 602/42 |
| 2013/0317406 A1* | 11/2013 | Locke | A61F 13/022 602/46 |
| 2015/0208961 A1 | 7/2015 | Duesterhoft et al. | |
| 2015/0290045 A1 | 10/2015 | Fan et al. | |

FOREIGN PATENT DOCUMENTS

| | | |
|---|---|---|
| WO | WO 03/040406 A2 | 5/2003 |
| WO | WO 2005/009328 A1 | 2/2005 |
| WO | WO 2007/130239 A1 | 11/2007 |
| WO | WO 2012/057882 A1 | 5/2012 |

OTHER PUBLICATIONS

U.S. Appl. No. 14/252,049, Allin et al.
DeHennis et al.; "A Wireless Microsystem for the Remote Sensing of Pressure, Temperature, and Relative Humidity"; Journal of Microelectromechanical Systems; Feb. 2005; pp. 12-22; vol. 14, No. 1; IEEE.
Mehmood et al.; "Applications of modern sensors and wireless technology in effective wound management"; Journal of Biomedical Materials Research B: Applied Biomaterials; bearing a date of Sep. 27, 2013; pp. 1-11; Wiley Periodicals, Inc.
U.S. Appl. No. 14/719,639, Duesterhoft et al.
PCT International Search Report; International App. No. PCT/US13/36000; dated Jul. 5, 2013; pp. 1-3.
PCT International Search Report; International App. No. PCT/US2013/035993; dated Jun. 25, 2013; pp. 1-2.
European Search Report; European App. No. EP 13 77 5331; dated Nov. 6, 2015; pp. 1-3.
European Search Report; European App. No. EP 13 77 5973; dated Nov. 4, 2015; pp. 1-3.
U.S. Appl. No. 13/491,677, Duesterhoft et al.
U.S. Appl. No. 13/455,220, Duesterhoft et al.
U.S. Appl. No. 13/445,174, Duesterhoft et al.
Abhisam; "RFID systems for pharmaceutical distributors to meet the new FDA regulations on drugs"; Discover the power of e-learning!; bearing a date of 2006; pp. 1-7; Abhisam Software.
Alien Technology; "Battery Assisted Passive Tags"; Alien Technology brochure; downloaded from the web Oct. 17, 2011; pp. 1-2; located at: http://www.alientechnology.com/docs/AT_DS_BAP.pdf ; Alien Technology Corp.
Berggren et al.; "Capacitive Biosensors"; Electroanalysis; bearing a date of 2001; pp. 173-180; vol. 13, No. 3; Wiley-VCH Verlag GmbH.
Bluestein et al.; "Pressure Ulcers: Prevention, Evaluation, and Management"; American Family Physician; Nov. 15, 2008; pp. 1186-1194; vol. 78, No. 10; American Academy of Family Physicians.
"Body-fluid battery"; Science News; Sep. 10, 2005; pp. 1-2; located at http://findarticles.com/p/articles/mi_m1200/is_11_168/ai_n15674798/; Science Service, Inc. and Gale Group.
Chawla et al.; "An Overview of Passive RFID"; IEEE Applications & Practice; Sep. 2007; pp. 11-17; IEEE.
Chen et al.; "A 2G-RFID-Based E-Healthcare System"; IEEE Wireless Communications; Feb. 2010; pp. 37-43; IEEE.
Chen et al.; "Ultrasonic Measurement System with Infrared Communication Technology"; Journal of Computers; Nov. 2011; pp. 2468-2475; vol. 6, No. 11; Academy Publisher.
Clay, Karen S.; "Preventing pressure ulcers in your facility: Karen S. Clay, RN, BSN, CWCN, presents a primer on how to protect frail residents—and avoid costly reprimands"; 2004; 14 pages; HCPro, Inc.
Collier, Mark; "Recognition and management of wound infections"; World Wide Wounds; Jan. 2004; pp. 1-9.
Cui et al.; "Nanowire Nanosensors for Highly Sensitive and Selective Detection of Biological and Chemical Species"; Science; Aug. 17, 2001; pp. 1289-1292, and 1 cover page; vol. 293; American Association for the Advancement of Science.
Cutting et al.; "Criteria for identifying wound infection"; Journal of Wound Care; Jun. 1994; pp. 198-201; vol. 3, No. 4.
Dowd et al.; "Survey of bacterial diversity in chronic wounds using Pyrosequencing, DGGE, and full ribosome shotgun sequencing"; BMC Microbiology; 2008; pp. 1-15; vol. 8, No. 43; BioMed Central Ltd.
Fadlullah et al; "Indoor High-Bandwidth Optical Wireless Links for Sensor Networks"; Journal of Lightwave Technology; Nov. 1, 2010; pp. 3086-3094; vol. 28, No. 21; IEEE.
Finkenzeller, Klaus; "Fundamental Operating Principles" Chapter 3 of the RFID Handbook: Fundamentals and Applications in Contactless Smart Cards and Identification; bearing a date of 2003; pp. 29-59; John Wiley & Sons, Ltd.
Fisher et al.; "Tracking the social dimensions of RFID systems in hospitals"; International Journal of Medical Informatics; bearing a date of 2008; pp. 176-183; vol. 77; Elsevier Ireland Ltd.
Fisher, Jill A.; "Indoor Positioning and Digital Management: Emerging Surveillance Regimes in Hospitals"; Chapter 5 in T. Monahan (Ed), Surveillance and Security: Technological Politics and Power in Everyday Life; May 23, 2006; pp. 77-88; Routledge.
Frost & Sullivan; "Advances in Wound Healing Techniques"; Technical Insights; Publication D11A; bearing a date of 2008; pp. 1-118; Frost & Sullivan.
Frost & Sullivan; "An Overview of Ulceration Wounds"; Publication M4BB-54; Dec. 2009; pp. 1-77; Frost & Sullivan.
Frost & Sullivan; "U.S. Advanced Wound Care Market"; Publication N71A-54; Aug. 2010; pp. 1-90; Frost & Sullivan.
Goodisman, Jerry; "Observations on Lemon Cells"; Journal of Chemical Education; Apr. 2001; pp. 516-518; vol. 78, No. 4.
Gray, David; "Assessment, Diagnosis and Treatment of Infection"; Wounds UK; bearing a date of 2011; pp. 4-9; vol. 7, No. 2, supplement.
Grist et al.; "Optical Oxygen Sensors for Applications in Microfluidic Cell Culture"; Sensors; 2010; pp. 9286-9316; vol. 10; MDPI; Basel, Switzerland.
Huang et al.; "Development of an $IrO_x$ Micro pH Sensor Array on Flexible Polymer Substrate"; Nanosensors and Microsensors for Bio-Systems 2008, edited by Vijay K. Varadan, Proc. of SPIE, vol. 6931, 693104; 2008; pp. 1-9.
Huang et al.; "Investigation of Repeatability of Sol-Gel Iridium Oxide pH Sensor on Flexible Substrate"; Micro- and Nanotechnology: Materials, Processes, Packaging, and Systems IV, edited by Jung-Chih Chiao et al., Proc. of SPIE, vol. 7269, 726916; 2008; pp. 1-9.
Ibridge Network; "pH Sensor Array on Flexible Substrate for Wound Care (UTA Ref. No. 08-21)"; Nov. 28, 2011; pp. 1-2; Kauffman Innovation Network, Inc.
Intel; "WISP: Wireless Identification and Sensing Platform"; Intel Labs Seattle; printed on Oct. 8, 2011; pp. 1-4; located at http://www.seattle.intel-research.net/WISP/.
Intelleflex; "Worldwide RFID UHF Map"; printed on Oct. 17, 2011; p. 1; located at: http://www.intelleflex.com/pdf/Worldwide_UHF_Chart.pdf ; Intelleflex Corporation.
Karthik MNS; "Could blood be used to power batteries?"; Feb. 2009; pp. 1-4; located at: http://hoowstuffworks.blogspot.com/2009/02/could-blood-be-used-to-power-batteries.html.
Kavehrad, Mohsen; "Sustainable Energy-Efficient Wireless Applications Using Light"; IEEE Communications Magazine; Dec. 2010; pp. 66-73; IEEE.

(56) References Cited

OTHER PUBLICATIONS

Kelly-Quintos et al.; "Characterization of the Opsonic and Protective Activity Against *Staphylococcus aureus* of Fully Human Monoclonal Antibodies Specific for the Bacterial Surface Polysaccharide Poly-N-Acetylglucosamine"; Infection and Immunity; May 2006; pp. 2742-2750; vol. 74, No. 5; American Society for Microbiology.
Lee et al.; "Water Activated Disposable and Long Shelf Life Microbatteries"; 2003; pp. 387-390; IEEE.
Lim et al.; "A Micromechanical Biosensor with Interdigitated Capacitor Readout"; Proceedings of the 2011 IEEE/ICME International Conference on Complex Medical Engineering; May 22-25, 2011; pp. 42-46; IEEE.
Löfgren et al.; "Low-power humidity sensor for RFID applications"; Multi-Material Micro Manufacture; 2008; 4 pages; Cardiff University.
McColl et al.; "Monitoring moisture without disturbing the wound dressing"; Wounds UK; bearing a date of 2009; pp. 94-96, and 98-99; vol. 5, No. 3.
Murata Manufacturing Co., Ltd.; "Piezoelectric Sound Components"; Cat. No. P37E-23; Nov. 2009; pp. 1-33, and two cover pages.
Murata Manufacturing Co., Ltd.; "Ultrasonic Sensor Application Manual"; Cat. No. S15E-5; Aug. 2009; pp. 1-3, and 2-14, and one supplemental page.
Nature News; "A miniature biofuel cell operating in a physiological buffer"; Nature; Nov. 12, 2002; pp. 1-2; located at http://www.nature.com/news/2002/021112/full/news021111-1.html.
Ohno et al.; "Graphene Field-Effect Transistors for Label-Free Biological Sensors"; IEEE Sensors 2010 Conference Proceedings; Nov. 1-4, 2010; pp. 903-906; IEEE.
Pacific Northwest National Laboratory; "Juvenile Salmon Acoustic Telemetry System (JSATS) Acoustic Transmitters"; Mar. 2010; pp. 1-2.
Pan et al.; "Development of the real-time pH sensing system for array sensors"; Sensors and Actuators B 108; 2005; pp. 870-876; Elsevier B.V.
Patauner et al.; "High Speed RFID/NFC at the Frequency of 13.56 MHz"; presented at the First International EURASIP Workshop on RFID Technology; Sep. 24-25, 2007; pp. 1-4.
Pushparaj et al.; "Flexible energy storage devices based on nanocomposite paper"; PNAS; Aug. 21, 2007; pp. 13574-13577; vol. 104, No. 34; The National Academy of Sciences of the USA.
Ruhanen et al.; "Sensor-enabled RFID tag handbook"; Building Radio Frequency Identification for the Global Environment; Jan. 2008; pp. 1-47; IST-2005-033546; European Commission.
Sammoura et al.; "Water-activated disposable and long shelf life microbatteries"; Sensors and Actuators A 111; 2004; pp. 79-86; Elsevier B.V.
Sample et al.; "A Capacitive Touch Interface for Passive RFID Tags"; IEEE International Conference on RFID; Apr. 27-28, 2009; pp. 103-109; IEEE.
Sample et al.; "Design of an RFID-Based Battery-Free Programmable Sensing Platform"; IEEE Transactions on Instrumentation and Measurement; Nov. 2008; pp. 2608-2615; vol. 57, No. 11; IEEE.
Sample et al.; "Photovoltaic Enhanced UHF RFID Tag Antennas for Dual Purpose Energy Harvesting"; 2011 International Conference on RFID; Apr. 12-14, 2011; pp. 146-153; IEEE.
Sidén et al.; "The 'Smart' Diaper Moisture Detection System"; IEEE MTT-S Digest, WE4B-3; 2004; pp. 659-662; IEEE.
Stevens et al.; "RuBee (IEEE 1902.1)—The Physics Behind, Real-Time, High Security Wireless Asset Visibility Networks in Harsh Environments"; Sep. 2010; retrieved from web Nov. 17, 2011; pp. 1-6; located at: http://www.rubee.com/White-SEC/RuBee-Security-080610.pdf.
Tehrani et al.; "Detection of Monoclonal Antibodies using Chemically Modified Graphite Substrates"; IEEE Sensors 2010 Conference Proceedings; Nov. 1-4, 2010; pp. 428-431; IEEE.
University of Texas Arlington, Office of Technology Management; "Smart Wound Condition Monitoring pH Sensor Array on Flexible Substrate"; Technology Summary; printed on Apr. 12, 2012; pp. 1-2.
Visible Assets; "RuBee Technology, Real-Time Asset Visibility"; printed from web Nov. 17, 2011; pp. 1-3; located at: http://www.rubee.com/Techno/index.html ; Visible Assets.
Wang, Wencheng; "A Design Method of Ultrasonic Ranging System with High Accuracy"; Journal of Computational Information Systems; Jul. 2011; pp. 2444-2451; vol. 7, No. 7; Binary Information Press.
Yeager et al.; "Wirelessly-Charged UHF Tags for Sensor Data Collection"; 2008 IEEE International Conference on RFID; Apr. 16-17, 2008; pp. 320-327; IEEE.
European Patent Office; Communication pursuant to Article 94(3) EPC; App. No. EP 13 775 331.5; dated Feb. 15, 2017; pp. 1-4.
European Patent Office; Communication pursuant to Article 94(3) EPC; App. No. EP 13 775 973.4; dated Feb. 14, 2017; pp. 1-4.

* cited by examiner

APPURTENANCES TO CAVITY WOUND DRESSINGS

PRIORITY APPLICATIONS

For purposes of the USPTO extra-statutory requirements, the present application constitutes a continuation-in-part of U.S. patent application Ser. No. 13/445,174, entitled APPURTENANCES FOR REPORTING INFORMATION REGARDING WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012, which is currently co-pending or is an application of which a currently co-pending application is entitled to the benefit of the filing date, and which is a continuation-in-part of U.S. patent application Ser. No. 13/445,220, entitled COMPUTATIONAL METHODS AND SYSTEMS FOR REPORTING INFORMATION REGARDING APPURTENANCES TO WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012.

Related Applications

U.S. patent application Ser. No. 13/491,677, entitled DORMANT TO ACTIVE APPURTENANCES FOR REPORTING INFORMATION REGARDING WOUND DRESSINGS, naming Paul Duesterhoft, Nicholas Dykstra, Daniel Hawkins, Roderick A. Hyde, Jordin T. Kare, Mark K. Kuiper, Eric C. Leuthardt, Nels R. Peterson, Elizabeth L. Schubert, Clarence T. Tegreene, and Lowell L. Wood, Jr. as inventors, filed 8 Jun. 2012, is related to the present application.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

SUMMARY

In some embodiments, an appurtenance to a cavity wound dressing includes: a substrate including at least one wound-facing surface, the wound-facing surface configured to be oriented facing a wound surface of a cavity wound; and a plurality of sensor units attached to the substrate, the plurality of sensor units oriented and positioned on the substrate relative to the wound surface of the cavity wound. In some embodiments, an appurtenance to a cavity wound dressing includes: a plurality of sensor units, wherein each sensor unit includes an attachment region configured to affix to a porous wound dressing material and wherein each sensor unit is configured to be operational when in contact with fluid, is configured to be operational at temperatures between 35 degrees Centigrade and 40 degrees Centigrade, and under physical pressure up to 32 mm Hg; and the plurality of sensor units in the aggregate of a size and mass to allow for medical use with the porous dressing material at the cavity wound. In some embodiments, an appurtenance to a cavity wound dressing includes: a substrate including at least one wound-facing surface, the wound-facing surface of a size and shape for positioning within a cavity wound, wherein the substrate includes a plurality of apertures; and a plurality of sensor units attached to the substrate, each of the plurality of sensor units oriented and positioned on the substrate relative to at least one of the plurality of apertures.

In some embodiments, an appurtenance to a cavity wound dressing includes: a substrate configured to associate with a cavity wound dressing; a transmission unit attached to a surface of the substrate, the transmission unit including circuitry and at least one antenna operably attached to the circuitry; a selectively actuatable switch operably connected to the transmission unit; and one or more sensor units affixed to the substrate and operably connected to the selectively actuatable switch. In some embodiments, an appurtenance to a cavity wound dressing includes: a substrate configured to fit substantially within a cavity wound in association with a wound dressing; and a plurality of sensor units attached to the substrate, each of the sensor units including a detector and an indicator, wherein the indicator includes a passive radio frequency identification (RFID) unit.

A system for monitoring a cavity wound medical dressing includes at least one appurtenance to a cavity wound dressing and at least one external device. For example, some embodiments include an appurtenance to a cavity wound dressing, the appurtenance including a substrate and a plurality of sensor units, wherein each of the sensor units include an indicator configured to respond to a specific external signal; and an external device configured to transmit the specific external signal and detect the response of the indicator included with each of the plurality of sensor units. Some embodiments include a local unit configured to transmit signals to an appurtenance and receive signals from the appurtenance. Some embodiments include at least one central assembly configured to communicate with at least one local device.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
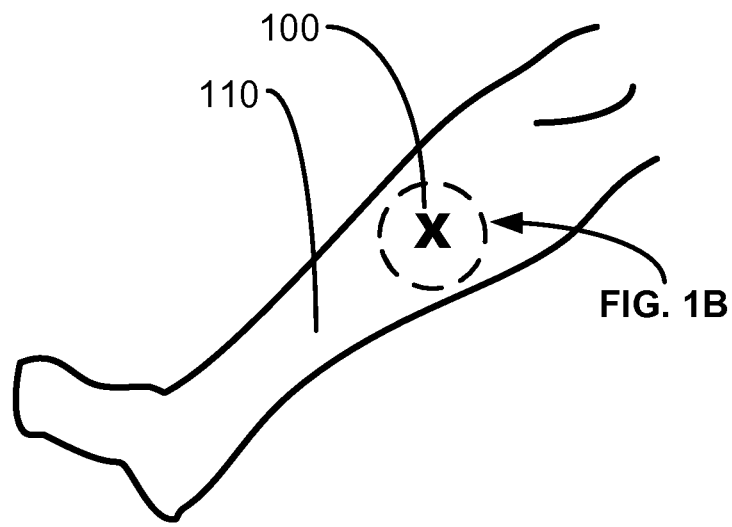
FIG. 1A illustrates a wound region on a human body part.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The use of the same symbols in different drawings typically indicates similar or identical items.

With reference now to FIG. 1A, illustrated is a body part 110 that is a human leg. The body part 110 includes a wound region, denoted by the dotted circle. The wound region includes a cavity wound 100, denoted by the X marking in FIG. 1A.

A "cavity wound," as used herein, denotes a wound that penetrates into body tissue and is of a size and shape to create a cavity or space in the tissue with an open region at the normal tissue surface. A cavity wound includes a loss of continuity of the skin with associated tissue loss. A cavity wound involves the dermal skin layer, and can, in some circumstances, extend into sub-dermal layers of skin to expose underlying tissues, such as tendon, muscle and bone. For example, a cavity wound can include an edge region at the skin level of an individual and penetrate into the adjacent skin and tissue layers, with the wound forming a cavity adjacent to the normal skin level. A cavity wound can be created by traumatic injury, such as a puncture of the skin and tissue. For example, a cavity wound can be created by an open reduction of fracture. A cavity wound can be formed from a severe burn, such as a third degree burn. A cavity wound can be formed by surgical intervention, for example to remove a tumor or other tissue mass, such as an area of infected tissue. A cavity wound can be partially formed or enlarged by debridement of a wound by surgical or chemical means. A cavity wound can be formed by tissue atrophy or necrosis at a site of low blood flow in the tissue. For example, a cavity wound can develop from a pressure ulcer, decubitus ulcer or bedsore that increases in severity due to a lack of blood flow to a region due to physical pressure on the circulatory system in the tissue and shear stress on the tissue structure. For example, a cavity wound can develop from a diabetic ulcer, a venous ulcer, or an arterial ulcer. For example, a cavity wound can develop from a stage 2-4 pressure ulcer. For example, a cavity wound can develop from necrotizing fasciitis. A cavity wound can arise from a wound closing by secondary or tertiary intention. A cavity wound can be a "chronic wound," or a persistent wound that resists healing over a normal time frame. A cavity wound can form from a non-healing surgical wound. A cavity wound can heal normally, such as with granulation of the wound bed over a clinically-expected time frame.

The temperature adjacent to the wound bed of a cavity wound depends on the physiological conditions of the cavity wound, including wound location, position and depth, regional blood flow, inflammation, and immune system response. In some patients, for example, the temperature within the cavity of a cavity wound can be in a range between 35 degrees Centigrade and 40 degrees Centigrade. Temperatures below 35 degrees Centigrade and above 40 degrees Centigrade can indicate a medical situation relative to the cavity wound. For example, a temperature of approximately 30 degrees Centigrade within a cavity wound can indicate insufficient blood flow to the adjacent tissue, or excessive necrotic tissue within the cavity wound. For example, a temperature above approximately 40 degrees Centigrade can indicate a localized immune response, and therefore, an infection within the cavity wound region. A change in temperature over time within a cavity wound can indicate the deterioration or improvement of the medical situation of the cavity wound.

Physical pressure on a wound surface of a cavity wound can have negative effects on a cavity wound, including physical shear of the wound surface and compression of blood vessels in the periwound region. The specific physical pressure that can be acceptable for a patient in a cavity wound depends on a number of factors, including wound size, location, patient health and secondary factors, such as additional wounds or medical conditions. As an example, the minimal physical pressures required to close a capillary range from 12 to 32 mm Hg. See: Clay, "Preventing Pressure Ulcers in your Facility: Karen S. Clay, RN, BSN, CWCN, Presents a Primer on How to Protect Frail Residents—and Avoid Costly Reprimands," HCPro, Inc., (2004) (downloaded on Dec. 6, 2012); and Bluestein and Javaheri, "Pressure Ulcers: Prevention, Evaluation, and Management," *American Family Physician* 78(10):1186-1196 (2008), which are each incorporated herein by reference. Generally, medical intervention for cavity wounds includes physical pressures of less force than would be expected to close an adjacent capillary. For example, in some situations a medical intervention, such as a wound dressing, would be preferred by a caregiver that is predicted to press with a force of less than 32 mm Hg at the wound surface during use with the cavity wound, in order to maximize blood flow in the region and to promote healing of the cavity wound. For example, in some situations a medical intervention, such as a wound dressing, would be preferred by a caregiver that is predicted to press with a force of less than 20 mm Hg at the wound surface during use with the cavity wound, particularly in medical situations wherein the wound surface is considered to be sensitive or fragile (e.g. directly after surgery or injury). For example, in some situations a medical intervention, such as a wound dressing, would be preferred by a caregiver that is predicted to press with a force of less than 12 mm Hg at the wound surface during use with the cavity wound, for example with wounds that are considered to be particularly high risk due to ongoing lack of healing, or the patient's overall medical status.

A cavity wound has a "periwound" region, which refers to the tissue in a region adjacent to the cavity wound. For example, the periwound region refers to the tissue area directly adjacent to the cavity wound. Tissue in the periwound region can be affected by the cavity wound, for example through inflammation, swelling, infection, low oxygen perfusion, or wound-associated trauma (e.g. bruising). In some situations, the periwound region includes wound exudate, or wound fluid arising from the cavity wound.

Cavity wounds such as described herein are usually clinically resolved by secondary intention or tertiary intention. Clinical protocols for the healing of cavity wounds can include leaving the cavity space open or uncompressed, with the addition of a wound dressing that fully or partially fills the cavity space, minimizes potential exposure of the wound surface to external debris, and reduces potential dryness at the wound surface. A cavity wound dressing can also be configured to absorb excess exudate from the wound region. Primary and secondary dressings on cavity wounds are designed to be put in place for a limited time period, such as hours or days, and then replaced. For example, depending on the clinical situation, a cavity wound primary and secondary dressing can be intended for replacement every 6 hours, every 12 hours, every 24 hours, daily, every 2 days, every 3 days, every 4 days, every 5 days, every 6 days, or every week. As an example, some cavity wounds are filled with saline-soaked gauze bandages as a primary dressing, and then covered with an adhesive cover over the wound region as a secondary dressing. The saline-soaked gauze bandages are then removed and replaced on a regular schedule, such as every day, every 2 days, or every 3 days, every 4 days, every 5 days, every 6 days, or every week. In some situations, cavity wound dressings include alginate dressings, such as Sorbsan® and Kaltostat® wound dressings. In some situations, cavity wound dressings include foam-based dressings, such as Cavi-Caret, Allevyn® Plus Cavity and PolyMem® Wic® wound dressings. Cavity wound dressings can also include gel or alginate based dressings for topical application to the wound surface.

Cavity wound dressings such as those described herein are generally used for a relatively short period of time, on the order of hours or days. Solid wound dressings can be removed and disposed of after use. An appurtenance configured for use with a cavity wound dressing, such as those described herein, is configured for use over the course of hours or days and then removed and disposed of using standard methods. A cavity wound dressing and an associated appurtenance are generally single use and disposable after use. For example, a caregiver can require a new cavity wound dressing every 24 hours (1 day) for an acute wound. Any cavity wound primary and secondary dressing utilized in this type of situation would, consequently, be of a size and shape to remain within the wound cavity and affixed to the periwound region over the course of at least a 24 hour period and then removed for disposal. An appurtenance to a cavity wound dressing intended for use over the course of a 24 hour time period should similarly be of a size, shape, material fabrication, and capabilities to function while affixed to or used in conjunction with the cavity wound dressing over the 24 hour period that the dressing is in use. As an additional example, a caregiver can decide that for another type of cavity wound, such as a chronic wound, the cavity wound dressing needs to be removed and replaced, once every 3 days, or every 4 days, or every 5 days, or every 6 days, or every 7 days. Correspondingly, an appurtenance affixed to or used in conjunction with a cavity wound dressing intended for use over the course of at least 3 to 7 days should be of a size, shape, material fabrication, flexibility, mass and capabilities to function while associated with the cavity wound dressing over at least the 3 to 7 day period that the dressing is in use. In embodiments wherein an appurtenance is intended for reuse, such as reuse with a second or subsequent cavity wound dressing used over a wound, the appurtenance should be of a size, shape, material fabrication, flexibility, mass and capabilities to function during the entire intended use, including the time period of removal from a first cavity wound dressing and application with a second cavity wound dressing. An appurtenance is durable for the intended time and conditions of use. An appurtenance is fabricated to retain its structural integrity and not chip, split, peel or fragment while in use within the cavity wound.

A caregiver can utilize some embodiments of the appurtenances and related systems described herein in relation with multiple types of cavity wound dressings. As used herein, a caregiver includes at least one of a patient, a personal caregiver, a healthcare provider, and medical personnel. Appurtenances can be fabricated in shapes and sizes to conform to a variety of standard cavity wound dressing sizes, shapes and types. Appurtenances can be fabricated with, for example, transmission units, antennas and sensors appropriate for use with a variety of cavity wound dressings. Appurtenances can be fabricated with, for example, transmission units, antennas and sensors appropriate for different medical situations and monitoring requirements. While it is envisioned that every appurtenance will not be appropriate for use with every cavity wound dressing (for example due to size, shape or material compatibility), a given appurtenance is expected to be suitable for use with a range of potential cavity wound dressings. For example, a given appurtenance of a specific size, shape and fabrication, including type of sensor unit(s), should be suitable for use with a variety of cavity wound dressings of conforming sizes, shapes and types. Generally, any specific appurtenance embodiment is not expected to only conform to use with a unique cavity wound dressing of a specific size, shape and type. Instead, it is expected that a specific appurtenance embodiment will be suitable for use with a range of cavity wound dressings. Similarly, it is expected that a specific appurtenance embodiment will be suitable for use with a range of cavity wound and cavity wound dressing monitoring requirements.

Figure 1B:
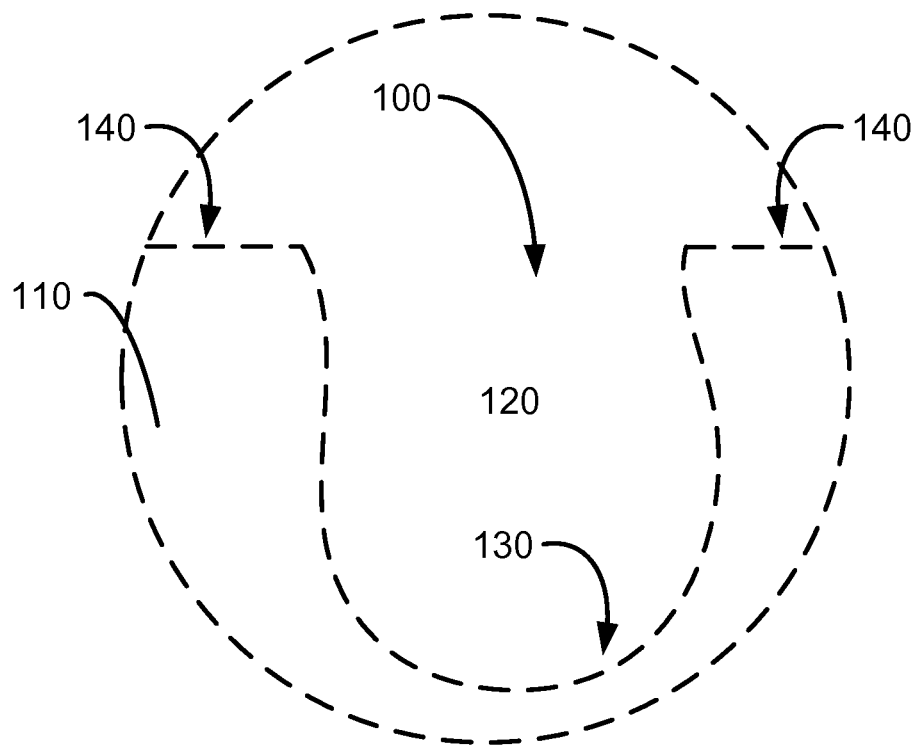
FIG. 1B depicts, in cross-section, a cavity wound in the wound region shown in FIG. 1A.

In reference now to FIG. 1B, illustrated is a cross-section view through a wound region including a cavity wound 100. The cavity wound 100 is within the body part 110, such as illustrated with an external view in FIG. 1A. The cavity wound 100 shown in FIG. 1B is depicted as a substantially oval cavity for purposes of illustration, however actual cavity wound sizes and shapes will vary. The cavity wound 100 includes a cavity 120 or space in the tissue of the body part 110. The cavity wound 100 also includes a wound surface 130 which encompasses the tissue surface of the wound 100 facing the cavity 120. The wound 100 can be a partial or full thickness wound. Depending on the depth and location of a cavity wound 100 on a body part 110, a cavity 120 can extend into multiple layers of tissue, and potentially through different types of tissue. For example, a cavity 120 of a pressure ulcer wound can extend through epithelial layers, a muscular layer, and to a bone surface. For example, a stage four pressure ulcer can extend to the bone. Correspondingly, a wound surface 130 includes tissues representative of the respective layers that the cavity 120 extends through. A cavity wound 100 healing by secondary intention is likely to granulate from the wound surface 130 inward, such as from the deepest cavity level to the surface level, with a corresponding decrease in size of the cavity 120 over time. A cavity wound 100 has a surface region 140 of the periwound region. For example, the surface region 140 of the periwound region can include the external skin level adjacent to the cavity wound 100. During treatment, a wound dressing cover can be adhered to the surface region 140 of the periwound region of the cavity wound 100.

Figure 2A:
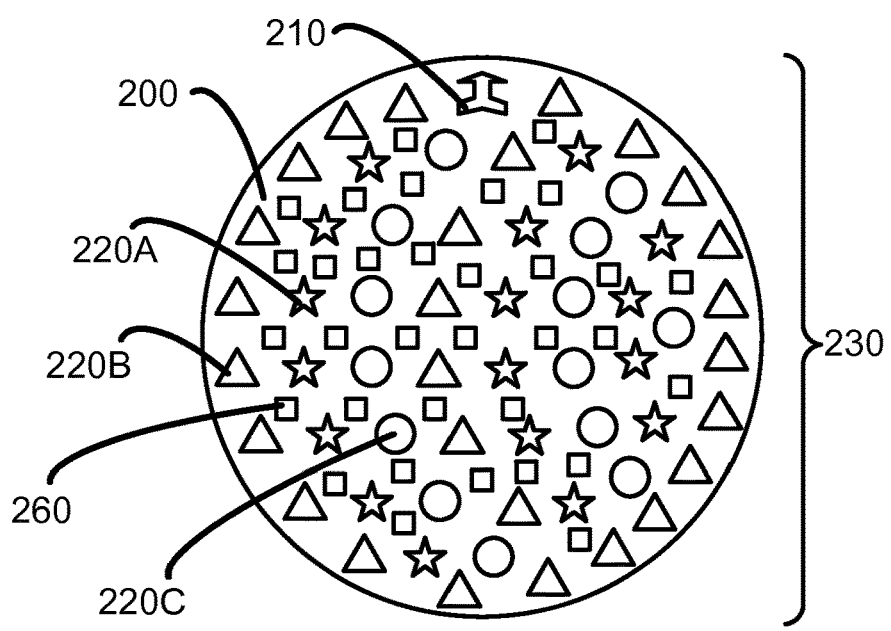
FIG. 2A shows an appurtenance to a cavity wound dressing.

FIG. 2A depicts an appurtenance 230 to a cavity wound dressing. The appurtenance 230 to a cavity wound dressing shown in FIG. 2A is a substantially planar, disk-like structure. The appurtenance 230 is separate and distinct from a cavity wound dressing, but intended for functional use with a primary, and in some embodiments, a secondary wound dressing for a cavity wound. The appurtenance 230 embodiment illustrated in FIG. 2A is intended for use in combination with a cavity wound dressing, and not intended for use without a wound dressing. In some embodiments, an appurtenance 230 can be attached to a dressing for a cavity wound. For example, the appurtenance 230 can be attached to a dressing for a cavity wound with a chemical attachment, such as a pressure-sensitive adhesive, a contact adhesive, or a quick-drying adhesive. For example, the appurtenance 230 can be attached to a dressing for a cavity wound with a mechanical attachment. For example, a mechanical attachment can include attachments shaped like prongs, barbs, bristles, spikes, or spurs on a cavity-facing surface of the appurtenance 230. In some embodiments, an appurtenance 230 can be stabilized relative to a dressing for a cavity wound. For example, an appurtenance can be tethered or affixed to a cavity wound dressing in a manner sufficient to stabilize the appurtenance 230-wound dressing combination. In some embodiments, an appurtenance 230 can be configured for use in conjunction with, but not attached to, a cavity wound primary or secondary dressing. An appurtenance 230, like a cavity wound primary dressing, can be of different sizes and shapes corresponding to use in different size and shape cavity wounds.

The appurtenance 230 illustrated in FIG. 2A includes a substantially planar, disk-like substrate 200. A substrate 200 such as illustrated in FIG. 2A includes a wound-facing surface, the wound-facing surface configured to be oriented facing a wound surface of a cavity wound. Correspondingly, a substrate 200 such as illustrated in FIG. 2A includes a cavity-facing surface, the cavity-facing surface configured to be oriented toward the internal cavity region of a cavity wound. In some embodiments, a substrate 200 includes at least one cavity-facing surface of the substrate configured to be oriented facing the cavity region of the cavity wound, wherein the cavity-facing surface is positioned opposing the at least one wound-facing surface. For purposes of illustration in FIG. 2A, a single side of the planar surface is shown. In embodiments such as illustrated in FIG. 2A, an appurtenance 230 is a substantially planar, flexible structure. For example, in some embodiments, an appurtenance 230 includes a substrate 200 that is a substantially pliable and fluid-permeable structure. For example, an appurtenance 230 can include a substrate 200 that is a thin planar structure including a series of apertures 260 through the depth of the plane. As depicted in FIG. 2, in some embodiments a series of apertures 260 can be positioned at specific locations relative to the surface of the plane. In some embodiments, a series of apertures can be integral to the structure of the substrate 200. In some embodiments, an appurtenance 230 can include a substrate 200 that is a mesh structure. For example, a substrate 200 of an appurtenance 230 can include a gauze mesh structure, a woven fabric structure, a foam mesh structure or a plastic mesh structure. A substrate 200 of an appurtenance 230 can be fabricated from a number of flexible, pliable materials of sufficient strength to stably affix a series of sensor units 220. For example, in some embodiments, a substrate 200 of an appurtenance 230 to a cavity wound 100 can be fabricated from gauze or similar bandage materials, silicone, latex, foam, flexible plastic or woven materials. For example, in some embodiments, a substrate 200 of an appurtenance 230 to a cavity wound 100 can be fabricated from woven or non-woven material, film, foam, or alginate composite. In some embodiments, a substrate 200 of an appurtenance 230 is fabricated from a composite material, or a combination of materials. A substrate 200 can be fabricated from a bio-compatible material, so as to minimize inflammation and other secondary effects of the appurtenance 230. The substrate 200 is fabricated from materials that are durable under the conditions within a cavity wound 100. For example, the substrate 200 should be durable under physiological temperatures and pressures of a cavity wound 100. For example, the substrate 200 should be durable in the presence of wound exudate. In some embodiments, a substrate 200 of an appurtenance 230 to a cavity wound 100 includes a substantially flexible, fluid-permeable planar structure of no more than 5 millimeters (mm) in thickness. In some embodiments, a substrate 200 of an appurtenance 230 to a cavity wound 100 includes a substantially flexible, fluid-permeable planar structure of no more than 10 mm in thickness. In some embodiments, a substrate 200 of an appurtenance 230 to a cavity wound 100 includes a substantially flexible, fluid-permeable planar structure of no more than 15 mm in thickness. In some embodiments, a substrate 200 of an appurtenance 230 to a cavity wound 100 includes a substantially flexible, fluid-permeable planar structure of no more than 20 mm in thickness. In some embodiments, a substrate 200 of an appurtenance 230 to a cavity wound 100 includes a substantially flexible, fluid-permeable planar structure of no more than 25 mm in thickness.

In some embodiments, the appurtenance includes a porous substrate that is configured to be utilized in association with a cavity wound primary dressing. The substrate is configured as a support for a plurality of sensor units. In some embodiments, the substrate is configured to irreversibly attach directly to an external surface of the wound dressing. In some embodiments, the substrate includes an adhesive on a surface conforming to an external surface of the wound dressing. For example, the surface conforming to an external surface of the wound dressing can include a glue, epoxy, sealant, mucilage, paste or other binder material. For example, the surface conforming to an external surface of the wound dressing can include a series of projections of a size, shape and orientation to affix the surface conforming to an external surface of the wound dressing and the external surface of the wound dressing to each other. In some embodiments, the surface of the substrate conforming to an external surface of the wound dressing can include an adhesive covered by a removable protective sheet, the sheet configured for detachment and exposure of the adhesive when the appurtenance is attached to the wound dressing. In some embodiments, the surface of the substrate of the appurtenance configured to conform with a surface of the wound dressing can include barbs, hooks, pins, prongs or other extensions configured to adhere or fix into the outer surface of the wound dressing. In some embodiments, a surface of the substrate of the appurtenance configured to conform with an outer surface of a wound dressing can include a mixture or combination of any of the above.

In some embodiments, the substrate includes a flexible material. For example, the substrate can include a pliable plastic, a woven fabric material, foam, soft mesh or other flexible material. In some embodiments, the substrate includes a rigid material. For example, the substrate can include at least one rigid plastic material in a location configured to provide support for a portion of the appurtenance, such an edge region of the appurtenance. For example, the substrate can include at least one rigid plastic material at a location configured to attach a primary or secondary dressing, the rigid plastic configured to provide physical support for the attached dressing. In some embodiments, the substrate includes at least one bio-compatible material. For example, the substrate can include one or more bio-compatible plastic materials, one or more bio-compatible foam materials, one or more bio-compatible fabric materials, or one or more bio-compatible metals.

In some embodiments, an appurtenance 230 to a cavity wound dressing is substantially sterilized prior to use. For example, the appurtenance 230 can be treated with one or more chemical disinfectants or UV surface radiation for a period of time sufficient to substantially sterilize the appurtenance 230 prior to use. For example, the appurtenance 230 can be treated with one or more antimicrobial gasses, for example ethylene oxide (ETO), prior to use. For example, the appurtenance 230 can be treated with a chemical sterilizing agent, such as hydrogen peroxide in liquid or vapor form, prior to use. For example, the appurtenance 230 can be treated with steam as an anti-infective prior to use. In some embodiments, an appurtenance 230 to a cavity wound dressing includes a sterile wrapper. For example, an appurtenance 230 to a cavity wound dressing can be stored and/or transported within a sterile wrapper, such as a firm paper wrapper or a plastic film. A sterile wrapper configured for storage and/or transport of an appurtenance 230 can be treated to minimize contamination, for example coated with one or more anti-microbial agents. In some embodiments, the appurtenance 230 is substantially sterilized in combination with a wound dressing.

Also as illustrated in FIG. 2A, the appurtenance 230 includes an attached orientation indicator 210. In some embodiments, an orientation indicator 210 can be included to provide positional information regarding the appurtenance 230. For example, a positional indicator 210 can be placed at a particular side of the cavity wound 100 during use. An orientation indicator 210 can include, for example, a visual graphic. An orientation indicator 210 can include, for example, a visible electric light, such as an LED, powered by an attached battery. An orientation indicator 210 can include, for example, a visible chemiluminescent or thermoluminescent indicator. An orientation indicator 210 can include, for example, an electronically-readable tag or marker for electronic recordation of the appurtenance orientation in the cavity wound. An orientation indicator 210 can include, for example, an RFID. The appurtenance can also include an electronic identifier, for example a RFID with a specific identifier. An orientation indicator 210 can, for example, be visible and positioned adjacent to an edge region of an appurtenance 230 for visible orientation during use or placement of the appurtenance 230. An orientation indicator 210 can, for example, be positioned in a central region of an appurtenance 230 and configured to be detectable non-visually, such as by ultrasound or X-ray scans.

As shown in FIG. 2A, an appurtenance 230 includes a plurality of sensor units 220 attached to the substrate 200, the plurality of sensor units 220 oriented and positioned on the substrate 200 relative to the wound surface of the cavity wound. The plurality of sensor units 220 are configured to detect and report specific conditions at the wound-facing surface of the appurtenance. The term "sensor unit," as used herein, refers to a discrete unit of the appurtenance 230 that is configured to detect and indicate a condition within the wound cavity. In some embodiments, a sensor unit includes an enclosure, a detector, and an indicator. A sensor unit can be chemically-based. A sensor unit can be mechanically-based. A sensor unit can be electrically-based. A sensor unit can include circuitry. For example, a sensor unit can include a detector of a physical condition, such as physical pressure, temperature, or presence of a specific analyte in a wound cavity. For example, a sensor unit can include a detector of excess moisture. Some embodiments include sensor units configured to detect multiple physical conditions. Some embodiments include a sensor unit configured to detect both physical pressure and temperature over time. A sensor unit includes an indicator for the presence of the physical condition. For example, a sensor unit including a physical pressure detector can include a color indicator, wherein a stronger or more intense color in a particular visual region indicates that the sensor unit has been subject to physical pressure. For example, a sensor unit including a temperature detector can include a color indicator, wherein a stronger or more intense color in a particular visual region indicates that the sensor unit has been subject to an elevated temperature range. For example, a sensor unit including an analyte detector can include a color indicator, wherein a stronger or more intense color in a particular visual region indicates that the sensor unit has detected the presence of the analyte. See, for example: US Patent Application Publication No. 2007/0269851, "Colorimetric Substrates, Colorimetric Sensors, and Methods of Use," to Sanders et al.; and US Patent Application Publication No. 2009/0299161, "Marker of Wound Infection," to Cullen et al., which are each incorporated by reference herein. For example, a sensor unit can include a barrier layer that is broken down in response to proteins present in the wound fluid, releasing a color indicator, such as a dye. See US Patent Application Publication No. 2008/0166397, "Pain-Sensitive Therapeutic Wound Dressing," to Trotter and Culten, which is incorporated herein by reference. Some embodiments include a plurality of sensor units. In embodiments including at least two sensor units, the sensor units can include the same or different indicators.

In some embodiments, the indicator is not a visible indicator. For example, an indicator can include a physical change in at least one material, which can be detected with an external device. For example, an indicator can include chemically reactive materials configured to be released in the presence of an analyte, wherein the released material is detectable with an external device. For example, an indicator can include a material configured to release florescent material in the presence of an analyte. In some embodiments, the physical change in a material in the indicator is a change in conductance or frequency characteristics in the presence of an electromagnetic signal. For example, the indicator can include a RFID antenna with a frequency characteristic that is altered in the presence of a fluid, such as blood.

A variety of sensor units including different detectors can be utilized in different embodiments of the appurtenances, depending on factors such as the intended use of the appurtenance, size, weight, cost, bio-compatibility, safety and ease of disposal. Detectors can be of a variety of types depending on the embodiment. A sensor unit can include at least one detector responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, one or more detectors can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). Sensor units can also include detectors utilizing nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensor units can include detectors utilizing antibodies secured to a graphene substrate. See Tehrani et al., "Detection of Monoclonal Antibodies using Chemically Modified Graphite Substances," *IEEE Sensors* 2010 *Conference Proceedings*, 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors* 2010 *Conference Proceedings*, 903-906, (2010), which is incorporated herein by reference. A sensor unit in an appurtenance can interact with a sensor present in a wound dressing, for example as described in U.S. Pat. No. 6,283,938 to McConnell, titled "Medicating Bandage and Controllable Permeable Membrane," which is incorporated herein by reference. A sensor unit can include a field effect transistor (FET), such as described in U.S. Pat. No. 7,507,675 to Zuilhof et al., titled "Device Manufacturing Method and Device," which is incorporated herein by reference. A sensor unit can include a nano-cantilever device, such as described in U.S. Pat. No. 7,612,424 to Espinosa and Ke, titled "Nanoelectromechanical Bistable Cantilever Device," which is incorporated herein by reference. An appurtenance can include sensor units including test electrodes configured as an array. See U.S. Pat. No. 7,945,302 "Wound Mapping System," to McAdams, which is incorporated by reference.

Sensor units such as those described herein can be configured to detect fluids. Some embodiments include a sensor unit configured to detect an excess level of fluid at the sensor unit. Sensor units such as those described herein can be configured to detect one or more components of a fluid. Sensor units such as those described herein can be configured to detect one or more analytes within a fluid. As used herein, fluid includes both gasses and liquids individually or as mixtures. In some embodiments, sensor units described herein can detect fluids, whether in gaseous state or liquid state. If the fluid is a liquid, it can be drawn into an appurtenance, such as to a position adjacent to a sensor unit, through capillary action. If the fluid is a gas, it can be drawn into the appurtenance through gravity (i.e. where the appurtenance is oriented on the top of a wound surface within a cavity wound). In some embodiments, the appurtenance includes a micropump positioned to move fluids into an appurtenance substrate to a position adjacent to a sensor unit. In some embodiments, the sensor unit includes a sealed chamber that is under vacuum and connected to an aperture in the enclosure of the sensor unit. When the seal on the chamber is broken, fluid moves into the sensor unit in response to the low (or negative) air pressure in the tube. Some embodiments include an internal hydrophobic region positioned over an aperture in the sensor unit, wherein both a sufficient quantity and pressure of fluid adjacent to the sensor unit are required to overcome the hydrophobicity so that the fluid moves through the aperture and into the sensor unit for detection.

The appurtenance can include an energy storage unit. For example, an appurtenance can include an energy storage unit, such as a battery, operably attached to a processor and one or more sensor units. In some embodiments, the appurtenance does not store energy. The appurtenance can include an energy harvesting unit, such as a unit configured to obtain energy from electromagnetic waves. See, for example, U.S. Pat. No. 7,479,886 to Burr titled "Antenna Capacitance for Energy Storage" and Sample et al., "Photovoltaic Enhanced UHF RFID Tag Antennas for Dual Purpose Energy Harvesting," 2011 *IEEE International Conference on RFID*, 146-153 (2011), which are each incorporated herein by reference. In some embodiments, a plurality of sensor units each include at least one energy harvesting unit, for example RFID units. In some embodiments, the appurtenance includes an indicator operably attached to a processor, the indicator positioned on an edge of the appurtenance adjacent to an outer surface of the wound when the appurtenance is positioned for use with the wound dressing. For example, the indicator can include a least one of: a visual indicator, a vibratory indicator, or an auditory indicator. See, for example, US Patent Application No. 2009/0167495 to Smith, titled "Radio Frequency Identification Tags Adapted for Localization and State Indication," which is incorporated herein by reference.

In some embodiments, an appurtenance to a cavity wound dressing includes a transmitter unit. In some embodiments, an appurtenance includes a transmitter unit within at least one sensor unit. For example, in some embodiments, a sensor unit includes a transmitter unit, including an antenna. In some embodiments, a transmitter unit is part of an indicator within the sensor unit. In some embodiments, an appurtenance includes a transmitter unit operably connected to one or more sensor units. For example, an appurtenance to a cavity wound dressing can include a single transmitter unit connected with a wire to one or more sensor units. In some embodiments, a sensor unit is configured for a transmitter unit to operate as an indicator when a condition within a wound cavity is detected. For example, a sensor unit can include a RFID antenna attached to a temperature sensor including a bimetallic element that flexes at varying temperatures between 32 degrees Centigrade and 45 degrees Centigrade. The flex position of the bimetallic element is positioned adjacent to the RFID antenna, so that greater flex decreases the contact of the bimetallic element with the RFID antenna. In conditions wherein the bimetallic element of the temperature sensor is significantly flexed (e.g. approximately 45 degrees Centigrade), the bimetallic element has less contact with the RFID antenna relative to conditions wherein the bimetallic element of the temperature sensor is not significantly flexed (e.g. approximately 32 degrees Centigrade). The change in contact between the bimetallic element and the RFID antenna changes the response of the antenna, thereby varying the response of the transmitter unit depending on the temperature.

A "transmitter unit," as used herein, can be one or more of a variety of units that are configured to send and/or receive signals, such as signals carried as electromagnetic waves. In embodiments where the appurtenance includes a substrate, the transmission unit can be attached to a surface of the substrate, the transmission unit including circuitry and at least one antenna, the transmission unit configured to transmit a signal. A transmitter unit generally includes at least one antenna and associated circuitry. A transmitter unit can include a transmitter and a receiver. Alternatively, the receiver can be a separate unit, with its own antenna and associated circuitry. A transmitter unit can include volatile or non-volatile memory. A transmitter unit can include a processor. A transmitter unit can be operably connected to an energy source, such as a battery. In some embodiments of an appurtenance, it is desirable to include a self-compensating antenna, such as described in U.S. Pat. No. 7,055,754 to Forester, titled "Self-Compensating Antennas for Substrates having Differing Dielectric Constant Values," which is incorporated herein by reference. A transmitter unit can be operably connected to a processor. A transmitter unit can be operably connected to a sensor unit. A transmitter unit can be configured to transmit a signal in response to a received interrogation signal. A transmitter unit can include an energy harvesting unit, such as a unit configured to obtain energy from electromagnetic waves. A transmitter unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmitter unit can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. A transmitter unit can include a radio frequency identification device (RFID). A transmitter unit can be configured to be a transmitter of signals in the UHF range. A transmitter unit including an RFID device can be configured to transmit signals in the UHF standard range utilized in a global region, as illustrated in the "Worldwide RFID UHF Map" by Intelleflex Corporation (©2009), which is incorporated herein by reference. A transmitter unit can include a radio frequency identification device (RFID), which can be a passive RFID device, a semi-passive RFID device, or an active RFID device, depending on the embodiment. See, for example, Chawla and Ha, "An Overview of Passive RFID," *IEEE Applications and Practice*, 11-17 (September 2007), which is incorporated herein by reference. A transmitter unit can include a battery-assisted passive RFID device, such as sold by Alien Technology®, Morgan Hill, Calif., such as described in the brochure from Alien Technology® titled "Battery Assisted Passive Tags" and incorporated herein by reference. A transmitter unit can include an optical transmitter unit. A transmitter unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference. A transmitter unit can include at least two antennas. A transmitter unit can include a self-compensating antenna system. An antenna can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference. A transmitter unit can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmitter unit can be configured to transmit at approximately 131 kilohertz (KHz), for example as part of a RuBee™ (IEEE standard 1902.1) system (sold, for example, by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference. A transmitter unit can include a near field communication (NFC) device. A transmitter unit can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmitter unit can be operably coupled to a sensor, such as a sensor that detects changes in capacitance (see, e.g. Sample et al., "A Capacitive Touch Interface for Passive RFID Tags," 2009 *IEEE International Conference on RFID*, 103-109 (2009), which is incorporated herein by reference). A transmitter unit can be operably coupled to a sensor, such as described in: Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference. A transmission unit can be operably coupled to a data storage unit, for example as described in U.S. Pat. No. 7,825,776 to Smith and Haehnel, titled "Device Configuration with RFID," and US Patent Application No. 2009/0243813 to Smith at al., titled "Wireless Programming of Non-Volatile Memory with Near-Field UHF Coupling," which are each incorporated herein by reference.

In some embodiments, the transmitter unit can include an acoustic transmitter. For example, a transmitter unit can include a piezoelectric speaker. A variety of suitable piezoelectric speakers are available, including from Murata Manufacturing Co., Ltd., with North American corporate headquarters in Smyrna, Ga. (see, e.g. the Murata catalog titled "Piezoelectric Sounds Components" labeled P37E and dated Jan. 28, 2010, which is incorporated herein by reference). Some embodiments can include acoustic transmitter units such as those manufactured by Advanced Telemetry Systems (headquartered in Isanti, Minn.) for the Pacific Northwest National Laboratory (see, e.g. JSATS Acoustic Transmitter information sheet from the Pacific Northwest National Laboratory, updated March 2010, which is incorporated herein by reference). In some embodiments, an appurtenance can include a piezoelectric speaker configured as part of an acoustic transmitter and also to act as a signaling device (e.g. to generate a beeping noise in response to a signal from the processor).

In some embodiments, the transmitter unit can include an ultrasonic transmitter. In some embodiments, the transmitter unit can include an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled S15E and dated Oct. 31, 2008, which is incorporated herein by reference). The transmitter unit can be configured as part of an ultrasonic ranging system. See: Wang, "A Design Method of Ultrasonic Ranging System with High Accuracy," *Journal of Computational Information Systems*, 7: 7 pages 2444-2451 (2011), which is incorporated herein by reference. The transmitter unit can be configured to communicate with an ultrasonic communication system. See: Chen and Wu, "Ultrasonic System with Infrared Communication Technology," *Journal of Computers*, vol. 6, no. 11, pages 2468-2475 (2011), which is incorporated herein by reference.

In some embodiments, the transmitter unit can include an optical transmitter. For example, an optical transmitter unit can include one or more white light emitting diodes (LEDs). For example, an optical transmitter unit can include an infrared laser. For example, an optical transmitter unit can include a visible laser. In some embodiments, optical transmitter units can be desirable to minimize interference from nearby electrical equipment, such as medical equipment. See: Kavehrad, "Sustainable Energy-Efficient Wireless Applications Using Light," *IEEE Communications Magazine*, vol. 48, no. 12, pages 66-73, (2010); and Fadlullah and Kavehrad, "Indoor High-Bandwidth Optical Wireless Links for Sensor Networks" *Journal of Lightwave Technology*, vol. 28, no. 21, pages 3086-3094 (2010), which are incorporated herein by reference.

A sensor unit can include an indicator that is configured to actuate a switch in response to a stimulus from a detector. The sensor unit can be configured to cause a change in the state of the switch in response to a stimulus, such as the presence of an analyte. A "selectively actuatable switch," as used herein, refers to a switch of sufficient structure to allow or disallow a transmission unit to transmit a signal in response to a sensor unit. A selectively actuatable switch includes a switch that can be turned between settings (i.e. "on" and "off") in response to a stimulus. A selectively actuatable switch can, for example, be coupled to a transmission unit that includes an RFID device. See, for example, U.S. Pat. No. 7,411,505 titled "Switch Status and RFID Tag," which is incorporated herein by reference. A selectively actuatable switch can be a binary switch, or a switch with substantially two settings (i.e. "on" and "off"). A selectively actuatable switch can be configured to be irreversible, or to irreversibly go from one state to a second state. A selectively actuatable switch can be configured to be responsive to a change in capacitance.

Some embodiments include sensor units with detectors that are configured to be responsive to a change in the pH of fluid arising from the wound surface, or wound exudate. For example, pH changes can indicate potential infection in the cavity wound, or in a region of the cavity wound. For example, pH changes in wound exudate can indicate that a section of the wound cavity has an increased level of necrotic tissue, and a caregiver may wish to consider debridement. Detectors of pH can be, for example, iridium oxide based pH detectors. See, for example: the "flexible, iridium oxide pH sensor for wound dressing material" project from the University of Texas at Arlington, (information sheet identified as UTA reference number 08-21); and US Patent Application Publication No. 2011/0140703 to Chiao et al., which are each herein incorporated by reference.

Some embodiments include sensor units with detectors that recognize analytes that are specific proteins. Some embodiments include sensor units with detectors that recognize specific analytes present in wound exudate. For example, in some embodiments detectors recognize bacterial proteins indicative of chronic, or long-term, non-healing cavity wounds. See Dowd et al., "Survey of Bacterial Diversity in Chronic Wounds Using Pyrosequencing, DGGE, and Full Ribosome Shotgun Sequencing," *BMC*

*Microbiology* 8:43 (2008), which is incorporated by reference. These bacterial proteins can be present on the wound surface, or in the wound exudate from a cavity wound. Some embodiments include detectors of ATP levels in fluid originating from the surface of a cavity wound. See International Publication No. WO 00/08203, "Method of Monitoring Bacterial Contamination in a Wound," to Walker, which is incorporated by reference herein. Some embodiments include detectors of oxygen in fluid within the cavity wound and indicators including luminescent markers. See Grist et al., "Optical Oxygen Sensors for Applications in Microfluidic Cell Culture," *Sensors* 10:9286-9316 (2010), which is incorporated by reference. Low oxygen levels in a cavity wound can indicate to a caregiver, for example: a lack of vascular function in the periwound tissue; a bacterial infection; or excess necrotic tissue. In some embodiments, sensor units include detectors with an antibody that detects cortisol, and an indicator including a visualization of antibody binding. See U.S. Pat. No. 5,912,114, "Wound Diagnosis by Quantitating Cortisol in Wound Fluids," to Hutchinson et al., which is incorporated by reference. In some embodiments, sensor units include detectors that respond to markers of inflammation, such as described in U.S. Pat. No. 7,794,925, "Diagnosis of Clinical Infection of a Wound" to Cullen, and International Publication No. WO 03/040406, "Wound Monitoring," to Cullen, which are each incorporated by reference. In some embodiments, sensor units include detectors that respond to markers of infection including high molecular weight phospholipase $A_2$. See US Patent Application Publication No. 2007/0231380, "Diagnosis and Prognosis of Wound Infection by Measurement of Phospholipase A2 in Wound Fluid," to Shah et al., which is incorporated by reference. In some embodiments, the absence of a protein in wound fluid or exudate can be clinically relevant information. See US Patent Application Publications Nos. 2010/0166694 and 2012/0010099, each "Diagnostic Markers of Wound Infection," to Stephens et al., which are each incorporated by reference.

FIG. 2A depicts an appurtenance 230 including a substrate with a plurality of affixed sensor units 220A, 220B, and 220C. The plurality of sensors 220A, 220 B and 220C are collectively referred to as 'sensor units 220' with reference to the Figures herein. Such plurality of sensor units 220 can include sensors of the same or distinct types. In the embodiment illustrated, the appurtenance 230 includes a plurality of affixed sensor units of three distinct types 220A, 220B, 220C. The sensor units of different types are configured to indicate the presence of different conditions or analytes within a cavity 120 of a cavity wound 100. For purposes of illustration, the sensor units 220A, 220B, 220C are depicted in FIG. 2A as different shapes, although in actual embodiments there need not be any overt or visual difference between sensor units of different types. Although the embodiment illustrated includes sensor units of three distinct types, 220A, 220B, 220C, some embodiments include a single sensor type, two sensor types, or more than three sensor types. As shown in FIG. 2A, an appurtenance 230 including a substrate with a plurality of affixed sensor units can include a plurality of sensor units of at least three distinct types 220A, 220B, 220C oriented as a pattern relative to the wound surface. In some embodiments, a plurality of sensor units of at least two distinct types are oriented as a pattern relative to the wound surface. For example, at least one sensor unit, e.g., 220A including a detector of physical pressure can be affixed to the substrate 200 at a location corresponding to a region of the wound surface adjacent to a bone. A position of a cavity wound 100 surface adjacent to a bone can be particularly prone to further injury due to physical pressure, and monitoring of physical pressure at such a location with the appurtenance 230 may be desirable in some medical situations. An appurtenance 230 including a substrate with a plurality of affixed sensor units can include a plurality of sensor units including at least one sensor unit 220B configured to detect both physical pressure and temperature over time.

An appurtenance 230 including a substrate with a plurality of affixed sensor units can include a plurality of sensor units 220 which in the aggregate have been selected and positioned on the appurtenance substrate with a size, shape, mass and arrangement to minimize physical pressure at the wound surface from the appurtenance. For example, substrate with a plurality of affixed sensor units can include a plurality of sensor units of a size, shape, mass and arrangement so that the appurtenance is predicted to press with a force of less than 32 mm Hg at the wound surface during use with the cavity wound. For example, substrate with a plurality of affixed sensor units can include a plurality of sensor units of a size, shape, mass and arrangement so that the appurtenance is predicted to press with a force of less than 20 mm Hg at the wound surface during use with the cavity wound. For example, substrate with a plurality of affixed sensor units can include a plurality of sensor units of a size, shape, mass and arrangement so that the appurtenance is predicted to press with a force of less than 12 mm Hg at the wound surface during use with the cavity wound. In some embodiments, a smaller and thinner type of sensor unit is positioned on the substrate adjacent to the center of the appurtenance, assuming that the center of the appurtenance will be positioned adjacent to the center of the wound, a particularly sensitive region, during use of the appurtenance. In some embodiments, a relatively larger and thicker type of sensor unit is positioned adjacent to the edge of the appurtenance, assuming that the edge will be positioned outside of the wound itself during use of the appurtenance. The plurality of affixed sensor units can be fabricated of substantially thin and lightweight materials. For example, affixed sensor units can be fabricated to be less than 5 mm in thickness, less than 10 mm in thickness, less than 15 mm in thickness, less than 20 mm in thickness, or less than 25 mm in thickness. The plurality of affixed sensor units can be fabricated with a flexible, lightweight cover to minimize physical pressure from the sensor units within the cavity wound 100 during use. For example, one or more sensor units affixed to the substrate 200 can include a foam cover. For example, one or more sensor units affixed to the substrate 200 can include a flexible plastic cover around an edge region of the sensor units.

In some embodiments, a substrate 200 includes a plurality of unidirectional fluid flow structures, wherein the unidirectional fluid flow structures are configured to allow fluid flow from the wound-facing surface to one or more of the plurality of sensor units 220 attached to the substrate 200. See, for example, U.S. Pat. No. 6,420,622 to Johnston et al., "Medical Article Having Fluid Control Film," which is incorporated herein by reference. For example, the substrate 200 can include a plurality of channels or grooves in the surface configured to allow fluid flow from the wound-facing surface to one or more of the plurality of sensor units 220 attached to the substrate 200.

An appurtenance can be fabricated from a variety of materials, as appropriate to an embodiment. An appurtenance can be fabricated, for example, substantially from a plastic material. For example, a structural portion, such as a substrate, can be fabricated from a plastic material. An appurtenance can be fabricated, for example, from one or more acrylics, polyesters, silicones, polyurethanes and halogenated plastics. An appurtenance can be fabricated from one or more bio-compatible materials, for example bio-compatible plastics, foams, resins, epoxies and metals. An appurtenance can be fabricated from one or more composite materials, such as plastic with an overlay of epoxy or plastic with an overlay of one or more metals. An appurtenance including a transmission unit can include, for example, one or more metal components, for example as circuitry or as one or more antennas. An appurtenance including a transmission unit can include, for example, stainless steel, copper or zinc alloy. An appurtenance can be fabricated from one or more ceramic materials, such as within a transmission unit. Generally, it is envisioned that materials with low mass will be suitable for a variety of appurtenance embodiments, so as to reduce weight and associated physical stress on a wound dressing. Similarly, it is envisioned that materials with sufficient strength and toughness to be fabricated into small and thin components will be desirable for fabrication of appurtenance embodiments. As the appurtenances are configured for use with wound dressings and disposed of with the wound dressings, materials that do not require special handling or disposal are preferable in most embodiments.

Appurtenances such as those described herein can be configured to be used in conjunction with cavity wound dressings wherein the patient is being directly monitored using other devices, for example as described in U.S. Pat. No. 7,030,764 to Smith and Cooper, titled "Apparatus and Method for Reducing the Risk of Decubitus Ulcers;" U.S. Pat. No. 7,297,112 to Zhou et al., titled "Embedded Bio-Sensor System;" U.S. Pat. Nos. 7,372,780, 8,014,234 and 7,813,226 to Braunberger, titled "Timing System and Device and Method for Making the Same;" U.S. Pat. No. 7,666,151 to Sullivan et al., titled "Devices and Methods for Passive Patient Monitoring;" U.S. Pat. No. 7,703,334 to Cochran, titled "Bandage Type Sensor Arrangement and Carrier Assembly Therefore, and Method of Manufacture;" and International Patent Publication No. WO 2005/009328 to Nikolic, titled "ABT-Anti-Bedsore Timer," which are each incorporated herein by reference. Appurtenances such as those described herein can also be used in conjunction with a system to monitor assets within a health care facility, for example as described in US Patent Application No. 2007/0247316 to Wildman et al., titled "Article Locating and Tracking Apparatus and Method," which is incorporated herein by reference.

Figure 2B:
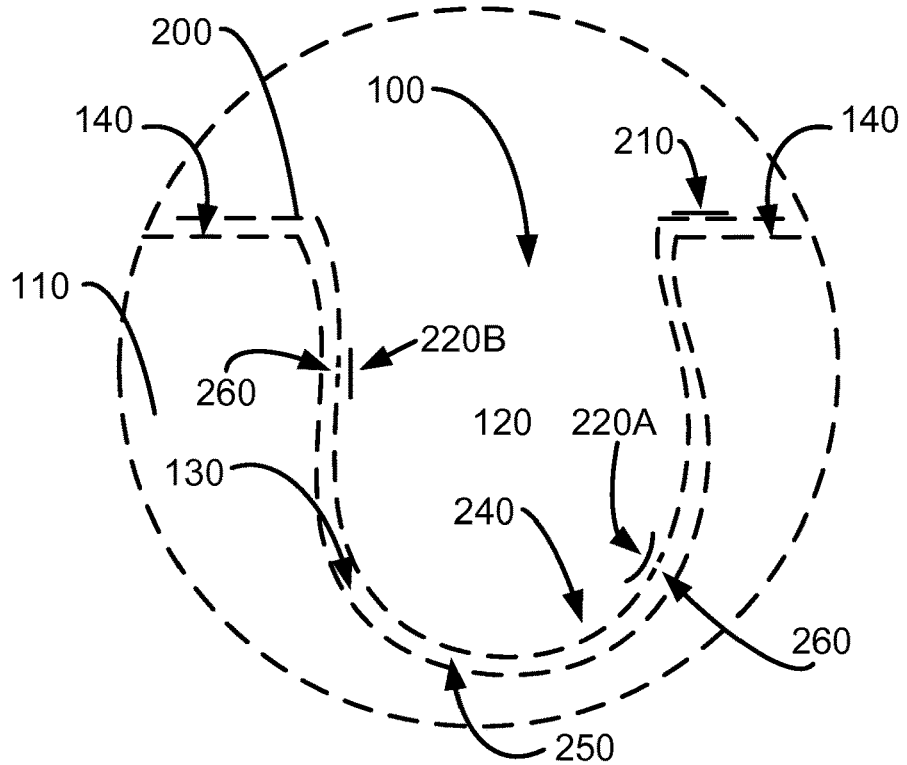
FIG. 2B illustrates, in cross-section, an appurtenance in use in a cavity wound.

FIG. 2B illustrates an appurtenance 230 to a cavity wound dressing in use. FIG. 2B shows a cross-section view of a substantially planar, flexible appurtenance substrate 200, such as shown in an external view in FIG. 2A, in situ within a cavity wound 100. As shown in FIG. 2B, the cavity wound 100 creates a cavity 120 within a body part 110, such as a leg (e.g. as illustrated in FIG. 1A). The cavity wound 100 has a wound surface 130 and a surface region 140 of the periwound region. The substrate 200 has a thin, flexible structure that substantially conforms to the wound surface 130 of the cavity wound 100. The substrate 200 illustrated in FIG. 2B has a surface size larger than the wound surface 130 of the cavity wound 100, and therefore part of the substrate 200 covers the surface region 140 of the periwound region. The substrate 200 includes a wound-facing surface 250 configured to face the wound surface 130. For example, the wound-facing surface 250 can be configured to be substantially smooth in order to minimize the potential for regions of localized pressure at the wound surface 130 when the appurtenance is in use. For example, the wound-facing surface 250 can include one or more apertures 260 in the wound-facing surface 250, the apertures 260 configured to allow fluid flow from the wound surface 130 to one or more attached sensor units 220. The substrate 200 includes a cavity-facing surface 240. The cavity-facing surface 240 can include, for example, one or more attachment sites for the attachment of a primary wound dressing. The cavity-facing surface 240 can include, for example, one or more attached sensor units 220. The cavity-facing surface 240 can include, for example, one or more orientation indicators 210 for placement of the appurtenance within the cavity 120 and orientation of the appurtenance after removal from the cavity 120.

Some embodiments include an appurtenance to a cavity wound dressing, wherein the appurtenance includes: a plurality of sensor units, wherein each sensor unit includes an attachment region configured to affix to a porous wound dressing material and wherein each sensor unit is configured to be operational when immersed in fluid or under physiological physical pressure and temperature within a cavity wound; and the plurality of sensor units in the aggregate of a size and mass to allow for medical use with the porous dressing material at the cavity wound.

For example, the plurality of sensor units can include at least two types of sensor units (e.g. sensor units with detectors configured to detect two or more distinct analytes, or sensor units configured to detect both specific analytes and specific conditions within the cavity). Some embodiments include a plurality of sensor units including at least one sensor unit configured to detect physical pressure and at least one sensor unit configured to detect temperature. For example, a first sensor unit can detect physical pressure, and a second sensor unit can detect temperature. The first sensor unit and the second sensor unit can be positioned adjacent to each other relative to the surface of the appurtenance. Some embodiments include a plurality of sensor units including at least one sensor unit configured to detect physical pressure and at least one sensor unit configured to detect temperature, as well as at least one sensor unit configured to detect elapsed time. For example, a first sensor unit can detect physical pressure and a second sensor unit can detect temperature and a third sensor unit can record an elapsed time value. For example, a first sensor unit can detect physical pressure and a second sensor unit can detect temperature and a third sensor unit can detect an elapsed time value, while an external device receiving the record from the first, second and third sensors can calculate the pressure and temperature over time from the data obtained from the first, second and third sensors. For example, the external device receiving the record from the first, second and third sensors can indicate a composite score of temperature and pressure over elapsed time based on data received from the first, second and third sensors. For example, a sensor unit can detect physical pressure and indicate if the detected values have exceeded a pre-set threshold value. For example, a sensor unit can detect temperature and indicate if the detected values have exceeded a pre-set threshold value. For example, a sensor unit can detect elapsed time and indicate if the elapsed time value has exceeded a pre-set threshold value.

Some embodiments include a plurality of sensor units including at least one sensor unit configured to detect an analyte in wound exudate. For example, a sensor unit can include a detector configured to detect an analyte such as a blood protein, a bacterial protein, a viral protein, or a biomarker. Some embodiments include a plurality of sensor units of a size, shape, mass and arrangement in the aggregate to minimize physical pressure at the wound surface during medical use with a porous dressing material. For example, the mass of the sensor units in the aggregate can be less than a predetermined maximum mass. For example, a sensor unit can include soft and flexible outer coatings. For example, a sensor unit can be configured with substantially low aspects for the embodiment. The sensor units can be arranged on different sizes and shapes of appurtenance substrates to minimize physical pressure on the wound surface during use. Some embodiments include a plurality of sensor units including at least one antenna operably attached to at least one sensor unit. Some embodiments include a plurality of sensor units including at least one chemical or biological-based sensor unit, as described herein. Some embodiments include a plurality of sensor units including at least one positional indicator. Some embodiments include a plurality of sensor units including at least one temperature sensor unit. Some embodiments include a plurality of sensor units including at least one pressure sensor unit. Some embodiments include a plurality of sensor units including at least one fluid-activated sensor unit. Some embodiments include a plurality of sensor units including at least one sensor unit including an optically resolvable detection indicator. Some embodiments include a plurality of sensor units including at least one sensor unit including a detection indicator operably attached to a RFID antenna. Some embodiments include a plurality of sensor units including a plurality of sensor unit types, wherein all of the plurality of sensor unit types are functional under expected environmental conditions, such as temperature, moisture, and physical pressure, within a cavity of the cavity wound. In some embodiments, one or more sensor unit is operably connected to a transmission unit. In some embodiments, one or more sensor unit is externally-readable. For example, a sensor unit can be externally-readable by an external device. For example, a sensor unit can include a detector configured to transmit a specific wavelength of light in the presence of an analyte and in response to UV excitation by an external source. An external device can be utilized to scan a previously used appurtenance with UV and then to detect the transmitted specific wavelength from the sensor unit.

In some embodiments, an appurtenance includes at least one orientation indicator including an attachment region configured to affix to a porous wound dressing material. For example, the orientation indicator can include a detachable cover over an adhesive backing on one surface, and a visible pattern on another surface. In some embodiments, an appurtenance includes a porous wound dressing material suitable for attachment of the plurality of sensor units, the porous wound dressing material being flexible. For example, a porous wound dressing material can be fabricated from porous medical-grade silicone. For example, a porous wound dressing material can be fabricated from a foam material.

Figure 3:
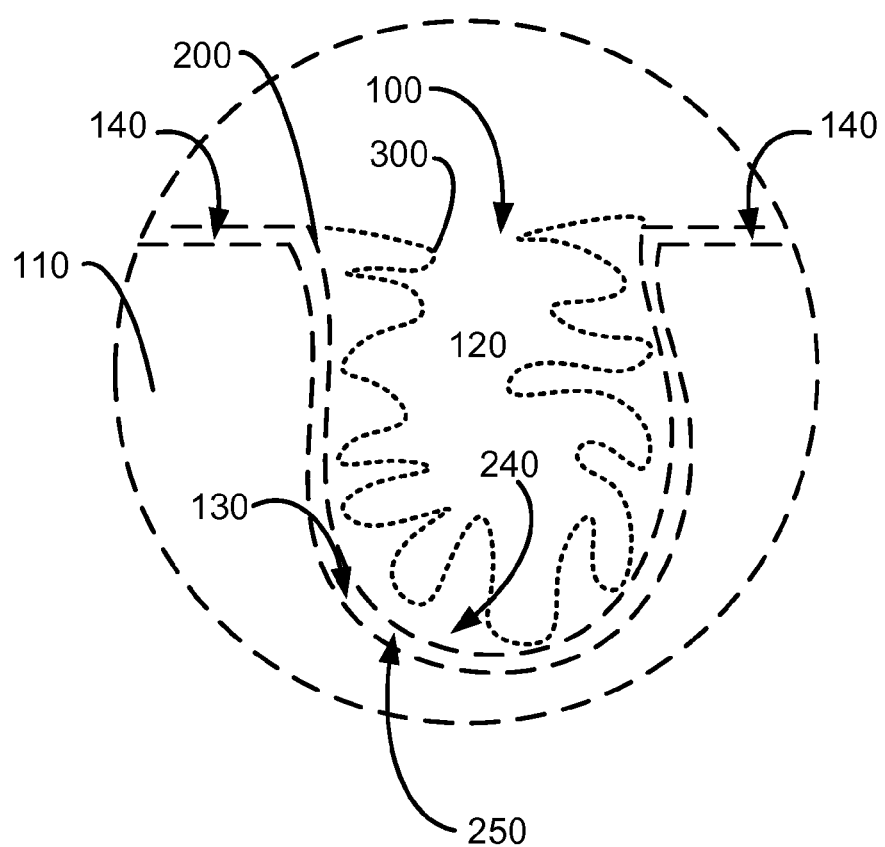
FIG. 3 shows, in cross-section, an appurtenance in use in a cavity wound with a wound dressing.

FIG. 3 shows an appurtenance 230 to a cavity wound dressing 300 in use. The view shown in FIG. 3 is a cross-section view of a cavity wound 100 forming a cavity 120 in a body part 110, similar to the view shown in FIG. 2B. The interior of the cavity 120 of the cavity wound 100 has a wound surface 130. FIG. 3 illustrates an appurtenance with a substrate 200 that is a flexible, porous sheet structure with a wound-facing surface 250 positioned adjacent to the wound surface 130. The appurtenance with a substrate 200 includes a cavity-facing surface 240 positioned adjacent to the interior region of the cavity 120. The wound 100 also includes a wound dressing 300 positioned within the cavity 120 and adjacent to the cavity-facing surface 240 of the substrate 200 of the appurtenance. The wound dressing 300 can include, for example, gauze dampened with sterile saline, positioned to reduce dryness at the wound surface 130 and to retain the cavity 120 as an open, uncompressed structure. In a configuration such as shown in FIG. 3, saline or other fluid from the wound dressing 300 can pass through the porous substrate 200 of the appurtenance in order to retain a moist environment at the wound surface 130. Wound exudate, including blood and other fluids, can also pass to the wound-facing surface 250 of the porous substrate 200 of the appurtenance, and to the sensor units embedded within the substrate 200.

Figure 4A:
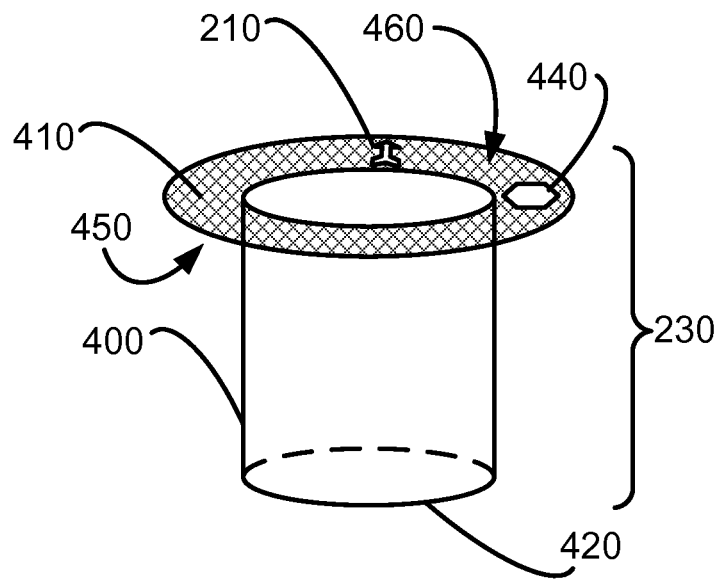
FIG. 4A depicts an appurtenance to a cavity wound dressing.

FIG. 4A illustrates aspects of an appurtenance 230. The appurtenance 230 shown in FIG. 4A is a structure configured to approximate the interior size and shape of a cavity in a cavity wound. The appurtenance 230 shown in FIG. 4A includes a three dimensional structure with at least one wound-facing surface, the at least one wound-facing surface of a size and shape to reversibly mate with the wound surface of the cavity wound. The appurtenance 230 is fabricated with a substantially pliable and fluid-permeable structure 410, 400, 420. The appurtenance depicted in FIG. 4A includes a substrate with one or more walls 400 configured to approximate the size and shape of a cavity in a cavity wound. The substrate also includes a distal region 420 connected to the walls 400. The substrate is substantially pliable and porous, while retaining enough rigidity to maintain the approximate three-dimensional structure of the substrate within the cavity. The substrate is sufficiently flexible to bend or conform as needed during normal movement of an individual while it is in use, while not creating a pressure greater than 32 mm Hg against the wound surface.

The appurtenance 230 shown in FIG. 4A includes an edge region 410, the edge region including a surface 450 positioned to be adjacent with the surface region of the periwound region when the appurtenance 230 is in use. The edge region 410 also includes a surface 460 positioned to be distal to the surface region of the periwound region when the appurtenance 230 is in use. The surface 460 of the edge region 410 can, for example, be visible to a caregiver when the appurtenance 230 is in use. In the embodiment shown in FIG. 4A, the surface 460 of the edge region 410 includes an attached orientation indicator 210. The orientation indicator 210 can include, for example, a visible marking that can assist a caregiver with orienting the appurtenance within a cavity wound during wound care. The surface 460 of the edge region 410 shown in FIG. 4A also includes a temperature sensor unit 440. The temperature sensor unit 440 can be configured to detect the temperature at or proximate to a surface region of the periwound region when the appurtenance 230 is in use. See U.S. Pat. No. 6,963,772, and US Patent Application Publication No. 2006/0047218 "User-Retainable Temperature and Impedance Monitoring Methods and Devices," each to Bloom, which are each incorporated by reference. The temperature sensor unit 440 can be configured to detect and record the temperature at or proximate to a surface region of the periwound region over time, for example for use in comparison with a temperature record from a sensor unit attached to the substrate 400, 420 positioned within a wound cavity.

Figure 4B:
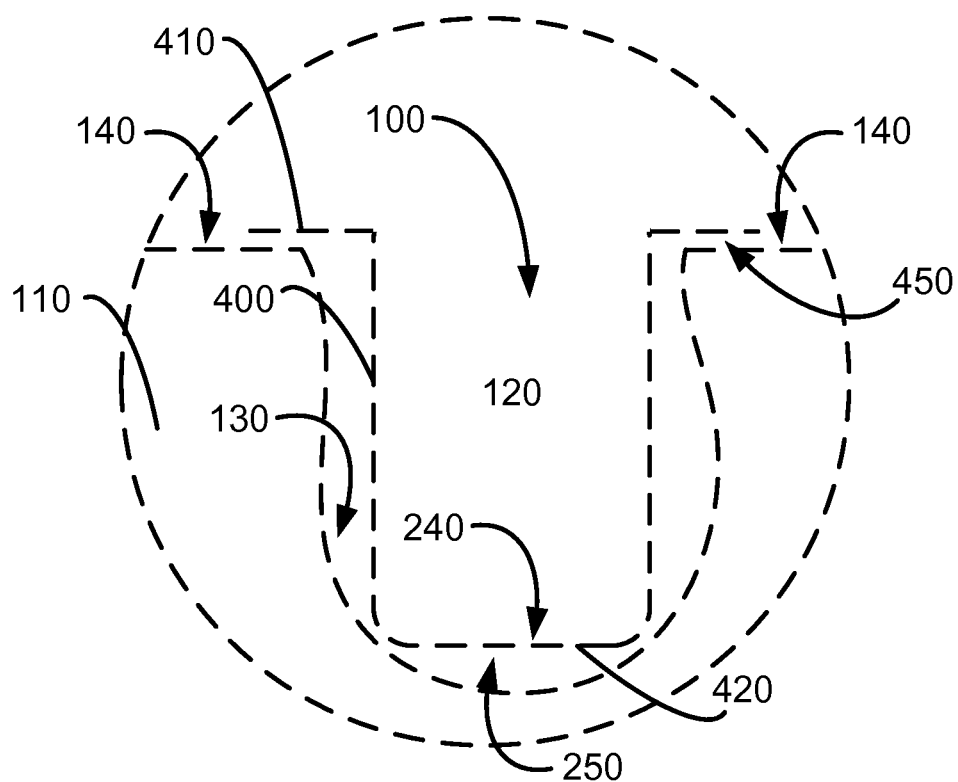
FIG. 4B illustrates, in cross-section, an appurtenance in use in a cavity wound.

FIG. 4B illustrates a view of the appurtenance of FIG. 4A in situ within a cavity wound 100. The appurtenance is positioned within the cavity 120 of the cavity wound 100 so that the surface 450 of the edge region 410 is adjacent to the surface region 140 of the periwound region. The walls 400 of the appurtenance are oriented substantially parallel to the sides of the wound cavity 120. The distal region 420 of the appurtenance is oriented adjacent to the distal region of the wound cavity 120. The wound-facing surface 250 of the appurtenance is oriented adjacent to the wound surface 130. In the embodiment illustrated in FIG. 4B, there is a space or gap between the wound-facing surface 250 of the appurtenance and the wound surface 130. In some embodiments, a therapeutic agent can be utilized to fill the gap between the wound-facing surface 250 of the appurtenance and the wound surface 130. The gap can be filled, for example, with a medicament, such as an alginate-based compound. The gap can be filled, for example, with an antibacterial agent in a gel or foam base. In some embodiments, the wound-facing surface 250 of the appurtenance is configured to reversibly mate with the wound surface 130 with a minimal gap. The appurtenance illustrated in FIG. 4B includes a substrate 400, 410, 420 fabricated from a thin material so that the cavity-facing surface 240 of the substrate faces an internal cavity 120.

Figure 5:
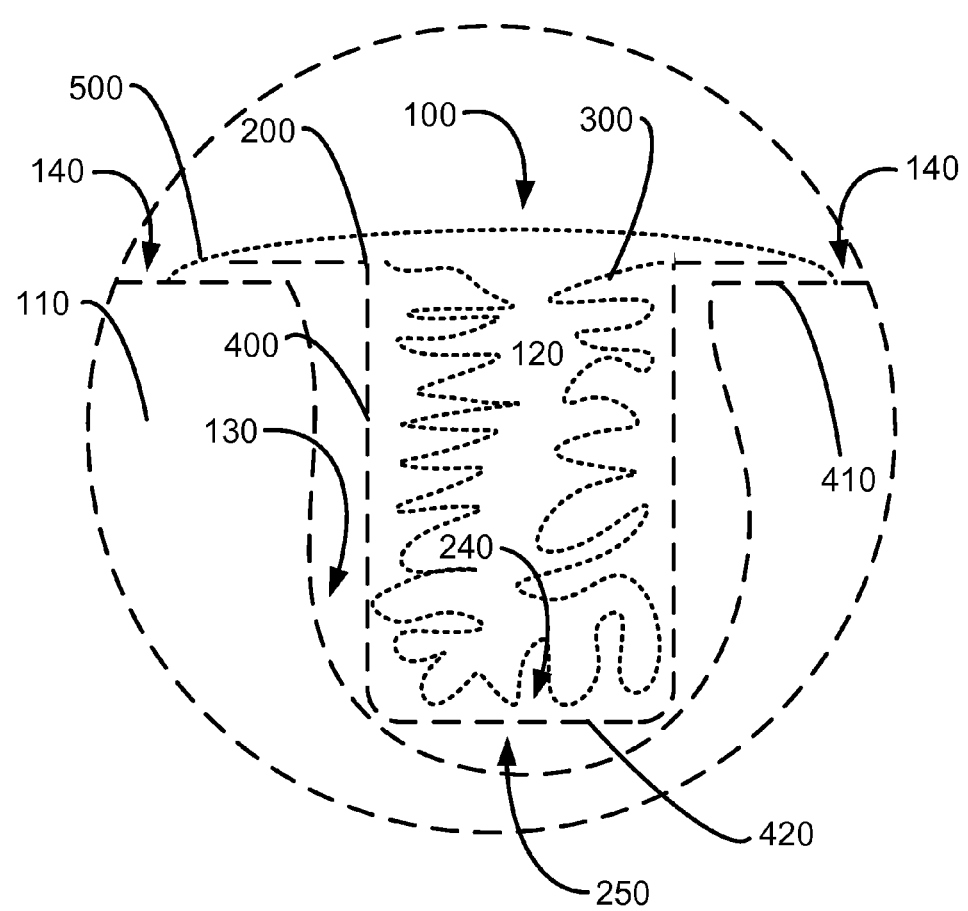
FIG. 5 shows, in cross-section, an appurtenance in use in a cavity wound with a wound dressing.

FIG. 5 illustrates a cross-section view, showing aspects of an appurtenance, such as shown in FIGS. 4A and 4B, in use in situ with a wound dressing 300 and a secondary wound dressing 500 on a cavity wound 100. The appurtenance is positioned within the cavity 120 of the cavity wound 100 in a similar fashion to the view shown in FIG. 4B. The cavity-facing surface 240 of the substrate creates an internal region of the substrate 400, 410, 420 within the cavity 120. The internal region of the appurtenance holds a wound dressing 300. The wound dressing 300 is a substantially planar structure, which has been compressed into the cavity 120 space of the wound 100. For example, the wound dressing 300 can include a saline-saturated gauze material folded to pack into the cavity 120. The porous substrate 400, 420 allows fluid from the wound dressing 300 to flow to the wound surface 130 as well as fluid from the wound surface 130 to flow to the wound dressing 300. A secondary dressing 500 is positioned over the appurtenance and the wound dressing 300. For example, the secondary dressing 500 can include a thin plastic film with adhesive on the surface facing the wound 100. The adhesive can secure the secondary dressing 500 to the surface region 140 of the periwound region as well as to the edge region 410 of the appurtenance, thereby retaining the appurtenance, the wound dressing 300 and the secondary dressing 500 in place during use.

Figure 6:
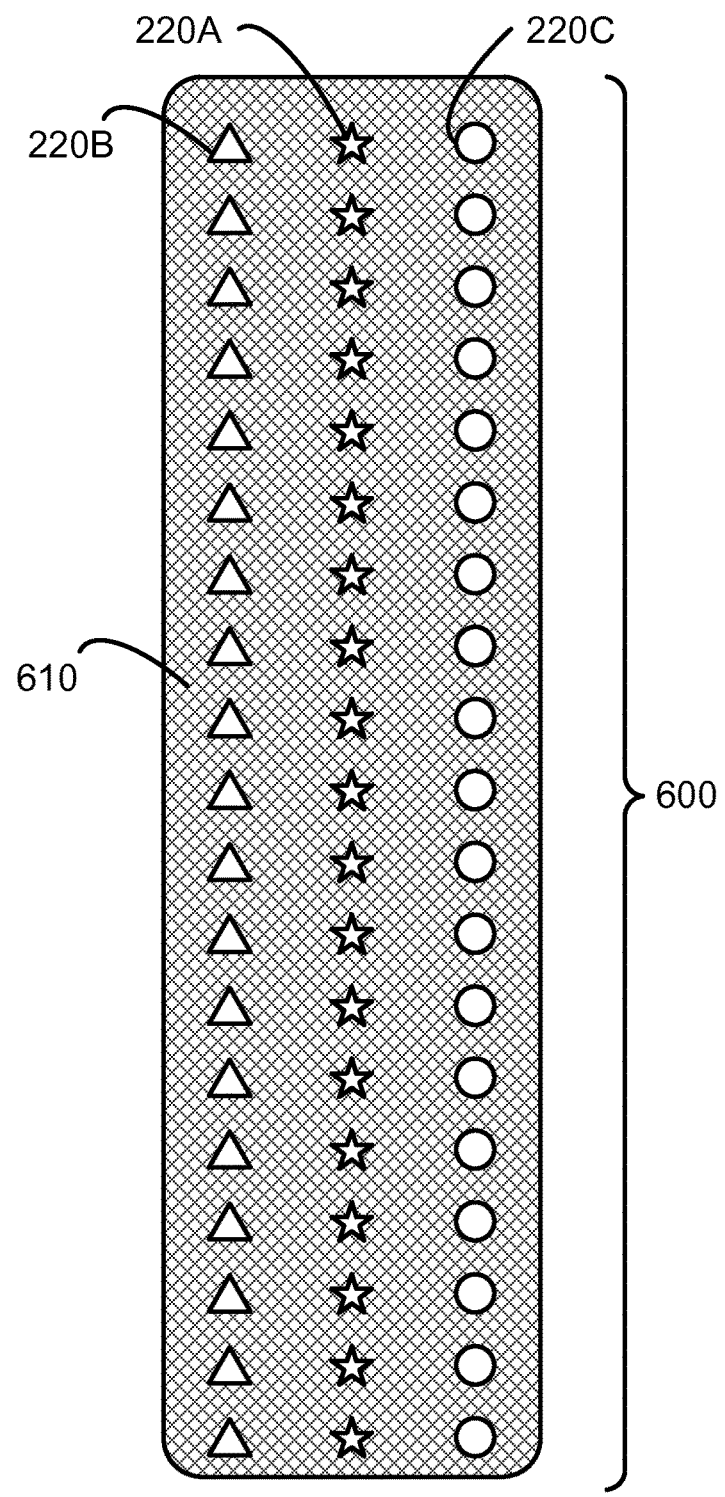
FIG. 6 depicts an appurtenance to a cavity wound dressing.

FIG. 6 illustrates an appurtenance 600 to a wound dressing for a cavity wound. The appurtenance 600 illustrated is a substantially planar, elongated structure including a substrate 610 with an array of attached sensor units 220. The sensor units 220 depicted are of three types 220A, 220B, 220C, which are configured to detect at least three types of analytes and/or conditions within a wound cavity. Although three types of sensor units 220A, 220B, 220C are depicted in FIG. 6, some embodiments include a single type of sensor unit 220, two types of sensor units 220, or more than three types of sensor units 220. The sensor units 220A, 220B, 220C depicted in FIG. 6 are shown as different shapes (triangle, star, and circle respectively), for purposes of illustration, however sensor units 220A, 220B, 220C configured to detect different analytes can have the same external appearance. The appurtenance 600 illustrated in FIG. 6 has the sensor units 220 attached to the substrate in an array, which is oriented as linear rows of each type of sensor unit 220A, 220B, 220C along the length of the appurtenance 600. A substrate 610 in an embodiment such as that illustrated is fabricated from a flexible, porous material that is stable and durable in physiological conditions within a wound cavity, such as temperature and pressure. A substrate 610 in an embodiment such as that illustrated is stable and durable in the presence of cavity wound fluid and exudate. The substrate is porous to fluids within the wound cavity, for example, sterile saline or similar medicaments used with a primary dressing, or blood or other wound-based fluids and exudate. For example, a substrate 610 can be fabricated from a plastic mesh, gauze, or foam material. For example, a substrate 610 can be fabricated from medical-grade woven mesh, gauze or fabric. The substrate 610 can include layers of different materials. In some embodiments, the sensor units 220 are embedded within the substrate 610, such as between layers of the substrate 610 structure. The sensor units 220 attached to the substrate 610 are oriented and positioned to detect analytes and conditions in a wound cavity in the region adjacent to the appurtenance 600. The appurtenance 600 is configured for use within a wound cavity, and is, therefore, soft, pliable, durable and operational under physiological temperatures, conditions, and physical pressures. The appurtenance 600 is configured for use within a wound cavity, and is, therefore, of a mass and configuration to not place physical pressure or shear force on a wound surface within a cavity wound during use. For example, the total mass of the appurtenance 600, including the substrate 610 and the sensor units 220, should be minimized in a given embodiment to reduce the total physical pressure on the wound surface. For example, each of the individual sensor units 220 should be configured with minimal mass and aspect to not create localized pressure or physical shear force against a region of the wound surface. The appurtenance 600 is configured to be used when dry, damp or wet. For example, the appurtenance may be damp during use when the wound dressing is an alginate material coating at least one surface of the substrate 610. For example, the appurtenance may be damp during use when the wound dressing is a saline-soaked gauze material affixed to the substrate 610. For example, the appurtenance may be dry during use and then become wet with wound exudate over time during use in the cavity wound.

In some embodiments, an appurtenance substrate can be fabricated with one or more regions configured for the attachment of different modules. In some embodiments, an appurtenance includes modules that are configured for removal and replacement. During fabrication, a basic appurtenance substrate structure can be utilized and different specific modules added as desired in a particular embodiment. For example, an appurtenance substrate can be fabricated with at least one region configured to attach a sensor unit. For example, a region configured to attach a sensor unit can include a region with a surface conforming to an outer surface of the sensor unit. For example, a region configured to attach a sensor unit can include a conduit configured to align with a hollow interior region of the sensor unit. For example, a region configured to attach a sensor unit can include a conduit configured to align with a detection region of a sensor unit. The region of the appurtenance substrate configured to attach a sensor unit can be configured for attachment of different types of sensor units, depending on the embodiment. For example, the region of the appurtenance substrate configured to attach a sensor unit can be configured for attachment of sensor units of different dimensions or different materials as desired in the construction of a particular embodiment. In some embodiments, an appurtenance substrate can have multiple regions configured for attachment of multiple sensor units of different types. In some embodiments, an appurtenance substrate can have one or more removable antenna modules. For example, an appurtenance substrate can have one or more removable power source modules, such as batteries. In some embodiments, a module can include a spacer element, or a component configured to assist in physically positioning one or more other modules.

Figure 7:
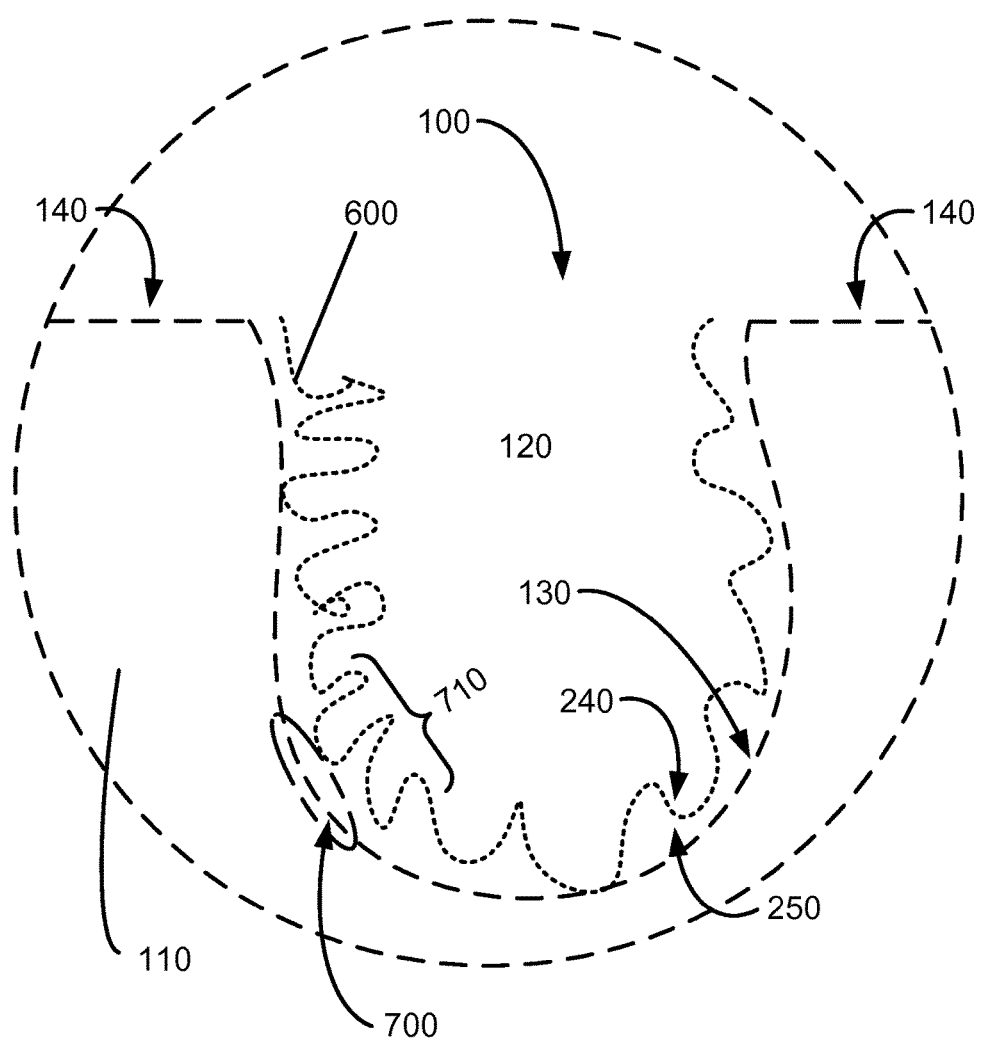
FIG. 7 illustrates, in cross-section, an appurtenance in use in a cavity wound.

FIG. 7 illustrates an appurtenance 600, such as illustrated in FIG. 6, in situ within a cavity wound 100 in cross-section. The appurtenance 600 in FIG. 7 is a substantially planar, elongated structure packed within a cavity wound 100. The appurtenance 600 in FIG. 7 includes a plurality of sensor units, which are distributed with the appurtenance 600 within the cavity wound 100. For purposes of illustration, the appurtenance 600 is shown independently of a wound dressing. An appurtenance 600 can be utilized, for example, with a wound dressing that is an alginate medicinal material coating the wound-facing surface 250 of the appurtenance 600. An appurtenance 600 can be placed, for example, in association with a wound dressing that is a medical gauze or bandage-like material that can be placed between the wound-facing surface 250 of the appurtenance 600 and the wound surface 130. An appurtenance 600 can be placed, for example, in association with a wound dressing that is a medical gauze or bandage-like material positioned adjacent to the cavity-facing surface 240 of the appurtenance 600. A wound dressing can be wet, for example saturated with water or saline solution. In the embodiment illustrated in FIG. 7, the appurtenance 600 is packed and entirely placed within the cavity 120 of the wound 100, i.e. there is no edge region of the appurtenance 600 positioned adjacent to the surface 140 of the periwound region. However, in some embodiments, an appurtenance 600 includes an edge region that is positioned adjacent to the surface 140 of the periwound region.

FIG. 7 illustrates that the cavity wound 100 includes a section 700 of the wound surface 130 that provides or is subject to conditions that are distinct from the remainder of the wound surface 130. For example, the section 700 of the wound surface 130 can include a bacterial infection, with the associated elevation in bacterial proteins provided in the section 700. For example, if the section 700 of the wound surface 130 includes a bacterial infection, analytes that are markers of bacterial infection, such as bacterial proteins and immune response proteins, would be present at an elevated level in that section 700. Some of these analytes would move to the adjacent section 710 of the appurtenance 600, such as through fluid flow through the porous substrate of the appurtenance 600. Sensor units within the corresponding adjacent section 710 of the appurtenance 600 will detect the analytes flowing through the region. For example, the section 700 of the wound surface 130 can include a region that has been subject to increased physical pressure, for example through the actions of the patient, and therefore may include high levels of wound debris and a relatively low oxygen saturation. The corresponding adjacent section 710 of the appurtenance 600 would, therefore, be subject to similar local conditions. Sensor units on the adjacent section 710 of the appurtenance 600 will detect the local conditions. For example, if the section 700 of the wound surface 130 includes a region that is subject to physical pressure beyond a minimal level (e.g. 5 mm Hg or 10 mm Hg), the corresponding adjacent section 710 of the appurtenance 600 will also be subject to the increased physical pressure. Sensor units within the corresponding adjacent section 710 of the appurtenance 600 will detect the increased physical pressure. In some embodiments, information regarding a detection can be transmitted from an associated transmitter. In some embodiments, the detection will cause a change in the sensor unit, such as an optically-detectable color change.

Figure 8:
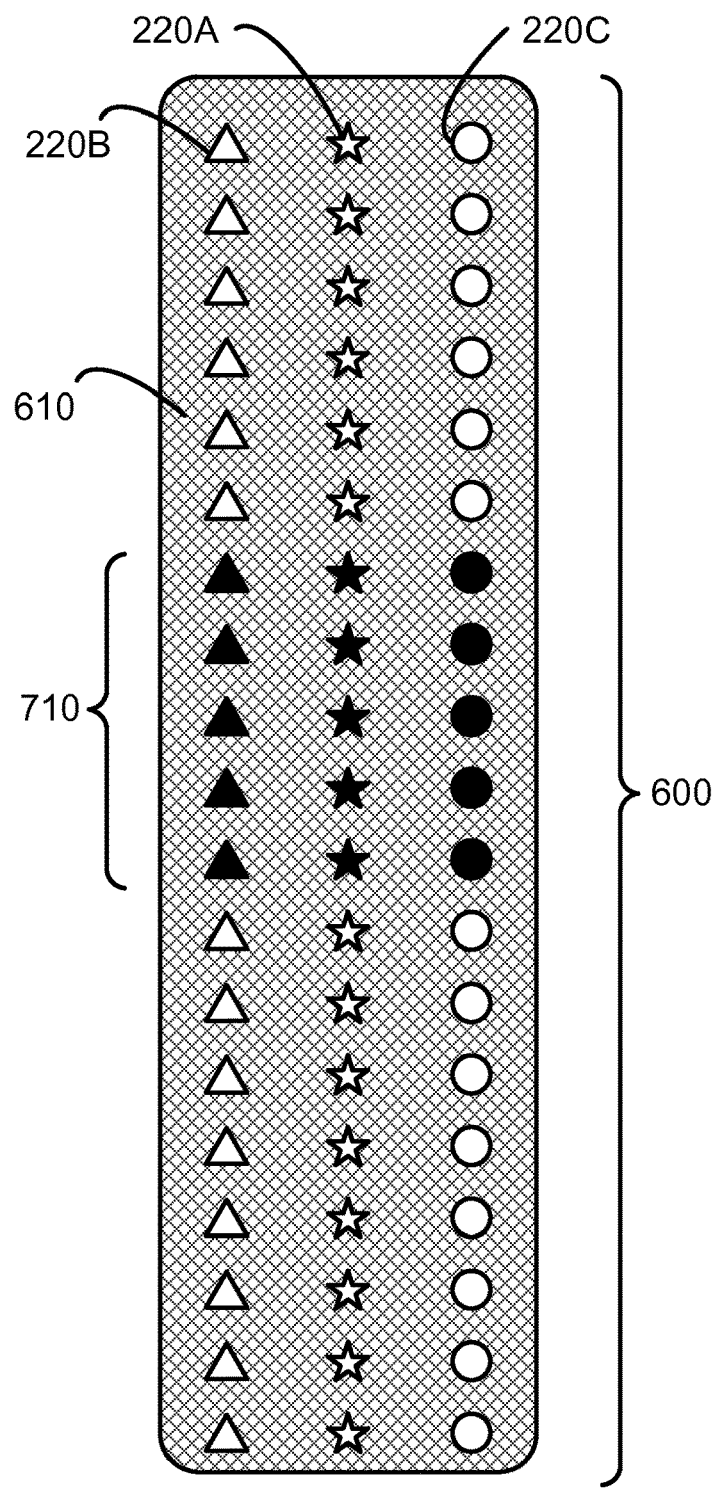
FIG. 8 depicts an appurtenance after removal from a cavity wound.

FIG. 8 depicts an appurtenance 600, such as shown in FIG. 6. The appurtenance 600 depicted in FIG. 8 is an appurtenance 600 that was packed and placed within a wound cavity, such as illustrated in FIG. 7, for a medically relevant period of time (e.g. 1 day, 2 days, 3 days, or 4 days), but has since been removed and placed on a substantially flat surface. The appurtenance 600 in FIG. 8 is a substantially planar, elongated structure including a substrate 610 with an array of attached sensor units 220. At least some of the sensor units 220 attached to the appurtenance 600 shown in the embodiment depicted in FIG. 8 include detectors with indicators that form visible color changes in the presence of a specific analyte. A section 700 of the appurtenance 600 includes sensor units 220 that have detected the presence of one or more specific analytes, and the corresponding indicators of the sensor units have been activated. FIG. 8 illustrates this with the sensor units 220 in the section 700 illustrated as colored markings. The three types of sensor units 220A, 220B and 220C located in the section 700 all indicate that they have detected the presence of their respective analytes. In some embodiments, the detectors in different types of sensor units can detect related analytes, such as proteins characteristic of a chronic wound, or an infection. In addition or alternatively, a sensor unit 220 can include a detector of excessive wound exudate, or biomarkers indicating the presence of excessive levels of wound exudate. In addition or alternatively, a sensor unit 220 can include a detector of excessive physical pressure with an indicator that forms visible color changes in the presence of excess pressure. For example, a sensor unit 220 can include a detector of excessive physical pressure with a compartment of colored dye configured to rupture in the presence of excess pressure, creating a visible marking on the appurtenance 600 at that location. The regionalized indicators of the appurtenance 600 provide local information to a caregiver about the localized conditions of a wound region within a cavity wound (see, e.g. FIG. 7). Such a location within a cavity wound may not be easily visible or observable during wound care, and can assist medical caregivers to understand local wound conditions with the potential for altering the wound care plan if necessary.

In some embodiments, an appurtenance 600 can be removed from a cavity wound and visually inspected for changes, such as the color changes illustrated in FIG. 8. In some embodiments, an appurtenance 600 is removed from a cavity wound and examined for changes in one or more sensor units with a detection device. For example, in some embodiments a sensor unit can include a detector that reflects a particular wavelength of light differently when an analyte from a cavity wound is detected. A detection device can include a transmitter of the appropriate light wavelength as well as a receiver to detect the reflection from the appurtenance. For example, in some embodiments a sensor unit can include a color indicator of a detection, and a detection device can emit light of a wavelength to detect the reflected color of the indicator. See, for example: US Patent Application Publication No. 2007/0269851, "Colorimetric Substrates, Colorimetric Sensors, and Methods of Use," to Sanders et al.; and US Patent Application Publication No. 2009/0299161, "Marker of Wound Infection," to Cullen et al., which are each incorporated by reference herein. For example, in some embodiments a sensor unit can include a passive RFID device, and a detection device can include an RFID transmitter and receiver.

Figure 9:
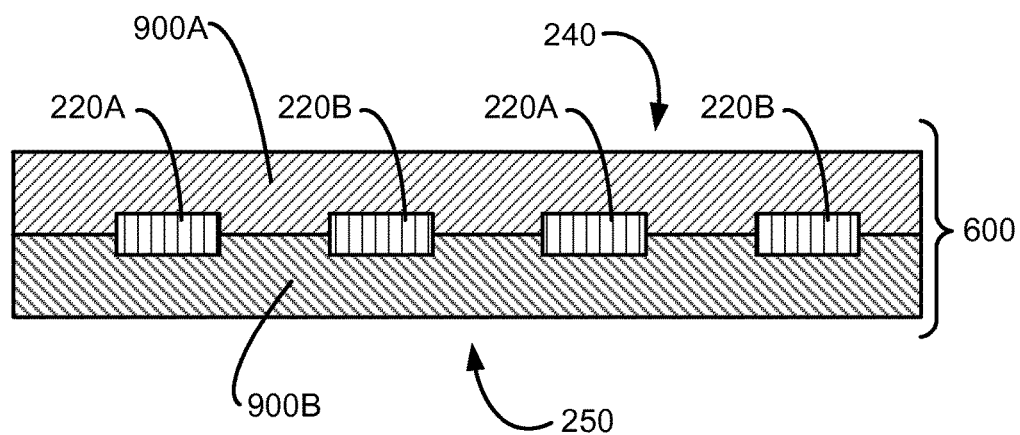
FIG. 9 shows a cross-section view through an appurtenance.

FIG. 9 depicts a region of an appurtenance 600 to a wound dressing in cross-section. The appurtenance 600 depicted includes two substrate layers 900A, 900B. In some embodiments, a substrate of an appurtenance includes a plurality of layers. The substrate layers 900A, 900B are fabricated from fluid-permeable, substantially flexible materials that are durable under physiological conditions within a cavity wound over the time period of expected use of the appurtenance 600. The combination of layers, 900A, 900B, create a substantially fluid-permeable appurtenance 600. The substrate material is also bio-compatible with the cavity wound. The substrate material should not, for example, lead to an allergic reaction or severe inflammatory response under expected use conditions. The substrate material can, for example, be fabricated from non-allergenic or low toxicity materials, including hypoallergenic foam, nylon, or cotton. In some embodiments, the substrate layers 900A, 900B within an appurtenance 600 are fabricated from the same materials. In some embodiments, the substrate layers 900A, 900B within an appurtenance 600 are fabricated from different materials. As shown in FIG. 9, the two substrate layers 900A, 900B are affixed to each other at a surface of each of the substrate layers 900A, 900B. A series of sensor units 220 are affixed within the substrate layers 900A, 900B. For example, the substrate layers 900A, 900B can be affixed to each other and to the sensor units 220 with adhesive. For example, the substrate layers 900A, 900B can be affixed to each other and to the sensor units 220 with fasteners. The sensor units 220 can be of two or more types, and positioned within the appurtenance 600 to form an array or pattern relative to the structure of the appurtenance 600. For example, FIG. 9 represents that the sensor units 220 can include two types of sensor units 220A, 220B that are arranged as a sequential, repeating pattern within an array of sensor units 220 (i.e. 220A, 220B, 220A, 220B . . . ). One or more layers 900A, 900B of the substrate of the appurtenance 600 can include embedded structures configured to direct fluid to a surface of a sensor unit 220. For example, a layer 900 can include channels or grooves positioned to direct fluid flow between a region adjacent to the appurtenance 600 and a surface of a sensor unit 220. For example, a layer 900 can include a plurality of unidirectional fluid flow structures positioned to direct fluid flow from a surface 240, 250 of the appurtenance 600 to a surface of a sensor unit 220. See, for example, U.S. Pat. No. 6,420,622 to Johnston et al., "Medical Article Having Fluid Control Film," which is incorporated herein by reference. The appurtenance 600 includes a cavity wound-facing surface 250 and a cavity-facing surface 240. The cavity wound-facing surface 250 can be configured for attachment of a primary wound dressing. The cavity-facing surface 240 can be configured for attachment to a primary wound dressing. For example, a surface 240, 250 can include fastening units to secure a wound dressing relative to the appurtenance 600 surface 240, 250.

Figure 10:
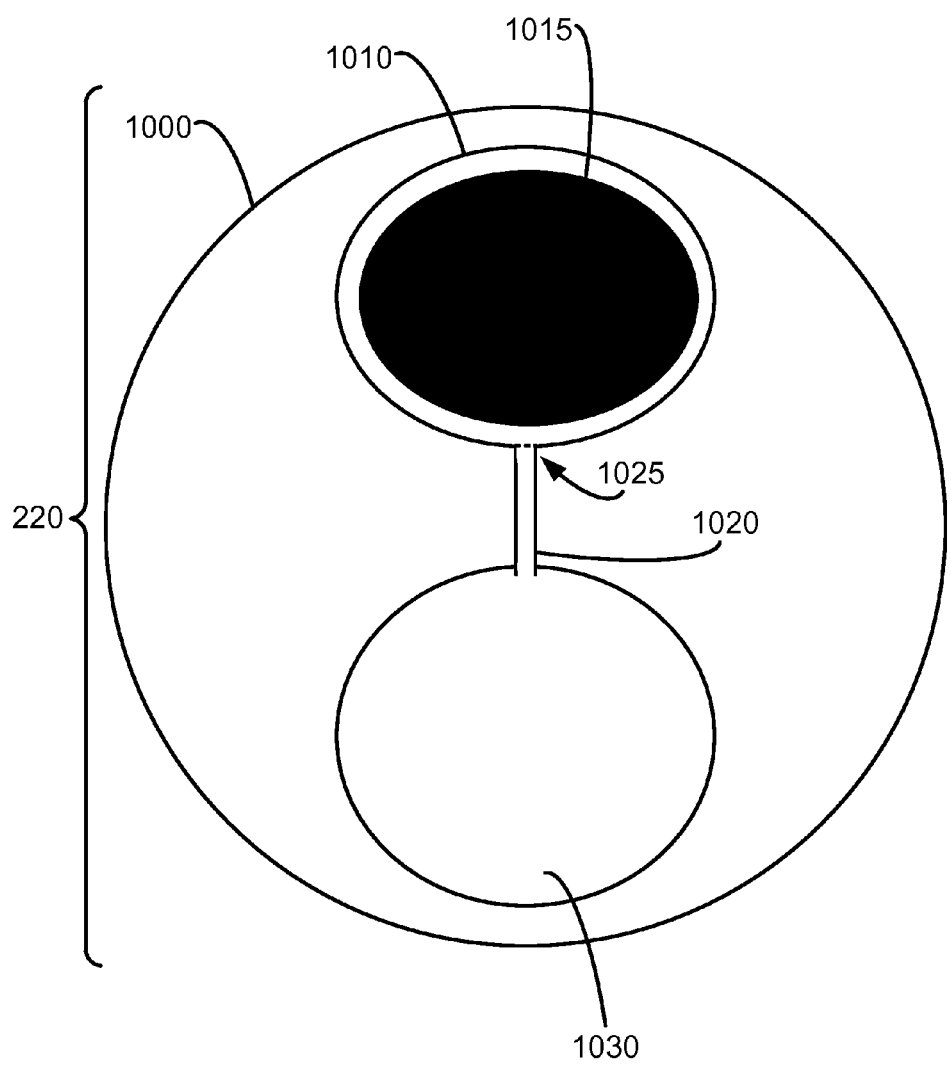
FIG. 10 illustrates a sensor unit.

FIG. 10 illustrates aspects of a sensor unit 220. The sensor unit 220 is shown in a top-down viewpoint, or a similar viewpoint as in FIGS. 2A, 6 and 8. A sensor unit 220 is configured to be attached to an appurtenance to a cavity wound dressing. The sensor unit 220 should, therefore, be of a size, mass and durability to be functional during use of the appurtenance. A sensor unit 220 should be of a size, shape and mass to not place undue strain or physical stress on a wound surface of a cavity wound during use. The sensor unit 220 includes an enclosure 1000. An enclosure 1000 can be fabricated from a material suitable to the embodiment, for example a soft plastic material. An enclosure 1000 can be fabricated from a biocompatible material, such as a medical grade silicone material. In some embodiments, the sensor unit 220 is configured to be flexible, and the enclosure 1000 correspondingly fabricated from a flexible material. In some embodiments, the enclosure includes one or more deformable regions. In some embodiments, the enclosure includes one or more transparent regions. In some embodiments, the enclosure includes one or more translucent regions.

The sensor unit 220 shown in FIG. 10 includes a detector 1010 of physical pressure. The detector 1010 includes a deformable cover enclosing an interior space including a marker fluid 1015. The deformable cover is of a size, shape and flexibility to deform in the presence of physical pressure on the external surface of the detector 1010. Depending on the embodiment, the deformable cover in association with the enclosure 1000 of the sensor unit 220 can be configured to deform in response to varying levels of physical pressure against the surface of the enclosure 1000 and the detector 1010. For example, the deformable cover of the detector 1010 can be configured to be compressed in response to physical pressure from the exterior of the sensor unit 220 at a pressure level that is considered to be medically undesirable to a cavity wound. In some embodiments, the deformable cover of the detector 1010 is configured to compress at an external pressure of approximately 32 mm Hg. In some embodiments, the deformable cover of the detector 1010 is configured to compress at an external pressure of approximately 20 mm Hg. In some embodiments, the deformable cover of the detector 1010 is configured to compress at an external pressure of approximately 10 mm Hg. In some embodiments, the deformable cover of the detector 1010 is configured to compress at an external pressure of approximately 40 mm Hg.

The sensor unit 220 includes a conduit 1020 connecting the interior of the detector 1010 and the interior of the indicator 1030. A marker fluid retention element 1025 is positioned within the conduit 1025 to retain the marker fluid 1015 within the detector 1010 when the deformable cover is not compressed. The marker fluid retention element 1025 is configured to allow marker fluid 1015 to move through the conduit 1020 in response to physical pressure from the deformable cover transmitted to the marker fluid 1015. The marker fluid 1015 can then enter the interior region of the indicator 1030.

Additionally or alternatively, other types of sensors of physical pressure, such as piezoelectric-based pressure sensors or capacitance-based pressure sensors, can be included in one or more sensor units. Some embodiments also include a sensor unit that includes an accelerometer.

Figure 11:
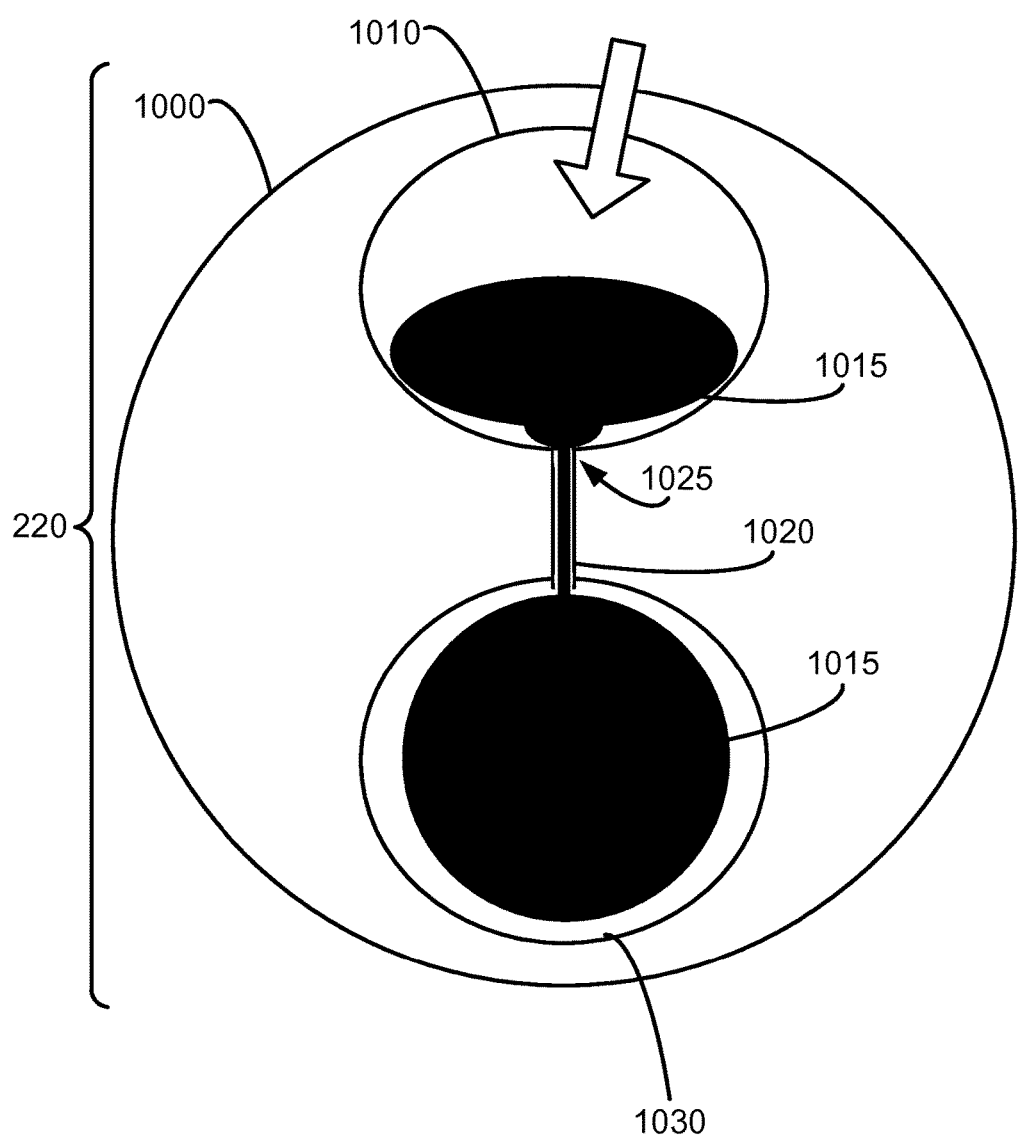
FIG. 11 depicts a sensor unit.

FIG. 11 illustrates aspects of a sensor unit 220 such as shown in FIG. 10. In the view shown in FIG. 11, the deformable cover of the detector 1010 has been subject to physical pressure (depicted by the large arrow) and the cover has compressed, transmitting physical pressure to the marker fluid 1015. The physical pressure on the marker fluid 1015 has caused the marker fluid 1015 to move through the conduit 1020 and into an interior region of the indicator 1015. The marker fluid retention element 1025 has permitted the flow of the marker fluid 1015 through the conduit 1020 in response to the physical pressure. For example, the marker fluid retention element 1025 can be configured to bend or flex away from the flow of marker fluid 1015, such as a flexible butterfly valve. For example, the marker fluid retention element 1025 can include a thin film configured to rupture in response to sufficient physical pressure from the marker fluid 1015. In some embodiments, the conduit 1020 includes a unidirectional flow structure. See, for example, U.S. Pat. No. 6,420,622 to Johnston et al., "Medical Article Having Fluid Control Film," which is incorporated herein by reference.

As shown in FIG. 11, the marker fluid 1015 has moved through the conduit 1020 and into the interior region of the indicator 1030. The indicator 1030 is fabricated from a material that allows for observation of the marker fluid 1015 within the interior region of the indicator 1030. For example, if the marker fluid 1015 is a colored liquid, the indicator 1030 can be fabricated from a transparent or translucent plastic material. For example, if the marker fluid 1015 is a magnetic fluid, the indicator 1030 can be fabricated from a non-magnetic material. For example, if the marker fluid 1015 is florescent, the indicator 1030 can be fabricated from a material that is transparent or translucent at the wavelength of the fluorescence. Correspondingly, a region of the enclosure 1000 adjacent to the indicator 1030 can be fabricated from a material that allows for observation of the marker fluid 1015 within the interior region of the enclosure and the indicator 1030. The indicator color can then be visualized by an outside observer. See, e.g. FIG. 8.

Figure 12:
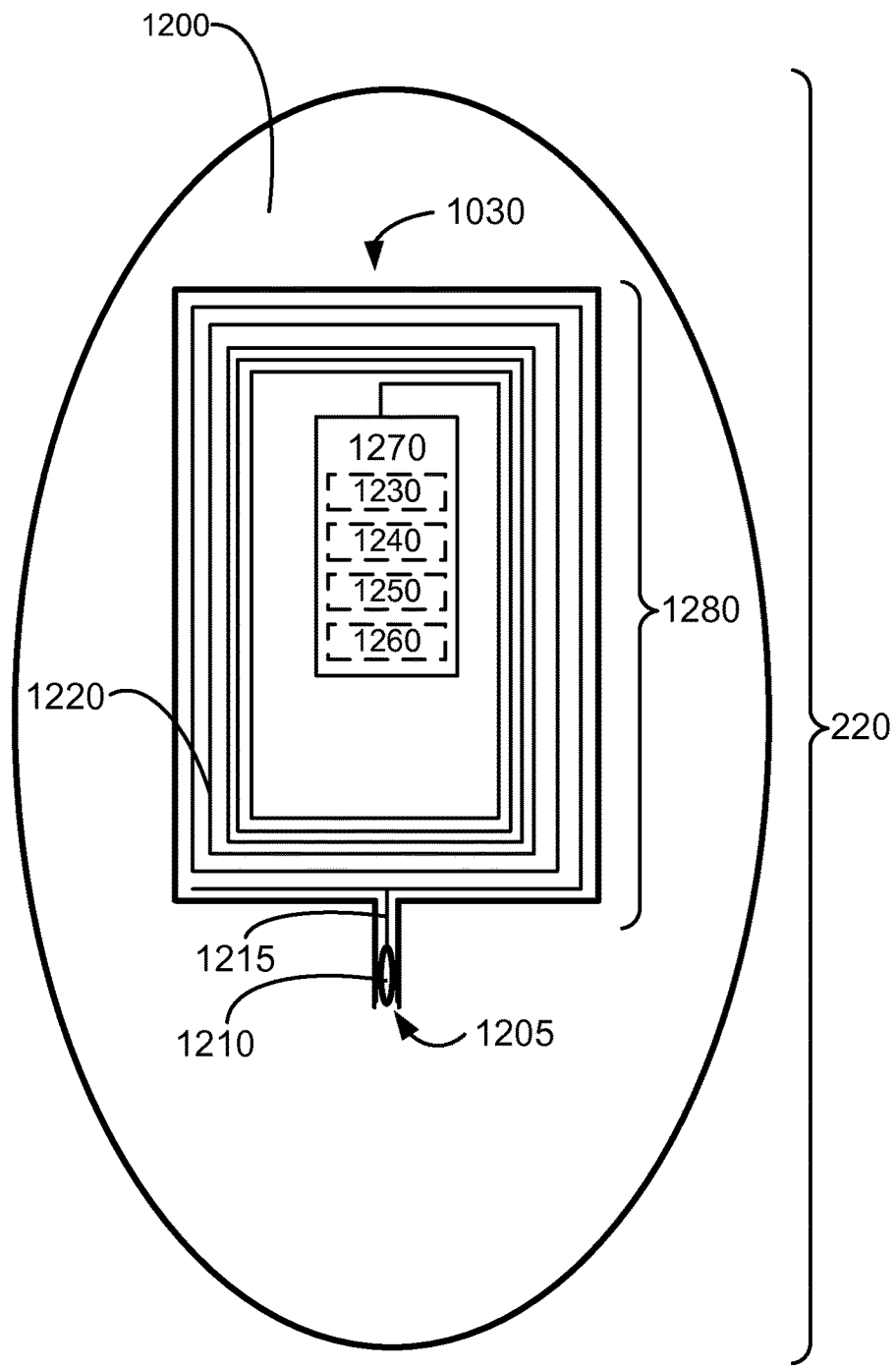
FIG. 12 shows a sensor unit.

FIG. 12 illustrates aspects of a sensor unit 220. The view illustrated in FIG. 12 is a substantially top-down view, as seen from the top of a sensor unit 220 looking down on to the unit. As shown in FIG. 12, sensor unit 220 includes a structural support 1200. The sensor unit 220 illustrated includes a structural support 1200 configured to provide shape and support to the sensor unit 220. The structural support 1200 can include, for example, a flexible plastic, which can be configured in a thin film or as a mesh of no more than a few millimeters (mm) in thickness. For example, the structural support 1200 can be no more than 3 mm, or no more than 5 mm, thick depending on the embodiment. The structural support 1200 can include, for example, a flexible paper material. The structural support 1200 can include, for example, a composite material. The structural support 1200 can include, for example, one or more materials with properties such as durability, strength, cost, weight, bio-compatibility and disposability that are suitable for a given embodiment. The structural support 1200 is configured to irreversibly attach to an appurtenance. In some embodiments, a sensor unit 220 is modular and the structural support 1200 is configured to attach to a substrate of an appurtenance, such as with adhesive or barbed fasteners. For example, the structural support 1200 can include an adhesive material on the face configured to conform to the surface of the appurtenance. For example, the structural support 1200 can include one or more barbs, hooks or other projections on the face configured to conform to the surface of the appurtenance. The structural support 1200 can include, for example, a cover configured to seal the structural support 1200 to a substrate of an appurtenance. For example, the structural support 1200 can include a cover configured to prevent wetness, debris, dirt or microbial agents from travelling between the structural support 1200 and a substrate of an appurtenance.

The sensor unit 220 illustrated in FIG. 12 includes a detector 1210 positioned within a conduit 1205. The conduit 1205 is configured to draw fluid, such as wound exudate, from the wound-facing side of the appurtenance, and therefore to draw analytes present in the wound fluid and/or wound exudate into the sensor unit 220 in proximity to the detector 1210. The detector 1210 is configured to send a signal via wire connector 1215 to the indictor 1030 that includes a transmission unit 1280.

Also as illustrated in FIG. 12, the sensor unit 220 includes an indicator 1030 that includes a transmission unit 1280 attached to a surface of the structural support 1200. The transmission unit 1280 includes circuitry 1270 and at least one antenna 1220. Although the transmission unit 1280 is illustrated as visible in FIG. 12, in some embodiments all or part of the transmission unit 1280 will be covered and not be visible. The transmission unit 1280 is configured to transmit a signal. In some embodiments, the transmission unit 1280 is configured to transmit a signal in response to a received signal (e.g. as a passive RFID). In some embodiments, the transmission unit 1280 is configured to transmit a signal without having received a signal. For example, the transmission unit can be operably connected to a power source, such as a battery. As illustrated in FIG. 12, an antenna 1220 can be a substantially planar antenna, such as commonly used in radio frequency identification (RFID) or near field communication (NFC) units. Prior to use, the antenna 1220 can be detuned with a removable surface layer of a conductive material. This can be desirable to reduce excess RFID signals, for example from appurtenances in storage prior to use. See U.S. Pat. No. 7,724,136 to Posamentier, titled "Revealable RFID Devices," which is incorporated herein by reference. The circuitry 1270 of the transmission unit 1280 can include a variety of components, as desired in a particular embodiment. The circuitry 1270 of the transmission unit 1280 can include a processor 1230. The circuitry 1270 can include non-volatile memory 1240. The circuitry 1270 can include a transmitter 1250. The circuitry 1270 can include one or more additional modules 1260. For example, the circuitry 1270 can include an energy source, such as a battery. For example, the circuitry 1270 can include a receiver. For example, the circuitry 1270 can include a transceiver. For example, the circuitry 1270 can include an additional antenna. For example, the circuitry 1270 can include volatile memory. The circuitry 1270 can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference.

In some embodiments, an indicator that includes a transmission unit can include a pressure sensitive activation region, wherein the pressure sensitive activation region is configured to be activated by physical pressure between a surface of the substrate and a surface of the appurtenance. In some embodiments, the indicator that includes a transmission unit can include a pressure sensitive activation region, wherein the pressure sensitive activation region is configured to be activated by physical pressure on a surface of the appurtenance. In some embodiments, the indicator that includes a transmission unit can include a pressure sensitive activation region, wherein the pressure sensitive activation region is configured to be activated by physical pressure between a surface of the substrate and a surface of the wound dressing. See, for example, U.S. Pat. Nos. 6,693,513 and 6,037,879 to Tuttle, titled "Wireless Identification Device, RFID Device with Push-On/Push-Off Switch, and Method of Manufacturing Wireless Identification Device," and U.S. Pat. No. 6,863,220 to Selker, titled "Manually Operated Switch for Enabling and Disabling an RFID Card," as well as Sample et al., "A Capacitive Touch Interface for Passive RFID Tags," 2009 *IEEE International Conference on RFID*, 103-109 (2009), which are each incorporated herein by reference.

Figure 13:
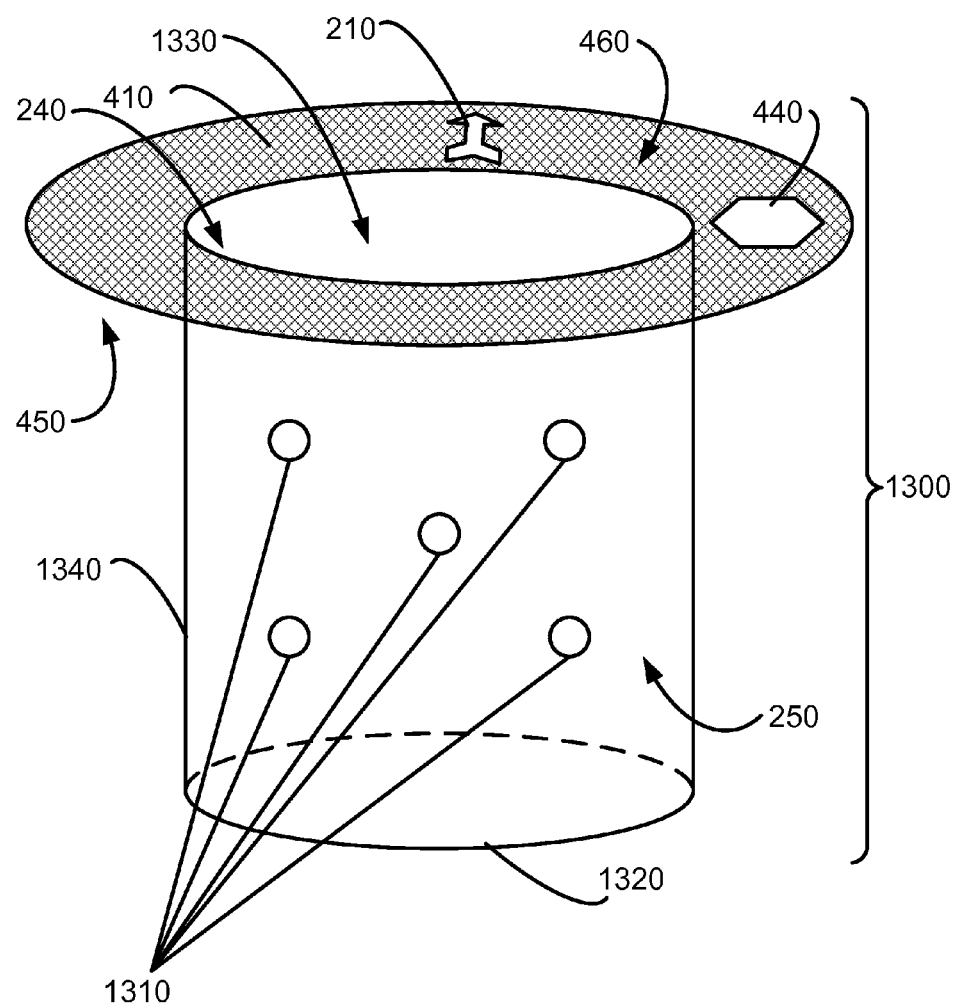
FIG. 13 illustrates an appurtenance to a cavity wound dressing.

FIG. 13 illustrates aspects of an appurtenance 1300 configured for use in a cavity wound. The appurtenance 1300 includes an edge region 410, the edge region including a surface 450 positioned to be adjacent with the surface region of the periwound region when the appurtenance 230 is in use. The edge region 410 also includes a surface 460 positioned to be distal to the surface region of the periwound region when the appurtenance 230 is in use. The surface 460 of the edge region 410 of the appurtenance 1300 includes an attached orientation indicator 210. The surface 460 of the edge region 410 also includes a temperature sensor unit 440. The temperature sensor unit 440 is configured to detect the temperature of a surface region of the periwound region when the appurtenance 230 is in use. See U.S. Pat. No. 6,963,772, and US Patent Application Publication No. 2006/0047218, each titled "User-Retainable Temperature and Impedance Monitoring Methods and Devices," each to Bloom, which are each incorporated by reference. The temperature sensor unit 440 can be configured to detect the temperature of a surface region of the periwound region. Detected temperature information can, for example, be recorded, such as in an associated memory device, over time. Detected temperature information can, for example, be transmitted by an associated transmission unit. For example, the temperature sensor unit 440 record can be configured for use in comparison with a temperature record from a sensor unit attached to the substrate positioned within a wound cavity.

The appurtenance 1300 shown in FIG. 13 includes a substrate including a structural side wall 1340 and a structural lower wall 1320, the structural side wall 1340 and the structural lower wall 1320 configured to conform in shape with an interior of a cavity of a cavity wound. The structural side wall 1340 and the structural lower wall 1320 illustrated in FIG. 13 are in a substantially cylindrical shape, to conform with a substantially cylindrical cavity wound. The structural side wall 1340 and the structural lower wall 1320 form an interior space 1330 of the appurtenance 1300. Other configurations are possible to conform with the shapes of cavity wounds of non-cylindrical shapes. For example, an appurtenance can be configured as a circular, oblong, or irregular shape. In the embodiment illustrated in FIG. 13, the appurtenance is fabricated from a flexible but substantially firm material, configured to substantially retain its size and shape during use in a cavity wound. The structural side wall 1340 and the structural lower wall 1320 include a plurality of apertures 1310 penetrating from the wound-facing surface 250 of the appurtenance 1300 to the cavity-facing surface 240. Although five apertures 1310 are illustrated, in some embodiments there will be fewer than five or greater than five apertures 1310. In some embodiments, the apertures are positioned on regions of the appurtenance 1300 corresponding to regions of the cavity wound surface where enhanced monitoring is desirable. For example, a region of a cavity wound surface adjacent to a bone may require closer monitoring than other regions of the cavity wound surface, and an appurtenance can include apertures in the region corresponding to the cavity wound surface adjacent to the bone. For example, a region of a cavity wound surface adjacent to a region that has been bleeding may require closer monitoring than other regions of the cavity wound surface, and an appurtenance can include apertures in the region corresponding to the cavity wound surface at the recently bleeding, and therefore fragile, region of the cavity wound surface.

In some embodiments, an appurtenance to a cavity wound dressing includes a substrate including at least one wound-facing surface, the wound-facing surface of a size and shape for positioning within a cavity wound, wherein the substrate includes a plurality of apertures; and a plurality of sensor units attached to the substrate, each of the plurality of sensor units oriented and positioned on the substrate relative to at least one of the plurality of apertures.

In some embodiments, a substrate to an appurtenance includes a structure including the wound-facing surface of a size and shape to approximate the surface of the cavity wound with a gap between the wound-facing surface of the substrate and a cavity wound surface. In some embodiments, a substrate to an appurtenance includes a three dimensional structure with at least one wound-facing surface, the at least one wound-facing surface of a size and shape to reversibly mate with the wound surface of the cavity wound. In some embodiments, a substrate to an appurtenance includes a non-porous, flexible structure. For example, the substrate can be fabricated from a non-porous medical grade silicone. In some embodiments, a substrate to an appurtenance includes a porous, flexible structure. For example, the substrate can be fabricated from a medical grade silicone including a plurality of pores through the substrate. In some embodiments, a substrate to an appurtenance includes an interior region within the substrate, the interior region including one or more of the plurality of sensor units. In some embodiments, a substrate to an appurtenance includes a plurality of unidirectional fluid flow structures attached to the apertures, wherein the unidirectional fluid flow structures are configured to allow fluid flow from the wound-facing surface to one or more of the plurality of sensor units attached to the substrate.

In some embodiments, the plurality of sensor units attached to the substrate include a plurality of sensor units of at least two distinct types oriented as a pattern relative to the wound-facing surface. For example, the plurality of sensor units can be oriented in a "checkerboard" pattern, or an alternating array. In some embodiments, the plurality of sensor units attached to the substrate include a plurality of sensor units including at least one sensor unit configured to detect physical pressure or temperature over time. For example, the at least one sensor unit configured to detect physical pressure or temperature over time can be configured to detect physical pressure or temperature over minimum threshold values. For example, the at least one sensor unit configured to detect physical pressure or temperature over time can be configured to indicate a composite value for detected physical pressure or temperature.

In some embodiments, the plurality of sensor units attached to the substrate include at least one antenna operably attached to at least one sensor unit. In some embodiments, the plurality of sensor units attached to the substrate include at least one chemical-based sensor unit. In some embodiments, the plurality of sensor units attached to the substrate include at least one positional indicator. In some embodiments, the plurality of sensor units attached to the substrate include at least one fluid-activated sensor unit. In some embodiments, the plurality of sensor units attached to the substrate include at least one sensor unit including an optically resolvable detection indicator. For example, a sensor unit can include an indicator that changes color after detection of a condition, such as the presence of an analyte. In some embodiments, the plurality of sensor units attached to the substrate include at least one sensor unit including a detection indicator with an RFID antenna.

In some embodiments, an appurtenance includes: an edge region of the appurtenance, the edge region including at least one surface configured to be oriented away from the wound; and at least one orientation indicator attached to the edge region. In some embodiments, an appurtenance includes: an edge region of the appurtenance, the edge region including at least one surface configured to be oriented away from the wound; and at least one temperature sensor unit attached to the edge region. For example, a temperature sensor unit can be configured to detect the surface temperature of the periwound region. In some embodiments, an appurtenance is functional when wet. For example, an appurtenance can be configured for use within a substantially damp wound cavity. For example, an appurtenance can be configured for use with a saline-soaked gauze primary dressing. For example, an appurtenance can be configured for use with a primary dressing including a hydrogel. In some embodiments, an appurtenance includes: a wound dressing, the wound dressing configured to be positioned within the wound cavity between the appurtenance and the wound surface; and a second wound dressing, the second wound dressing configured to cover a wound region and stabilize the appurtenance and the wound dressing during use, the second wound dressing configured to be removable from the wound region after use. In some embodiments, an appurtenance includes: a detachable cover configured to reversibly mate with the at least one wound-facing surface of the substrate.

Figure 14:
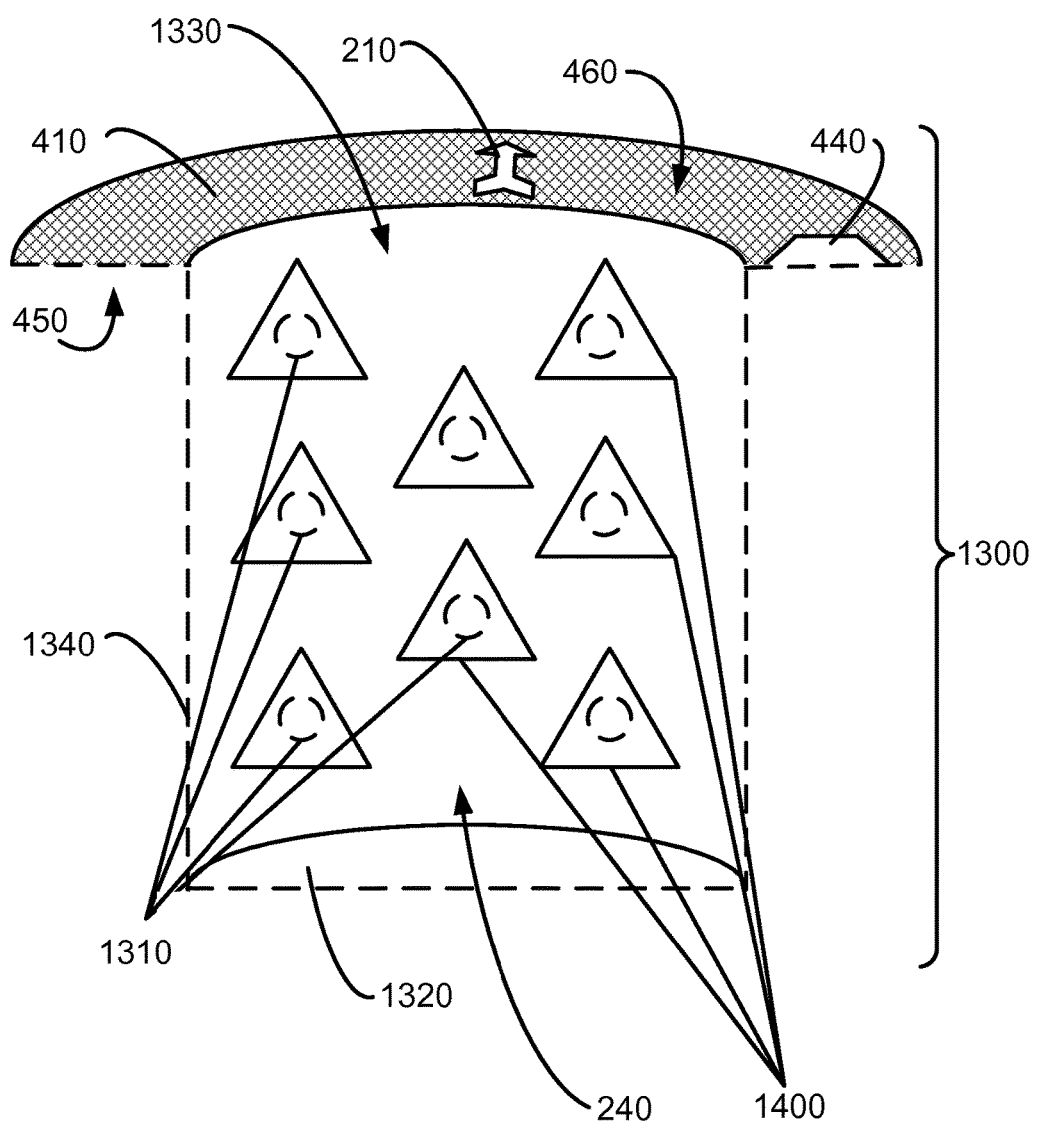
FIG. 14 depicts, in cross-section, an appurtenance.

FIG. 14 illustrates aspects of an appurtenance 1300 such as the one illustrated in FIG. 13, depicted in vertical cross-section. The structural side wall 1340 and the structural lower wall 1320 are shown in vertical section to illustrate the interior space 1330 of the appurtenance 1300. A plurality of apertures 1310 are positioned on the structural side wall 1340, the apertures 1310 positioned to allow fluid flow from the wound-facing surface of the appurtenance to the cavity-facing surface 240. Each of the apertures 1310 has a corresponding sensor unit 1400 associated with the aperture 1310, each of the sensor units 1400 affixed to the cavity-facing surface 240. In the embodiment illustrated, the apertures 1310 are positioned and sized to allow fluid flow directly from the wound surface region to the sensor units 1400 attached to the cavity-facing surface 240 of the appurtenance 1300. The sensor units 1400 can include, for example, a detector positioned within a conduit. See, e.g. FIG. 12. This embodiment can, for example, be used with a primary dressing within the interior space 1330 of the appurtenance 1300. Medicament, such as saline solution or alginate, can move across the porous structure of the structural side wall 1340 and the structural lower wall 1320 of the appurtenance 1300. Analytes from the wound surface will be detected regionally by each of the sensor units 1400 respectively affixed to the cavity-facing surface 240 in specific locations. This regional information can be useful to a caregiver, such as medical personnel, for monitoring therapy response by the cavity wound.

Figure 15:
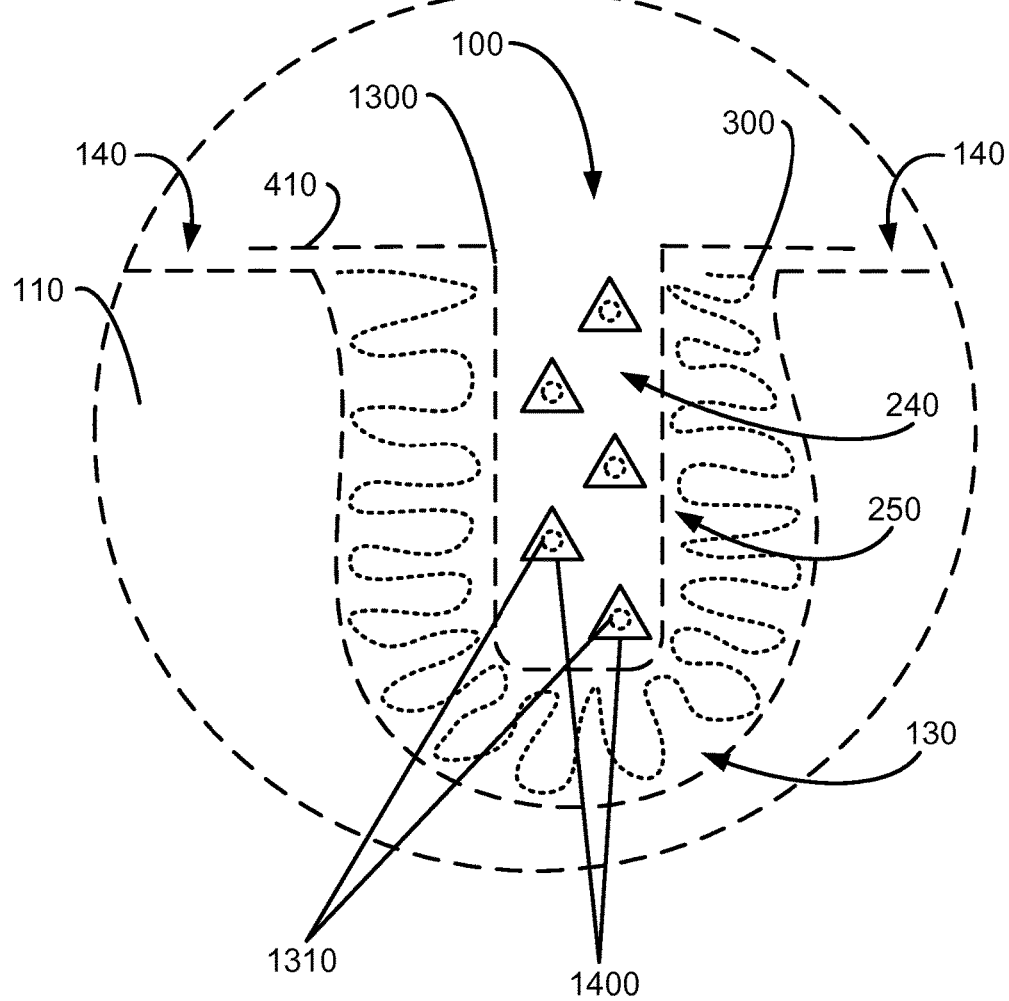
FIG. 15 shows, in cross-section, an appurtenance in use in a cavity wound with a wound dressing.

FIG. 15 illustrates a cross-section view of an embodiment of an appurtenance 1300 in situ within a cavity wound 100. The embodiment illustrated in FIG. 15 is similar to that shown in FIGS. 13 and 14, shown in FIG. 15 in situ within a cavity wound 100. FIG. 15 depicts that a wound dressing 300 is positioned within the cavity wound 100, adjacent to the wound surface 130. The appurtenance 1300 is positioned adjacent to the wound dressing 300 within the cavity wound 100. In the illustrated embodiment, the appurtenance 1300 includes a plurality of apertures 1310. Each of the apertures 1310 has a corresponding sensor unit 1400 associated with the aperture 1310, each of the sensor units 1400 affixed to the cavity-facing surface 240 of the appurtenance 1300. In the embodiment illustrated, each of the sensor units 1400 is positioned to detect and indicate the conditions, such as the presence of analytes, in the wound fluid and wound dressing fluid from the adjacent region of the wound dressing 300 and wound surface 130.

Figure 16A:
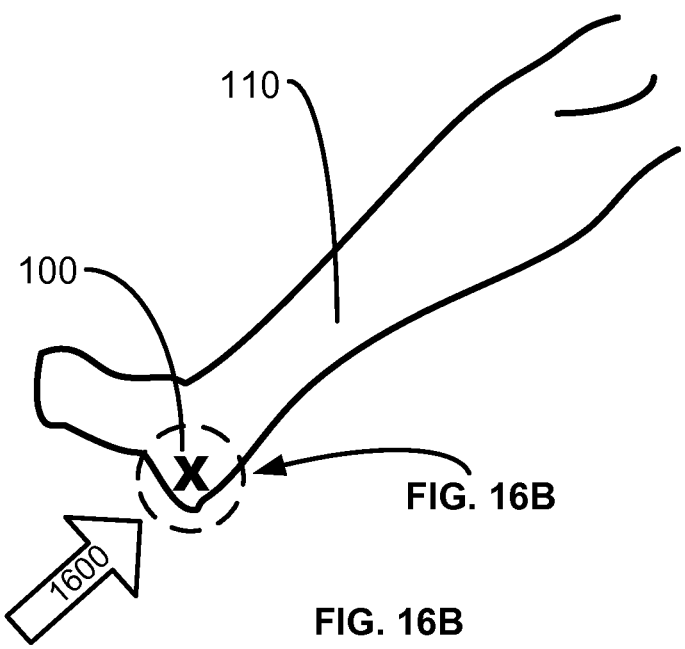
FIG. 16A illustrates a wound region on a human body part.

FIG. 16A illustrates aspects of a cavity wound 100 on a body part 110. As represented generally in FIG. 16A, in some medical situations a cavity wound 100 forms on the weight-bearing region of a body part 110, such as a heel. A cavity wound 100 on the weight-bearing region of a body part 110 can be further exacerbated by additional pressure, represented by force 1600, against the cavity wound 100. For example, the force 1600 can impede blood flow through the adjacent blood vessels, including through closure of capillaries. Medical caregivers often suggest reduced pressure for such wounds, but are unable to monitor the pressure received by the cavity wound over time during treatment with a conventional primary dressing. Some patients, such as those suffering from diabetic neuropathy, are unable to feel the pressure on the wound and, therefore, unwittingly damage the wound through routine activities that result in prolonged physical pressure at the cavity wound 100 site.

Figure 16B:
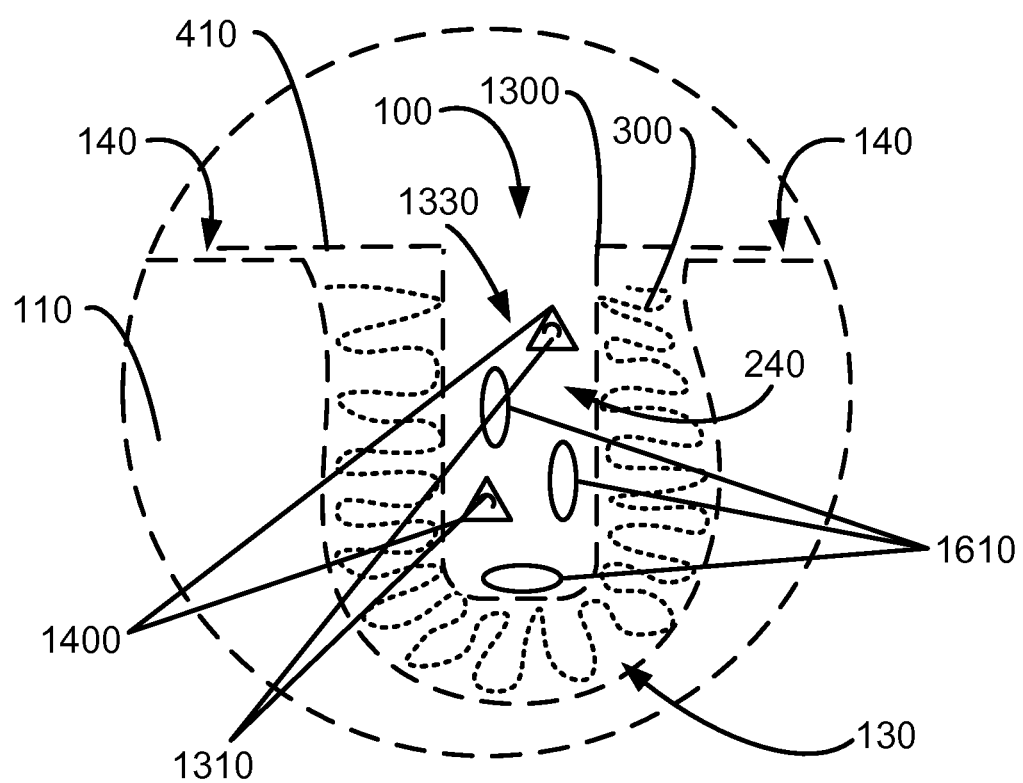
FIG. 16B depicts, in cross-section, a cavity wound with an appurtenance and a wound dressing in the wound region shown in FIG. 16A.

FIG. 16B shows a cross-section view of an embodiment of an appurtenance 1300 in situ in a cavity wound 100. The appurtenance 1300 includes an edge region 410 positioned adjacent to the periwound surface 140 in situ. The cavity wound 100 includes a wound dressing 300 positioned within the cavity wound 100 adjacent to the wound surface 130. The appurtenance 1300 includes a plurality of sensor units 1400 configured to detect analytes, the sensor units 1400 attached to the interior surface 240 of the appurtenance 1300. Each of the sensor units 1400 is positioned adjacent to an aperture 1310 in the appurtenance 1300, the each of the apertures 1310 of a size, shape and position to allow fluid to flow through the appurtenance 1300 structure. In the embodiment illustrated, the appurtenance 1300 is fabricated from a substantially flexible material, the material capable of transmitting physical pressure from the body part 110 through the wound surface 130 to the appurtenance 1300. Attached to the appurtenance 1300 are a plurality of sensor units 1610 configured to detect physical pressure within the cavity wound 100. The plurality of sensor units 1610 configured to detect physical pressure within the cavity wound 100 can include, for example, one or more detectors of physical pressure. For example, the plurality of sensor units 1610 configured to detect physical pressure within the cavity wound 100 can be configured to detect physical pressure at capillary-closing levels, which can inhibit blood flow in the body part 110 and decrease physiological wound healing. For example, the plurality of sensor units 1610 configured to detect physical pressure within the cavity wound 100 can be configured to detect physical pressure at a level greater than 20 mm Hg. For example, the plurality of sensor units 1610 configured to detect physical pressure within the cavity wound 100 can be configured to detect physical pressure at a level greater than 15 mm Hg. For example, the plurality of sensor units 1610 configured to detect physical pressure within the cavity wound 100 can be configured to detect physical pressure at a level greater than 30 mm Hg. For example, the plurality of sensor units 1610 configured to detect physical pressure within the cavity wound 100 can be configured to detect physical pressure at a level greater than 35 mm Hg. For example, the plurality of sensor units 1610 configured to detect physical pressure within the cavity wound 100 can be configured to detect physical pressure at a level greater than 40 mm Hg. The plurality of sensor units 1610 configured to detect physical pressure within the cavity wound 100 can be configured to detect physical pressure over multiple time points and indicate a time-dependent pressure result. The plurality of sensor units 1610 configured to detect physical pressure within the cavity wound 100 can be configured to detect physical pressure over time and indicate the composite, average, or total pressure. In some embodiments, each of the plurality of sensor units 1400, 1610 indicate their own distinctive detection events. In some embodiments, each of the plurality of sensor units 1400, 1610 are connected to a common reporter unit that records and reports on the detection, or lack thereof, for each of the sensor units 1400, 1610.

In some embodiments, the appurtenance includes: a sensor unit including one or more detectors; an indicator including a transmission unit with a processor and at least one transmitter unit operably attached to the processor; and a connector between the sensor unit and the transmission unit, the connector configured to convey signals between the one or more detectors and the transmission unit. For example, the connector can include a wire. In some embodiments, the sensor unit is positioned adjacent to an opening in the appurtenance, the opening at a position to allow analytes to flow from the wound surface into a position in contact with the sensor unit.

In some embodiments, the sensor unit can be configured to be responsive to changes in circuitry capacitance. For example, in some embodiments the sensor unit is operably attached to a transmission unit via one or more connectors including wires. The transmission unit can include, for example, one or more antennas, a non-volatile memory, and related circuitry. The transmission unit can include, for example, an antenna and a receiver operably attached to the antenna. The transmission unit can include, for example, non-volatile memory. The transmission unit can include, for example, a substrate including at least one surface configured to conform to a surface of an appurtenance. For example, the transmission unit can, in whole or part, be attached to a cavity-facing surface of an appurtenance. The transmission unit can, in whole or part, be attached to an exterior surface of the edge region of the appurtenance. For example, in some situations the appurtenance is too small to accommodate the square area of the transmission unit, or where other space parameters make that option desirable. In some embodiments of an appurtenance, the transmission unit including at least one antenna is positioned adjacent to the periwound region, it can be desirable to include a self-compensating antenna system, such as described in U.S. Pat. No. 7,055,754 to Forester, titled "Self-Compensating Antennas for Substrates having Differing Dielectric Constant Values," which is incorporated herein by reference. In some embodiments, the appurtenance can include an indicator operably attached to the transmission unit. For example the appurtenance can include an indicator which is at least one of: a visual indicator, a haptic indicator, or an auditory indicator.

Figure 17:
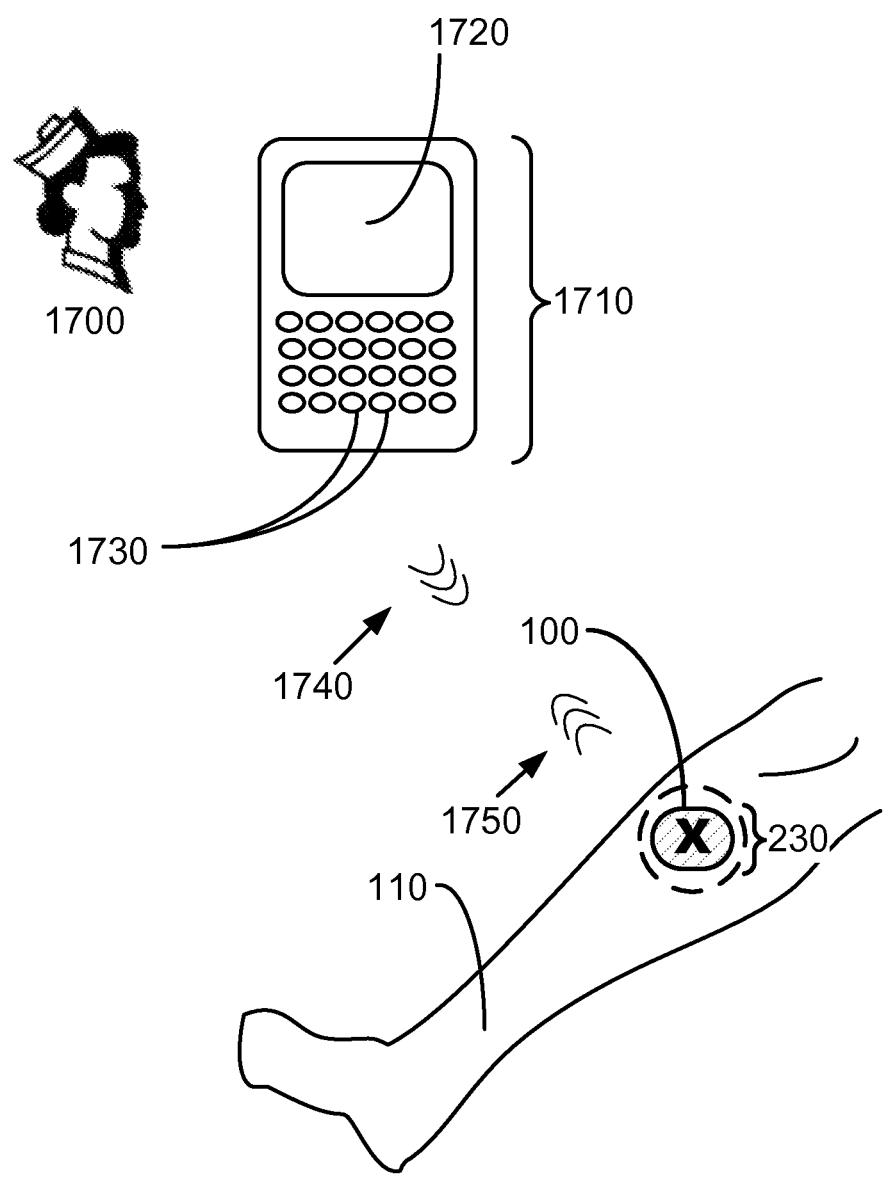
FIG. 17 illustrates an appurtenance to a cavity wound dressing in communication with a local unit.

FIG. 17 illustrates aspects of a system including a cavity wound 100 with an appurtenance 230 associated with a wound dressing. As shown in FIG. 17, a wound dressing with an associated appurtenance is placed over and within a cavity wound 100 on a body part 110 of a patient. For example, the body part 110 may have been subject to a surgery, and therefore to have an acute wound closing by primary intention. For example, the body part 110 can include an ulcer, and therefore have a chronic wound closing by secondary or tertiary intention. The appurtenance 230 associated with the wound dressing receives signals 1740 sent from a local unit 1710 and transmits signals 1750 to the local unit 1710. For example, the appurtenance 230 associated with the wound dressing can include a passive RFID configured to transmit signals 1750 after receiving signals 1740 from a proximal RFID reader device in the local unit 1710. The appurtenance 230 includes at least one transmission unit connected to a sensor unit. The local unit 1710 includes a receiver for the at least one transmission unit, at least one processor operably attached to the receiver, and at least one communication unit operably attached to the processor.

A local unit 1710 can include a handheld device. For example, the local unit 1710 can include a distinct handheld device. For example, the local unit 1710 can be included as part of a larger handheld unit, for example a tablet, a laptop, a cell phone, a personal communication device, or similar types of devices. A local unit 1710 can be integrated with an institutional furnishing, such as a hospital bed, a medical stand, a bedside table or a surgical cart. A local unit 1710 can be of a size, a shape and a configuration for portable handheld use. A local unit 1710 can be configured to be attached to a mobile unit, such as the end of a hospital bed, a medical stand, a bedside table, a wheelchair, or similar device. For example, a local unit can be integrated with a medical cart, as described in U.S. Pat. No. 7,667,606 to Packert et al., titled "RF Enabled Surgical Cart and Use of Same in Operating Room Environment," which is incorporated herein by reference. A local unit 1710 can be configured to be integrated into a furnishing. For example, a local unit 1710 can be integrated into a hospital bed, a bedside hospital monitor, a bedside table, a medical chair, a medical table, or similar furnishing. A local unit 1710 can be a wearable device, such as in association with a wristband, a waistband, or a strap. A local unit 1710 can be integrated with a wearable device used in conjunction with the appurtenance 230 and a wound dressing, such as a local unit integrated with a cover or wrapping placed over the cavity wound 100. A local unit 1710 can be a wearable device integrated into a wearable object, for example a vest or an armband. A local unit 1710 can be configured for integration into a wearable object for use by a patient, for example a vest worn by a patient with a cavity wound 100.

A local unit 1710 can include a display unit 1720. In some embodiments, there can be a secondary device configured to relay signals to the local unit 1710, for example as described in U.S. Pat. No. 7,986,235 to Posamentier titled "RFID Receive-Only System," which is incorporated herein by reference. A local unit 1710 can include a communication unit configured to send signals to a central assembly. The communication unit of a local unit 1710 can include at least one of: a visual display, a sound generator, a vibrating unit, and one or more light displays. A local unit 1710 can include at least one user interface, such as a screen, monitor, touchscreen or voice recognition element. A local unit 1710 can include an auditory signal generator. A local unit 1710 can include an input device 1730, for example a keyboard. Although the local unit 1710 illustrated in FIG. 17 includes a keyboard as an input device 1730, in some embodiments the input device 1730 can include other types of input devices, for example a touchscreen, stylus, keypad, or voice recognition system. A local unit 1710 can include a power source. For example, a local unit 1710 can include a solar cell, a battery or connect to a building power supply through a wire connection. A user 1700 operates the local unit 1710.

A user 1700 can include a medical caregiver, such as a nurse or doctor, or a patient, patient family member or other individual monitoring the wound dressing. Although user 1700 is shown/described herein as a single illustrated figure, the user 1700 can be representative of a human user, a robotic user (e.g., computational entity), and/or substantially any combination thereof (e.g., a user can be assisted by one or more robotic agents) unless context dictates otherwise. In general, the same can be said of "sender" and/or other entity-oriented terms as such terms are used herein unless context dictates otherwise. A user 1700 may utilize a local unit 1710 through a user interface, for example one or more buttons, a keyboard, a touchscreen, a voice recognition device, a stylus, or other means.

A local unit 1710 can include a communication device including at least one transmitter. A local unit 1710 can include a radio-frequency identification (RFID) receiver. A local unit 1710 can include a near field communication (NFC) device. A local unit 1710 can be configured to send and receive signals from a plurality of appurtenances. For example, a local unit 1710 can be configured to send and receive signals from multiple appurtenances affixed to wound dressings on a single individual. For example, a local unit 1710 can be configured to send and receive signals from multiple appurtenances affixed to wound dressings on multiple individuals in a defined area, such as a single room or region of a room. A local unit 1710 can be configured to send signals to one or more appurtenances 230 associated with cavity wound dressings automatically. For example, local unit 1710 can be configured to send signals to one or more appurtenances 230 associated with cavity wound dressings at least one of: every 30 minutes; every hour; every 2 hours; or every 3 hours. A local unit 1710 can be configured to send signals to one or more appurtenances 230 associated with cavity wound dressings on a schedule selected by the user 1700. For example, local unit 1710 can be configured to send signals to one or more appurtenances 230 associated with cavity wound dressings on at least one of: an hourly schedule; a schedule of every 30 minutes for 4 hours, followed by hourly signals; or a schedule provided by the user through the user interface (e.g. the keyboard 1730). A local unit 1710 can be configured to send signals to one or more appurtenances 230 associated with cavity wound dressings on a preset schedule which is selected by the user 1700. For example, local unit 1710 can be configured to send signals to one or more appurtenances 230 associated with cavity wound dressings on at least one of: a schedule preset to monitor a wound after surgery; a schedule preset to monitor a chronic wound; an hourly schedule; a schedule of every 2 hours; a schedule of hourly during the day and every 2 hours at night; or other preset schedules.

The signals 1740 sent from the local unit 1710 to the appurtenances 230 associated with cavity wound dressings can be radio frequency signals in a particular wavelength, or range of wavelengths. For example, the signals can be in the UHF range, such as a UHF sub-range commonly used in a particular geographic region. See, for example the "Worldwide RFID UHF Map" by Intelleflex Corporation (©2009), which is incorporated herein by reference. For example, the signals can be in a range of 902-928 MHz. For example, the signals can be in a range specified by an industry standard. For example, the signals can be in the approximately 13.56 megahertz (MHz) range, or within the ISO 14443 standard parameters. For example, the signals can be in the IEEE 802.11x standard or the Bluetooth standard range. See, for example, U.S. Pat. No. 7,215,976 to Brideglall, titled "RFID Device, System and Method of Operation Including a Hybrid Backscatter-based RFID Protocol Compatible with RFID, Bluetooth and/or IEEE 802.11x Infrastructure," which is incorporated herein by reference. For example, the signals can be in the approximately 131 kilohertz (KHz) range, for example as part of a RuBee™ (IEEE standard 1902.1) system (equipment sold, for example, by Visible Assets™, Inc). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference.

Similarly, the signals 1750 sent from the appurtenance 230 associated with a cavity wound dressing to the local unit 1710 can be one of the types described above in relation to signals 1740 sent from the local unit 1710. In some embodiments, the appurtenance 230 associated with a cavity wound dressing includes a backscatter or reflective transmission device, and so the signals 1750 sent from the appurtenance 230 associated with the cavity wound dressing to the local unit 1710 can be backscatter or reflective signals. For example, as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference herein.

The signals 1740 transmitted from the local unit 1710 or the signals 1750 transmitted from the appurtenance 230 associated with a cavity wound dressing can be sent in a fixed direction from the signal source. The appurtenance 230 and the local unit 1710 may each include markings or other visible aspects directing a user how as to orient the appurtenance 230 and the local unit 1710 relative to each other for signal directionality. For example, an appurtenance 230 can include a positional identifier on an edge region. For example, an appurtenance 230 can include an orientation marker on an edge region.

In many embodiments, it is envisioned that the signal strength of a signal 1740 transmitted from the local unit 1710 or a signal 1750 transmitted from an appurtenance 230 will be such that the signal 1740, 1750 will not travel a significant distance. The local unit 1710 and the appurtenance 230 may, therefore, need to be placed in reasonably close proximity for signals 1740, 1750 to travel between the devices. For example, the signal 1740, 1750 transmitted from either the local unit 1710 or transmitted from the appurtenance 230 can be such that the receiver of such signals should be within the same room. For example, the signal 1740, 1750 transmitted from either the local unit 1710 or transmitted from the appurtenance 230 can be such that the receiver of such signals should be within 10 feet. For example, the signal 1740, 1750 transmitted from either the local unit 1710 or transmitted from the appurtenance 230 can be such that the receiver of such signals should be within 3 feet.

Figure 18:
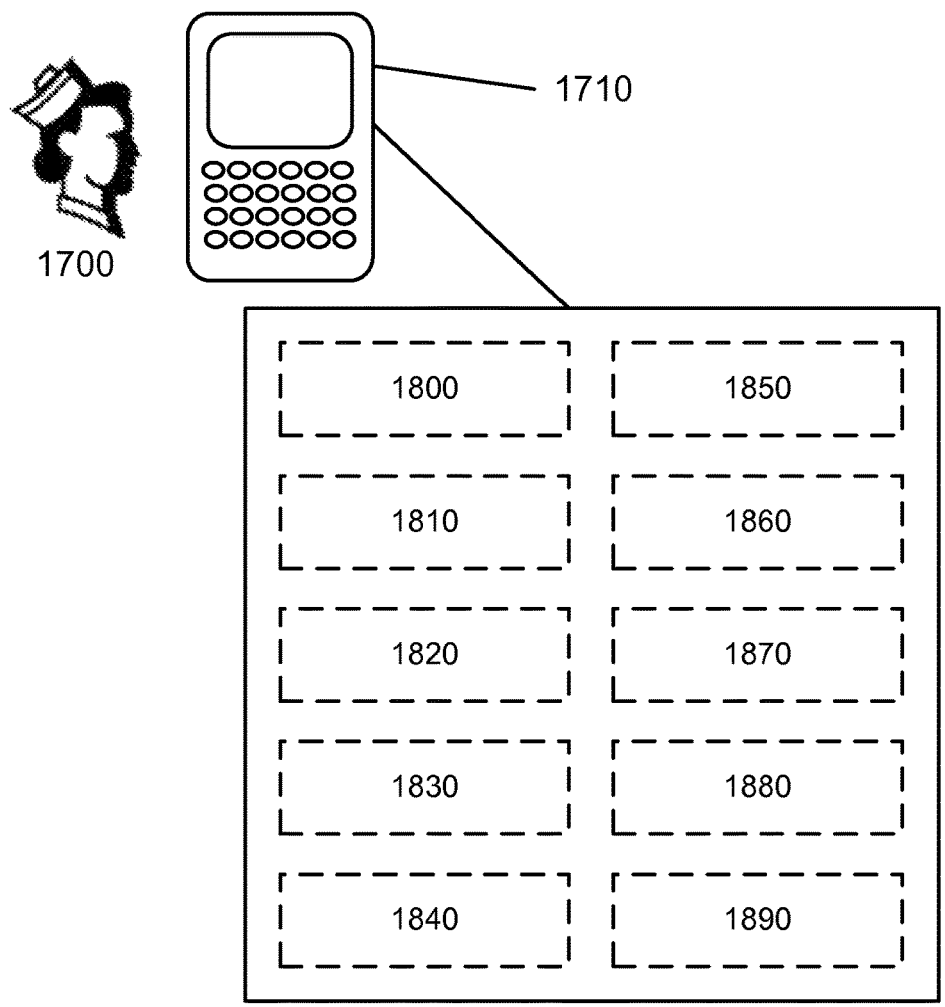
FIG. 18 depicts aspects of a local unit.
Figure 18:
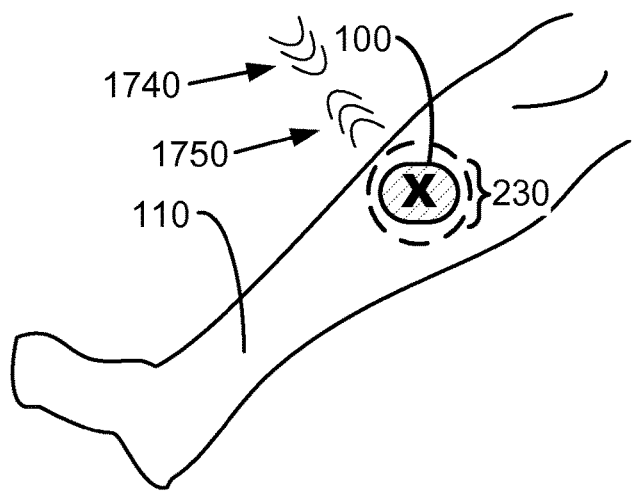

FIG. 18 illustrates aspects of a system including an appurtenance 230 used to monitor a cavity wound 100. As illustrated in FIG. 18, an appurtenance 230 is positioned relative to a cavity wound 100 on a body part 110 of a patient. The appurtenance 230 sends and receives signals 1740, 1750 from a local unit 1710. The local unit 1710 can be utilized by a user 1700.

FIG. 18 illustrates aspects of the local unit 1710. The local unit 1710 includes a housing, with connected user interface and input components (e.g. a display and keyboard). The local unit 1710 can include a processor 1800. The local unit 1710 can include memory 1810. The memory 1810 can include, for example, volatile and/or non-volatile memory. The local unit 1710 can include at least one antenna 1820. The local unit 1710 can include circuitry 1830, operably connected to the other components of the local unit 1710. The local unit 1710 can include one or more transmitters 1840. The local unit 1710 can include one or more receivers 1850. The local unit 1710 can include one or more power sources 1860, such as a battery, a solar cell, or a plug-in socket. The local unit 1710 can include logic 1870. The local unit 1710 can include other components 1880, 1890 as appropriate to a specific embodiment. The local unit 1710 can include, for example, an application specific intelligent microsensor as described in U.S. Pat. No. 6,889,165 to Lind et al., titled "Application Specific Intelligent Microsensors," which is incorporated herein by reference herein. The local unit 1710 can include, for example, a distinct identification signal. The local unit 1710 can include, for example, a visible indicator, such as a light. The local unit 1710 can include, for example, an identification code specific to that local unit 1710.

Figure 19:
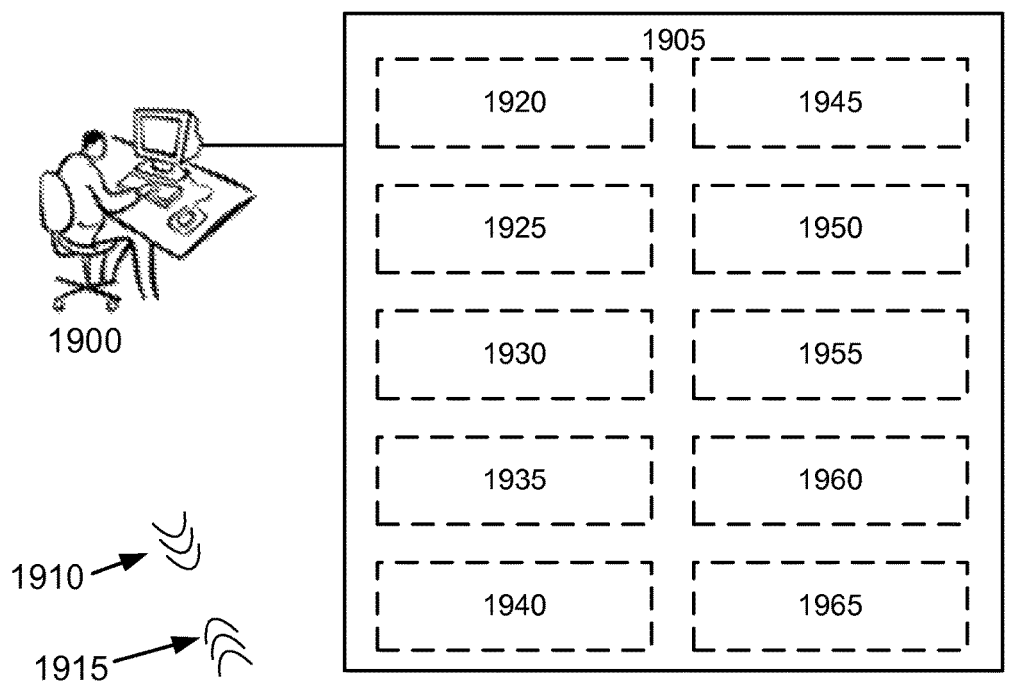
FIG. 19 shows aspects of a system including an appurtenance, a local unit and a central assembly.
Figure 19:
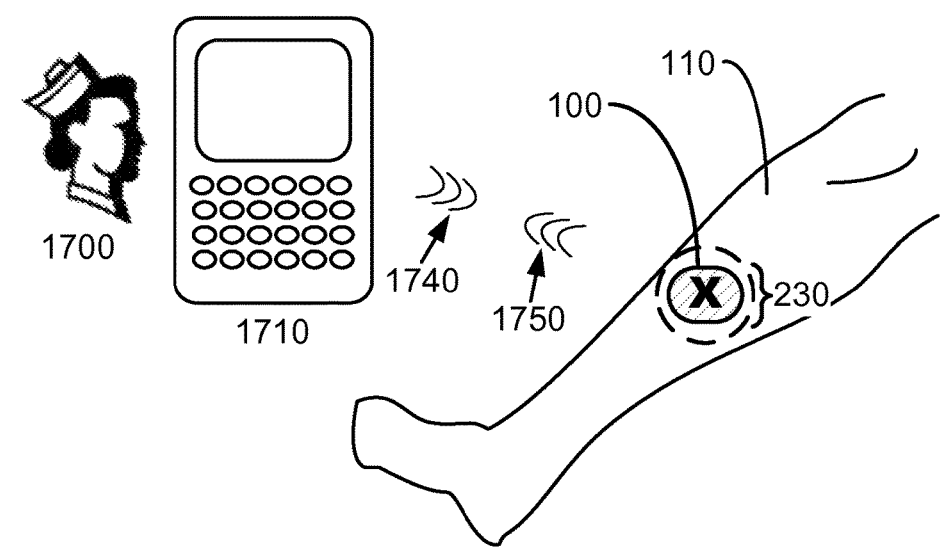

FIG. 19 shows aspects of a system including an appurtenance 230 to a cavity wound 100 dressing. As shown in FIG. 19, an appurtenance 230 is positioned relative to a cavity wound on a body part 110 of a patient. The appurtenance 230 associated with the wound 100 sends and receives signals 1740, 1750 from a local unit 1710. The local unit 1710 can be utilized by a user 1700.

Also as shown in FIG. 19, the local unit 1710 can send and receive signals 1905, 1910 from a central assembly 1905. The local unit 1710 can send and receive signals 1905, 1910 with a wireless connection, as shown in FIG. 19, or can send and receive signals 1905, 1910 through a wire connection. A central assembly 1905 includes at least one user interface device (e.g. a keyboard, touchscreen, display, etc.) which can be utilized by a system user 1900. A system user 1900 can include a medical caregiver, such as a nurse or doctor, or a patient caregiver, or a patient him- or herself, or other individual monitoring the wound dressing. Although system user 1900 is shown/described herein as a single illustrated figure, the system user 1900 can be representative of a human user, a robotic user (e.g., computational entity), and/or substantially any combination thereof (e.g., a user can be assisted by one or more robotic agents) unless context dictates otherwise. In general, the same can be said of "sender" and/or other entity-oriented terms as such terms are used herein unless context dictates otherwise.

FIG. 19 illustrates aspects of some embodiments of a central assembly 1905. A central assembly can be located primarily or mainly in one or a limited number of machines, for example one or more computer servers. A central assembly 1905 can interface with, or include, a 2G-RFID-Based E-Healthcare system. See, for example, Chen et al., "A 2G-RFID-Based E-Healthcare System," *IEEE Wireless Communications*, February 2010, pages 37-43, which is incorporated herein by reference. A central assembly 1905 can interface with, or include, a digital management system, for example as discussed in: Fisher, "Indoor Positioning and Digital Management Emerging Surveillance Regimes in Hospitals" in T. Monahan (Ed), Surveillance and Security: Technological Politics and Power in Everyday Life (pp. 77-88), New York: Routledge (2006); and Fisher and Monahan, "Tracking the Social Dimensions of RFID Systems in Hospitals," *International Journal of Medical Informatics* 77 (2008) 176-183, which are each incorporated herein by reference. A central assembly 1905 can interface with, or include, a drug tracking system, as described, for example, in "RFID Systems for Pharmaceutical Distributors to Meet the New FDA Regulations on Drugs," white paper from Abhisam Software, 2006, which is incorporated herein by reference. The central assembly 1905 can include, for example, at least one transmitter 1920. The central assembly 1905 can include, for example, at least one receiver 1925. The central assembly 1905 can include, for example, at least one antenna 1930. The central assembly 1905 can include, for example, memory, which can include non-volatile memory or volatile memory. The central assembly 1905 can include, for example, circuitry 1940. The circuitry 1940 can be operably connected to other components of the central assembly 1905. The central assembly 1905 can include, for example, a power source 1945. A power source 1945 can include, for example, at least one battery, a plug-in connection, a wireless power source, or a solar cell. The central assembly 1905 can include, for example, a processor 1950. The central assembly 1905 can include, for example, logic 1955. The central assembly 1905 can include, for example, additional components 1960, 1965.

Figure 20:
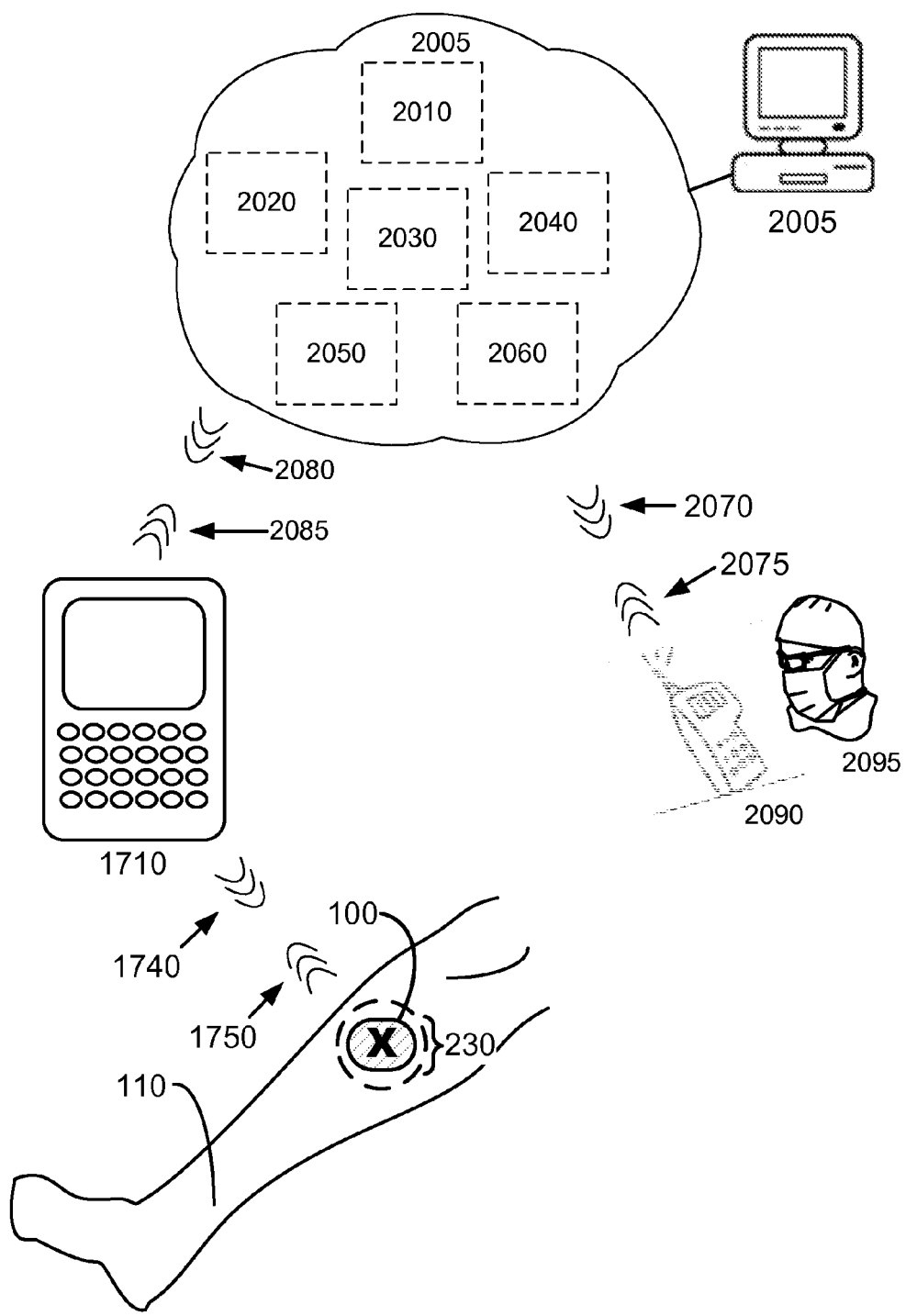
FIG. 20 illustrates a system for monitoring cavity wound dressings.

FIG. 20 illustrates aspects of a system including an appurtenance 230 used in association with a cavity wound 100 dressing. As illustrated in FIG. 20, an appurtenance 230 is used in association with a cavity wound 100 dressing on a body part 110 of a patient. The appurtenance 230 used in association with a cavity wound 100 dressing sends and receives signals 1740, 1750 from a local unit 1710. The local unit 1710 sends and receives signals 2080, 2085 from a central assembly 2005. The central assembly 2005 illustrated in FIG. 20 is in a "cloud" format, with a significant portion of its components distributed on a computer network, or a network of computing devices. The central assembly 2005 is configured to communicate with one or more interface devices, for example an individual computer. In some embodiments, the central assembly 2005 is configured to communicate directly with an appurtenance 230.

Depending on the embodiment, a cloud-based central assembly 2005 can include a plurality of components as illustrated in FIG. 20. For example, a central assembly 2005 can include logic 2010. For example, a central assembly 2005 can include circuitry 2020. The circuitry 2020 can be operably connected to other components of the central assembly 2005. For example, a central assembly 2005 can include memory 2030. For example, a central assembly 2005 can include one or more power sources 2040. For example, a central assembly 2005 can include at least one processor 2050. For example, a central assembly 2005 can include other components 2060.

Also as illustrated in FIG. 20, a central assembly 2005 can communicate with a remote device 2090 through signals 2070, 2075. Signals 2070 can be sent and signals 2075 can be received by an aspect of the central assembly 2005. Signals 2075 can be sent and signals 2070 can be received by the remote device 2090. Although the signals 2070, 2075 illustrated in FIG. 20 are wireless signals, in some embodiments the central assembly 2005 and a remote device 2090 can communicate through a wired connection. The remote device 2090 can be, for example, a pager, cell phone, laptop, PDA, tablet, smart phone or other device. The remote device 2090 can be, for example, incorporated into a wearable item. The remote device 2090 can be operated by a remote system user 2095. Some embodiments include a plurality of remote devices 2090, which can be operated by a plurality of remote system users 2095. The remote system users 2095 can include, for example, a care provider, medical personnel, a healthcare provider, and/or the patient.

In some embodiments, an appurtenance for monitoring a cavity wound comprises: a substrate configured to associate with a cavity wound dressing; a transmission unit attached to a surface of the substrate, the transmission unit including circuitry and at least one antenna operably attached to the circuitry; a selectively actuatable switch operably connected to the transmission unit; and one or more sensor units affixed to the substrate and operably connected to the selectively actuatable switch. For example, the substrate can be fabricated as a substantially planar, flexible structure. For example, the substrate can be fabricated as a three-dimensional structure configured to be placed within the cavity of a cavity wound in association with a primary dressing. For example, the substrate can be configured to irreversibly attach to a primary cavity wound dressing.

Some appurtenances to a cavity wound include a transmission unit. In some embodiments, the transmission unit can include a transmitter unit and a receiver. In some embodiments, the transmission unit is configured to transmit a signal in response to an interrogation signal. A transmission unit can include a radio frequency identification (RFID) device. A transmission unit can include a passive radio frequency identification (RFID) device. A transmission unit can include an active radio frequency identification (RFID) device. A transmission unit can include a Near Field Communication (NFC) device. A transmission unit can include non-volatile memory. A transmission unit can include volatile memory. A transmission unit can include a processor. A transmission unit can include a battery.

Some embodiments include an appurtenance including a selectively-actuatable switch. For example, the selectively actuatable switch can include a connector between the transmission unit and the one or more sensor units. For example, the selectively actuatable switch can include a physical conduit configured to allow a liquid to flow through the appurtenance to a location in contact with the at least one antenna of the transmission unit. For example, the selectively actuatable switch can include a wire connecting the transmission unit and the one or more sensor units. In some embodiments, the selectively actuatable switch is configured as a binary switch. In some embodiments, the selectively actuatable switch is configured to be irreversible. In some embodiments, the selectively actuatable switch is configured to be responsive to a change in capacitance.

Some embodiments include one or more sensor units affixed to a substrate and operably connected to a selectively actuatable switch. In some embodiments, the one or more sensor units include a plurality of sensor units of at least two distinct types oriented as a pattern relative to the wound-facing surface. For example, the sensor units can be oriented in a repeating array. For example, the sensor units can be oriented relative to the expected structure of the wound surface that will be adjacent to the wound-facing surface during use of the appurtenance. In some embodiments, the one or more sensor units include at least one sensor unit configured to detect physical pressure or temperature over time. For example, at least one sensor unit can be configured to detect physical pressure or temperature above preset minimum values. For example, at least one sensor unit can be configured to detect physical pressure or temperature and indicate a combined value for the two detected parameters. In some embodiments, the one or more sensor units include at least one antenna operably attached to at least one sensor unit. In some embodiments, the one or more sensor units include at least one chemical-based sensor unit. See, for example: U.S. Pat. No. 7,951,605 to Pitner et al., "Multianalyte Sensor;" US Patent Application No. 2011/0082356 to Yang et al., "Analyte Sensor Apparatuses Having Interference Rejection Membranes and Methods for Making and Using Them;" US Patent Application No. 2010/0331634 to Muller et al., "Hydrogel Implant for Sensing Metabolites in Body Tissue;" and U.S. Pat. No. 7,964,390 to Rozakis, "Sensor System;" which are each incorporated by reference herein. For example, a chemical-based sensor unit can include a chemical-based detector. For example, a chemical-based sensor unit can include a chemical-based indicator, such as a chemical-based indicator including a color changing chemical. In some embodiments, the one or more sensor units include at least one positional indicator. For example, a positional indicator can indicate the relative distance of the sensor unit from an edge region of the appurtenance. For example, a positional indicator can indicate the position of the appurtenance relative to its expected depth in the cavity of the cavity wound during use. In some embodiments, the one or more sensor units include at least one fluid-activated sensor unit. For example, a sensor unit can be activated in the presence of fluid flow through an aperture in the appurtenance into an interior region of the sensor unit. In some embodiments, the one or more sensor units include at least one sensor unit including an optically resolvable detection indicator. For example, a sensor unit can include a visible detection indicator, such as a visible color change or an LED that can be illuminated as an indicator. For example, a sensor unit can include an optically resolvable detection indicator that can be resolved with an external optical device, such as an external device with a light source in the ultraviolet (UV) range, or a light source for light of a specific wavelength (e.g. a wavelength matched to the excitation energy characteristics of a chemical present in the sensor unit that has its properties altered by the presence of an analyte. In some embodiments, the one or more sensor units include at least one sensor unit including an indicator with an RFID antenna. For example, a sensor unit can be configured to send an RFID signal in response to the detection of an analyte. For example, a sensor unit can be configured to respond to a RFID signal in a specific manner after the detection of an analyte.

Some embodiments include an appurtenance including: an edge region of the appurtenance, the edge region including at least one surface configured to be oriented away from the wound; and at least one orientation indicator attached to the edge region. For example, an orientation indicator can be an external marking visible to a caregiver. For example, an orientation indicator can be a nonvisible marking that is detectable by an external device, such as in the presence of a specific wavelength of light. In some embodiments, an orientation indicator includes both a visible and a nonvisible marking. An orientation indicator that includes a nonvisible marking can be used, for example, to orient the appurtenance after use when the appurtenance is being scanned by an external device to capture information from the indicators in the sensor units attached to the appurtenance. Some embodiments include an appurtenance including: an edge region of the appurtenance, the edge region including at least one surface configured to be oriented away from the wound; and at least one temperature sensor unit attached to the edge region. For example, a temperature sensor attached to an edge region of an appurtenance can be configured to detect ambient temperature around the cavity wound. For example, a temperature sensor attached to an edge region of an appurtenance can be configured to detect the surface temperature of the patient in the periwound region.

Some embodiments include: a wound dressing, the wound dressing configured to be used in association with the appurtenance; and a second wound dressing, the second wound dressing configured to cover a wound region and stabilize the appurtenance and the wound dressing during use, the second wound dressing configured to be removable from the wound region after use. For example, an appurtenance can be distributed as a kit, packaged with a primary and a secondary dressing configured for use together with the appurtenance. In some embodiments, the appurtenance is functional when wet, for example in the presence of a saline-dampened wound dressing. In some embodiments, the appurtenance is functional when wet, for example for use in a physiologically damp wound cavity. Some embodiments include a detachable cover configured to reversibly mate with at least one wound-facing surface of the substrate. For example, a detachable cover can include a thin plastic film configured to reversibly affix to at least one wound-facing surface of the substrate of the appurtenance, and to be removed prior to use of the appurtenance. In some embodiments, the appurtenance is substantially sterilized prior to use. For example, the appurtenance can be substantially sterilized prior to inclusion in a cavity wound dressing medical kit. For example, the appurtenance can be substantially sterilized along with other components of a cavity wound dressing medical kit.

In some embodiments, the appurtenance includes a selectively actuatable switch operably connected to a transmission unit. Some embodiments also include an indicator operably attached to the selectively actuatable switch. For example, an indicator can include an LED attached to an edge region of the appurtenance. Some embodiments include a battery. Some embodiments include a processor and a transceiver. In some embodiments, the transmission unit includes a pressure sensitive activation region, wherein the pressure sensitive activation region is configured to be activated by physical pressure on at least one sensor unit. In some embodiments, the transmission unit includes a pressure sensitive activation region, wherein the pressure sensitive activation region is configured to be activated by physical pressure on the wound-facing surface of the appurtenance. For example, the pressure sensitive activation region can be configured to activate the transmission unit in the presence of physical pressure above 30 mm Hg in the region adjacent to the wound surface. For example, the pressure sensitive activation region can be configured to activate the transmission unit in the presence of physical pressure above 40 mm Hg in the region adjacent to the wound surface. For example, the pressure sensitive activation region can be configured to activate the transmission unit in the presence of physical pressure above 50 mm Hg in the region adjacent to the wound surface.

Some embodiments of an appurtenance to a cavity wound dressing include: a substrate configured to fit substantially within a cavity wound in association with a primary wound dressing; and a plurality of sensor units attached to the substrate, each of the sensor units including a detector and an indicator, wherein the indicator includes a passive radio frequency identification (RFID) unit. For example, an indicator including a passive radio frequency identification (RFID) unit can be configured to alter the response of the passive RFID to an interrogation signal in response to the associated detector.

Some embodiments include a system for monitoring a cavity wound medical dressing, including: an appurtenance to a cavity wound dressing, the appurtenance including a substrate and a plurality of sensor units, wherein each of the sensor units include an indicator configured to respond to a specific external signal; and an external device configured to transmit the specific external signal and detect the response of the indicator included with each of the plurality of sensor units. For example, an appurtenance can include a plurality of attached sensor units that include detectors that recognize a specific analyte by binding to that analyte. The sensor units also include indicators that respond to the analyte binding by the detector with a structural change in a chemical component of the indicator chemistry, wherein the structural changes result in an altered response to a signal transmitted by an external device. The indicators can include, for example, one or more RFID antennas and the external device include a radio frequency signal transmitter and receiver. The indicators can include, for example, a chemical compound configured to reflect some wavelengths of light differently in different conformations, and the external device include an emitter of the specific light wavelengths and a receiver for the reflections.

In some embodiments, an appurtenance is configured to provide an automatic notification of detection of a condition in a cavity wound. For example, a sensor unit attached to a battery and a LED light on the edge of the appurtenance can be configured to initiate the light turning on in response to a detected analyte. For example, a sensor unit attached to a battery and an active RFID unit can be configured to transmit a RFID signal in response to a condition, such as physical pressure above a preset maximum threshold in the wound cavity. In some embodiments, an automatic notification of detection of a condition in a cavity wound is a notification that is apparent by an observer externally to the wound dressing, without the use of additional devices. For example, an appurtenance can include a plurality of sensor units with detectors configured to respond to physical pressure above a preset threshold level, and indicators that include audible alarms in response to the detection. A caregiver and/or a cavity wound patient can hear the audible alarm in real-time, giving these individuals the opportunity to quickly intervene and reduce the physical pressure at the cavity wound site. An appurtenance can be removable with a wound dressing change and the attached sensor units subsequently interrogated, such as with a RFID transmitter and receiver device. In some embodiments, an appurtenance can be left in situ in a cavity wound during interrogation by an external device, such as a RFID transmitter and receiver.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. Optical aspects of implementations will typically employ optically-oriented hardware, software, and or firmware.

In some implementations described herein, logic and similar implementations can include software or other control structures. Electronic circuitry, for example, can have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled//implemented/translated/ converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which can then be used to create a physical implementation having hardware (e.g., an Application Specific Integrated Circuit).

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be achievable in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that can impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context can dictate otherwise.

In a general sense, the various aspects described herein can be implemented, individually and/or collectively, by a wide range of hardware, software, firmware, and/or any combination thereof and can be viewed as being composed of various types of "circuitry" or "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

The herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific example is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components, and/or wirelessly interactable, and/or wirelessly interacting components, and/or logically interacting, and/or logically interactable components.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended as the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended as the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein can generally be performed in any order. Also, although various operational flows are presented in a sequence(s), it should be understood that the various operations can be performed in other orders than those which are illustrated, or can be performed concurrently. Examples of such alternate orderings can include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. An appurtenance to a cavity wound dressing for a cavity wound, the appurtenance comprising:
    a substrate configured to be positioned inside the cavity wound, the substrate including, at least one wound-facing surface, the wound-facing surface configured to be oriented facing a wound surface of the cavity wound; and
    at least one cavity-facing surface facing away from the wound surface and defining an interior space within the substrate and the cavity wound that is sized and configured to contain the cavity wound dressing therein, wherein the substrate is distinct from the cavity wound dressing;
    an edge region including at least one surface configured to be oriented away from the wound surface and at least one surface configured to be oriented facing a periwound region of the cavity wound; and
    a plurality of sensor units attached to the substrate, the plurality of sensors including at least one temperature sensor attached to the edge region;
    wherein the at least one wound-facing surface is configured to press against the wound surface with a pressure of less than 32 mm Hg (4.3 kPa) when the edge region contacts the periwound region of the cavity wound.

2. The appurtenance of claim 1, wherein the substrate comprises:
    a plurality of unidirectional fluid flow structures, wherein the unidirectional fluid flow structures are configured to allow fluid flow from the wound-facing surface to one or more of the plurality of sensor units attached to the substrate.

3. The appurtenance of claim 1, wherein the plurality of sensor units attached to the substrate comprise:
    a plurality of sensor units of at least two distinct types.

4. The appurtenance of claim 1, wherein the plurality of sensor units attached to the substrate comprise:
    at least one sensor unit configured to detect physical pressure, at least one sensor unit configured to detect temperature, and at least one sensor unit configured to record an elapsed time value.

5. The appurtenance of claim 1, wherein the plurality of sensor units attached to the substrate comprise:
    at least one sensor unit configured to detect one or more analytes of wound exudate.

6. The appurtenance of claim 1, wherein the plurality of sensor units attached to the substrate comprise:
    at least one antenna operably connected to at least one sensor unit.

7. The appurtenance of claim 1, wherein the plurality of sensor units attached to the substrate comprise:
    at least one chemical-based sensor unit.

8. The appurtenance of claim 1, wherein the plurality of sensor units attached to the substrate comprise:
    at least one sensor unit including an optically resolvable detection indicator.

9. The appurtenance of claim 1, wherein the at least one wound-facing surface of the substrate has a size and a shape that approximate the size and shape of the cavity wound.

10. The appurtenance of claim 1, wherein the substrate is configured to be attached to the cavity wound dressing using a chemical attachment or a mechanical attachment.

11. The appurtenance of claim 1, wherein the wound-facing surface is configured to press against the wound surface with a pressure of less than 12 mm Hg (1.6 kPa).

12. The appurtenance of claim 1, further comprising the cavity wound dressing disposed within the interior space.

13. The appurtenance of claim 1, wherein the edge region includes a visible orientation indicator.

14. The appurtenance of claim 1, wherein at least one of the plurality of sensor units defines a conduit, the at least one of the plurality of sensor units including a detector disposed in the conduit.

15. The appurtenance of claim 1, wherein:
    the substrate defines a plurality of apertures; and
    at least one of the plurality of sensor units is a positioned adjacent to each of the plurality of apertures.

* * * * *

UNITED STATES PATENT AND TRADEMARK OFFICE
CERTIFICATE OF CORRECTION

PATENT NO. : 10,226,212 B2  
APPLICATION NO. : 13/795667  
DATED : March 12, 2019  
INVENTOR(S) : Paul Duesterhoft et al.

Page 1 of 1

It is certified that error appears in the above-identified patent and that said Letters Patent is hereby corrected as shown below:

In the Claims

In Column 50, Claim 15, Line 54, delete "at least one of the plurality of sensor units is a positioned" and insert -- at least one of the plurality of sensor units is positioned -- therefor.

Signed and Sealed this  
Thirteenth Day of August, 2019

Andrei Iancu  
*Director of the United States Patent and Trademark Office*